United States Patent
Chang et al.

(10) Patent No.: US 7,622,612 B2
(45) Date of Patent: Nov. 24, 2009

(54) TRICYCLIC DERIVATIVES AND THEIR USE

(75) Inventors: Dong Jo Chang, Seocho-gu (KR); Eun Young Yoon, Gwanak-gu (KR); Gun Bong Lee, Seongnam-si (KR); Soon Ok Kim, Suwon-si (KR); Wan Joo Kim, Songpa-gu (KR)

(73) Assignees: Chemtech Research Incorporation, Kyunggi-do (KR); KT & G Corporation, Daejeon (KR)

( * ) Notice: Subject to any disclaimer, the term of this patent is extended or adjusted under 35 U.S.C. 154(b) by 520 days.

(21) Appl. No.: 11/482,855

(22) Filed: Jul. 10, 2006

(65) Prior Publication Data

US 2007/0021427 A1 Jan. 25, 2007

Related U.S. Application Data

(63) Continuation-in-part of application No. 10/479,057, filed as application No. PCT/KR02/00996 on May 27, 2002, now Pat. No. 7,119,229.

(30) Foreign Application Priority Data

May 28, 2001 (KR) ............................... 2001-29341

(51) Int. Cl.
  C07C 233/65 (2006.01)
  A61K 31/165 (2006.01)
(52) U.S. Cl. .................... 564/163; 564/74; 564/162; 564/185; 514/599; 514/617; 514/618
(58) Field of Classification Search .................... 564/74, 564/162, 163, 185; 514/599, 617, 618
  See application file for complete search history.

(56) References Cited

U.S. PATENT DOCUMENTS

| 3,222,253 A | 12/1965 | Eschenmoser et al. |
| 4,533,675 A | 8/1985 | Brossi et al. |

FOREIGN PATENT DOCUMENTS

| FR | 2.002.496 | 10/1969 |
| WO | 91/02084 | 2/1991 |
| WO | 2004/113281 | 12/2004 |

OTHER PUBLICATIONS

Shi, et al., "Antitumor Agents. 172. Synthesis and Biological Evaluation of Novel Deacetamidothiocolchicin-7-ols and Ester Analogs as Antitubulin Agents." *J. Med. Chem*, 1997, vol. 40, pp. 961-966. American Chemical Society, Washington, D.C.
Muzaffar et al., "Antitubulin Effects of Derivatives of 3-Demethylthiocolchicine, Methylthio Ethers of Natural Colchicinoids, and Thioketones Derived from Thiocolchicine. Comparison with Colchicinoids." *J. Med. Chem.*, 1990, vol. 33, pp. 567-571. American Chemical Society, Washington, D.C.
Kerekes et al., "Synthesis and Biological Effects of Novel Thiocolchicines. 3. Evaluation of N-Acyldeacetylthiocolchicines, N-(Alkoxycarbonyl)deacetylthiocolchicines, and O-Ethyldemethylthiocolchicines. New Synthesis of Thiodemecolcine and Antileukemic Effects of 2-Demethyl- and 3-Demethylthiocolchicine." *J. Med. Chem.*, 1985, vol. 28, pp. 1204-1208, American Chemical Society, Washington, D.C.
Malkinson, "Colchicine: New Uses of an Old, Old Drug." *Arch Dermatol*, vol. 118, Jul. 1982, pp. 453-457. American Medical Association, Chicago, IL.
Boyé et al., "Tropolonic *Colchicum* Alkaloids and Allo Congeners." *The Alkaloids*. 1992. vol. 41, Chapter 3, pp. 125-176. Academic Press, Inc., New York, NY.
Andreu, "Interaction of Tubulin with Bifunctional Colchicine Analogues: An Equilibrium Study." *Biochemistry*, 1984, vol. 23, pp. 1742-1752. American Chemical Society, Washington, D.C.
Pyles et al., "Effect of the B Ring and the C-7 Substituent on the Kinetics of Colchicinoid-Tubulin Associations." *Biochemistry*, 1993, vol. 32, pp. 2329-2336. American Chemical Society, Washington, D.C.
Williams et al., "A Photoaffinity Derivative of Colchicine: 6'-(4'-Azido-2'-nitrophenylamino)hexanoyldeacetylcochicine. Photolabeling and Location of the Colchicine-Binding Site on the α-Subunit of Tubulin." *The Journal of Biological Chemistry*, 1985, vol. 260, No. 25, pp. 13794-13800. The American Society of Biological Chemists, Inc., Baltimore, MD.

(Continued)

*Primary Examiner*—Shailendra Kumar
(74) *Attorney, Agent, or Firm*—Buchanan Ingersoll & Rooney PC

(57) ABSTRACT

The present invention relates to tricyclic colchicine derivatives represented by the formulas (I) or (II), pharmaceutically acceptable salts thereof, and a method for providing an immuno-suppressive or immuno-modulating effect, an anti-proliferative effect, an anti-inflammatory effect or a method for treating cancer comprising administering to a patient an effective amount of one or more colchicine derivatives:

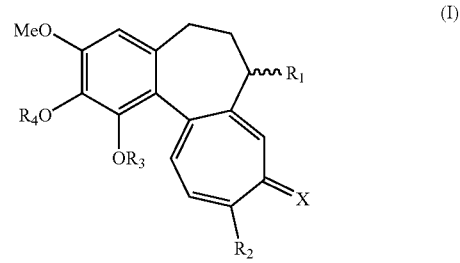

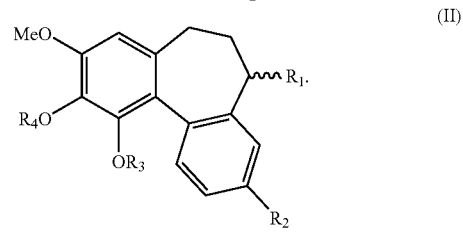

8 Claims, 10 Drawing Sheets

OTHER PUBLICATIONS

Ostermann et al., "Colchicine Allows Prolonged survival of Highly Reactive Renal Allograft in the Rat." *Journal of the American Society of Nephrology*, 1993, vol. 4, No. 6, pp. 1294-1299, The American Society of Nephrology, Washington, D.C.

Kang et al., "*N*-Acetylcolchinol *O*-Methyl Ether and Thiocolchicine, Potent Analogs of Colchicine Modified in the C Ring: Evaluation of the Mechanistic Basis for Their Enhanced Biological Properties." *The Journal of Biological Chemistry*, 1990, vol. 265, No. 18, pp. 10255-10259. The American Society of Biochemistry and Molecular Biology, Inc., Baltimore, MD.

Quinn, "Toxicity Quantitative Structure-Activity Relationships of Colchicines." *J. Med. Chem.*, 1981, vol. 24, pp. 636-639. American Chemical Society, Washington, D.C.

Quinn, "Quantitative Structure-Activity Relationships of Colchicines against P388 Leukemia in Mice." *J. Med. Chem.*, 1981, vol. 24, pp. 251-256. American Chemical Society, Washington, D.C.

Hansch et al. "Antitumor Structure-Activity Relationships. Nitrosources vs. L-1210 Leukemia." *J. Med. Chem.*, 1980, vol. 23, pp. 1095-1101. American Chemical Society, Washington, D.C.

Shiau et al., "Alkylthiocolchicines and *N*-Deacetyl-alkylthiocolchicines and Their Antileukemic Activity." *Journal of Pharmaceutical Sciences*, Apr. 1975, vol. 64, No. 4, pp. 646-648. American Pharmaceutical Association, Easton, PA.

Poulev et al., "Regioselective Bioconversion of Colchicine and Thiocolchicine into Their Corresponding 3-Demethyl Derivatives." *Journal of Fermentation and Bioengineering*, 1995, vol. 79, No. 1, pp. 33-38. Elsevier Science Inc., New York, NY.

Li et al., "Antitumor Agents. 150. 2',3',4',5',5,6,7-Substituted 2-Phenyl-4-quinolones and Related Compounds: Their Synthesis, Cytotoxicity, and Inhibition of Tubulin Polymerization." *J. Med. Chem.*, 1994, vol. 37, pp. 1126-1135. American Chemical Society, Washington, D.C.

Andreu et al., "Interaction of Tubulin with Bifunctional Colchicine Analogues: An Equilibrium Study." *Biochemistry*, 1984, vol. 23, pp. 1742-1752. American Chemical Society, Washington, D.C.

Capraro et al., "Simple Conversion of Colchicine into Demecolcine." *Helvetica Chimica Acta*, 1979, vol. 62, Fasc. 4, No. 99, pp. 965-970. Verlag Helvetica Chimica Acta, Basel, Switzerland.

Iorio, "Contraction of Tropolonic Ring of Colchicine by Hydrogen Peroxide Oxidation." *Heterocycles*, 1984, vol. 22, No. 10, pp. 2207-2211. Elsevier, New York, NY.

Jang, "Comparison of Pancreas Transplantation Outcome Between the Cyclosporine and Tacrolimus Eras." *Transplantation Proceedings*, 2000, vol. 32, pp. 2470-2471. Elsevier Science Inc., New York, NY.

Guo et al., "Role of Natural Killer Cells in Allograft Rejection." *Transplantation Proceedings*, 2000, vol. 32, pp. 2089-2090. Elsevier Science Inc., New York, NY.

Jang et al., "Tacrolimus for Rescue Therapy in Refractory Renal Allograft Rejection." *Transplantation Proceedings*, 2000, vol. 32, pp. 1765-1766. Elsevier Science Inc., New York, NY.

Jang et al., "Conversion from Cyclosporine to Tacrolimus in Renal Allograft Recipients with Delayed Graft Function from Severe Acute Tubular Necrosis." *Transplantation Proceedings*, 2000, vol. 32, pp. 1714-1715. Elsevier Science Inc., New York, NY.

SEQUENCE LISTING

<160> NUMBER OF SEQ ID NOS: 10

<210> SEQ ID NO 1
<211> LENGTH: 24
<212> TYPE: DNA
<213> ORGANISM: Artificial
<220> FEATURE:
<223> OTHER INFORMATION: primer

<400> SEQUENCE: 1
tttggagcag aagtgcaaag tctc        24

<210> SEQ ID NO 2
<211> LENGTH: 24
<212> TYPE: DNA
<213> ORGANISM: Artificial
<220> FEATURE:
<223> OTHER INFORMATION: primer

<400> SEQUENCE: 2
gatcaggagg gatttcaaag acct        24

<210> SEQ ID NO 3
<211> LENGTH: 20
<212> TYPE: DNA
<213> ORGANISM: Artificial
<220> FEATURE:

<223> OTHER INFORMATION: primer

<400> SEQUENCE: 3
ccgtggtgaa tgtatgagca							20

<210> SEQ ID NO 4
<211> LENGTH: 20
<212> TYPE: DNA
<213> ORGANISM: Artificial
<220> FEATURE:
<223> OTHER INFORMATION: primer

<400> SEQUENCE: 4
cctcgcttct gatctgtctt							20

<210> SEQ ID NO 5
<211> LENGTH: 18
<212> TYPE: DNA
<213> ORGANISM: Artificial
<220> FEATURE:
<223> OTHER INFORMATION: primer

<400> SEQUENCE: 5
atgagcacag aaagcatg							18

<210> SEQ ID NO 6
<211> LENGTH: 18
<212> TYPE: DNA
<213> ORGANISM: Artificial
<220> FEATURE:
<223> OTHER INFORMATION: primer

<400> SEQUENCE: 6
tcacagagca atgactcc							18

<210> SEQ ID NO 7
<211> LENGTH: 19
<212> TYPE: DNA
<213> ORGANISM: Artificial
<220> FEATURE:
<223> OTHER INFORMATION: primer

<400> SEQUENCE: 7
atggcaactg ttcctgaac							19

<210> SEQ ID NO 8
<211> LENGTH: 18
<212> TYPE: DNA
<213> ORGANISM: Artificial
<220> FEATURE:
<223> OTHER INFORMATION: primer

<400> SEQUENCE: 8
ttaggaagac acggattc							18

<210> SEQ ID NO 9
<211> LENGTH: 20
<212> TYPE: DNA
<213> ORGANISM: Artificial
<220> FEATURE:
<223> OTHER INFORMATION: primer

<400> SEQUENCE: 9
tccttcgttg ccggtccaca							20

```
<210> SEQ ID NO 10
<211> LENGTH: 20
<212> TYPE: DNA
<213> ORGANISM: Artificial
<220> FEATURE:
<223> OTHER INFORMATION: primer

<400> SEQUENCE: 10
cgtctccgga gtccatcaca                                              20
```

TRICYCLIC DERIVATIVES AND THEIR USE

This application is a continuation-in-part application of U.S. patent Ser. No. 10/479,057 filed on Nov. 26, 2003, now U.S. Pat. No. 7,119,229, which is a 371 of PCT/KR02/00996, filed May 27, 2002.

FIELD OF THE INVENTION

The present invention relates to novel tricyclic colchicine derivatives represented by the formulas (I) or (II), or pharmaceutically acceptable salts thereof, and a method for providing an immuno-suppressive or immuno-modulating effect, an anti-proliferative effect, an anti-inflammatory effect or a method for treating cancer comprising administering to a patient an effective amount of one or more colchicine derivatives.

BACKGROUND OF THE INVENTION

Colchicine is a pseudo-alkaloid widely used for treatment of gout and is used only for short-term therapeutic treatment due to its toxicity. However, colchicine has been reported to exhibit a very fast and unique therapeutic effect on gout (reference: The Alkaloids, 1991, vol. 41, 125-176; U.S. Pat. No. 4,533,675).

There is also a report that colchicine inhibits formation of mitotic spindle during cell division, thereby suppressing cell division, which leads to activation of anticancer and anti-proliferative effects. Continuous research into colchicine applications has been carried out and as a result, a number of colchicine derivatives have been synthesized up to now (U.S. Pat. No. 3,222,253, U.S. Pat. Serial No. 00/608073A, and WO 91/02084). Among them, only demecolcine is currently being used for treatment of leukemia.

There is another report that colchicine was used for treatment of psoriasis or rheumatoid arthritis and has an amyloidosis inhibitory effect and an anti-inflammatory effect (reference: *Arch. Dermatol.* 1982, Vol 118, July, p 453-457). In addition, thiocolchicoside, one of colchicine derivatives, is broadly used for treatment of skeletal muscle contracture and inflammation.

SUMMARY OF THE INVENTION

Therefore, the present invention has been made in view of the above problems, and it is an object of the present invention to provide a novel colchicine derivative having anticancer, anti-proliferative and anti-inflammatory effects and immuno-suppressive and muscle-relaxing functions, and pharmaceutically acceptable salts thereof.

Another object of the present invention is to provide methods for preparing the colchicine derivatives.

Still another object of the present invention is to provide a method for providing an immuno-suppressive or immuno-modulating effect, an anti-proliferative effect, an anti-inflammatory effect or a method for treating cancer comprising administering to a patient in need of such an effect an effective amount of one or more colchicine derivatives.

BRIEF DESCRIPTION OF DRAWINGS

FIG. 3 shows the results of cytokine profile investigation of standard compound and colchicine derivatives according to the present invention.

FIG. 6A shows a picture of a control mouse paw (left one), a picture of a test mouse paw taken on 34 days after beginning the CIA test (middle one), and a picture of a test mouse paw taken on 34 days after beginning the CIA test in case of injecting compound 3 (right one). FIG. 6B shows Arthritis Index of the 24th day to the 42nd day after first immunization in a control group (○), a CIA test group (●), and a CIA test group treated with compound 3 (□). FIG. 6C shows % Arthritis of the 24th day to the 42nd day after first immunization in a control group (○), a CIA test group (●), and a CIA test group treated with compound 3 (□).

FIG. 7A is the RT-PCR result of iNOS, COX-2, TNF-α, IL-1β, and GAPDH; FIG. 7B is mRNA expressions of iNOS, COX-2, TNF-α, IL-1β which are compared with GAPDH. FIGS. 7C-7F show the amount of NO2-, PGE2, TNF-α, and IL-1β in the bloods inside the bloods from the mice through the CIA model, respectively.

DISCLOSURE OF THE INVENTION

Figure 1:
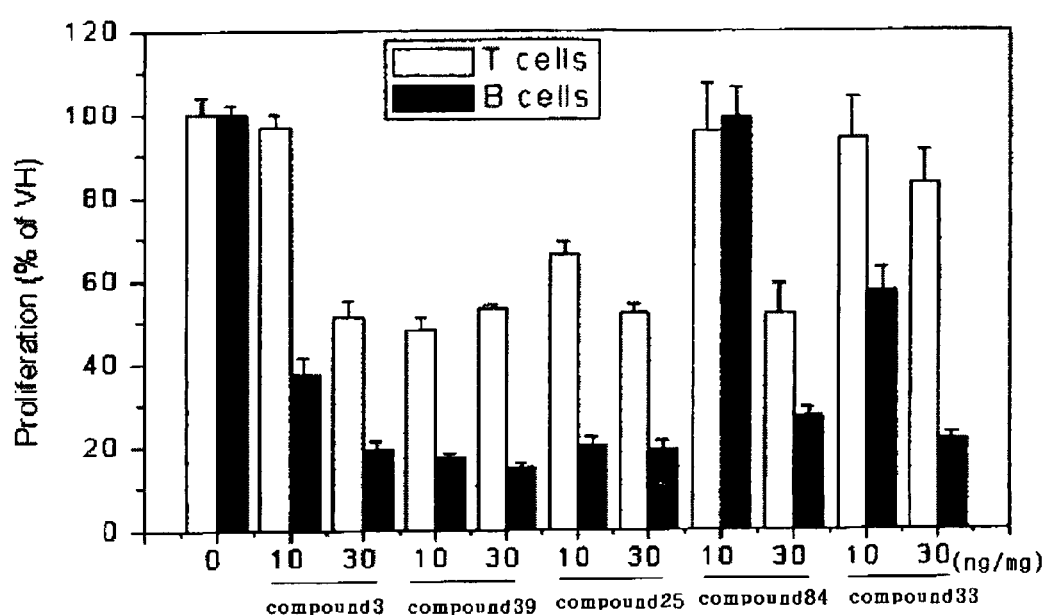
FIG. 1 shows anti-proliferative and immunosuppressive effects on T-cell and B-cell after treating BALB/c mouse spleen cells with colchicine derivatives according to the present invention (compounds 3, 25, 33, 39 and 84).

In accordance with an aspect of the present invention, the above and other objects can be accomplished by the provision of colchicine derivatives represented by the formulas (I) or (II), and pharmaceutically acceptable salts thereof:

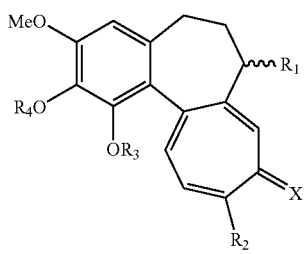

(I)

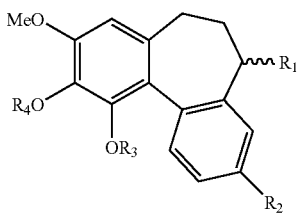

(II)

Given that when $R_1$ is $N(R_5)C(X_1)$—A, $R_2$ is hydrogen, $X_2R_6$, or $X_2(O)n_1R_6$; $R_3$ and $R_4$ are independently hydrogen, a methyl group, or a lower straight chain or branched alkyl, wherein $R_5$ and $R_6$ are independently hydrogen, or a lower straight chain or branched alkyl; $X$, $X_1$, and $X_2$ are independently O or S; $n_1$ is an integer of 1 or 2; and A is selected from the group represented by the following formula (a), (b), (c), (d), (e), (f) or (g):

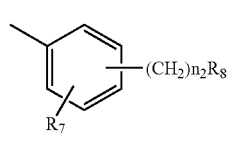  (a)

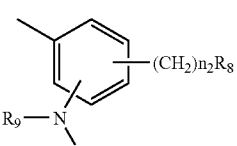  (b)

—$Y_1$—$(CH_2)n_2R_8$  (c)

—$Y_2$—$(CH_2)n_2R_8$  (d)

—$Y_3$—$(CH_2)n_2R_8$  (e)

—$Y_4$—$(CH_2)n_2R_8$  (f)

—$Y_5$—$(CH_2)n_2R_8$  (g)

wherein $R_7$ is a phenyl, a $C_1$ to $C_3$ straight chain or branched alkyl, a $C_1$ to $C_3$ straight chain or branched alkoxy, halogen selected from F, Cl, Br or I, a nitro, or a cyano group; $R_8$ is hydrogen, —$ONO_2$, halogen selected from F, Cl, Br, or I; $R_9$ is hydrogen, a $C_1$ to $C_3$ alkyl, or $NHCOR_{10}$, wherein $R_{10}$ is a $C_1$ to $C_4$ alkyl; $n_2$ is an integer from 1 to 3; $Y_1$ is one of the following $C_3$ to $C_6$ unsaturated ring structure containing 1 to 2 hetero atoms among S, O, or N:

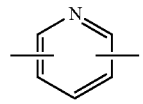 $Y_{1-1}$

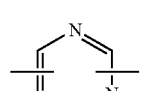 $Y_{1-2}$

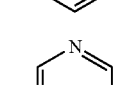 $Y_{1-3}$

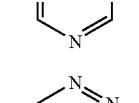 $Y_{1-4}$

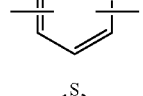 $Y_{1-5}$

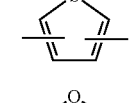 $Y_{1-6}$

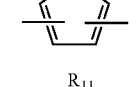 $Y_{1-7}$

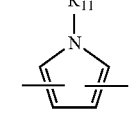 $Y_{1-8}$

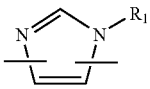 $Y_{1-9}$

 $Y_{1-10}$

 $Y_{1-11}$ wherein substituents of $Y_{1-1}$ are placed at the $C_2$ and $C_6$ positions or the $C_2$ and $C_4$ positions of the pyridine, substituents of $Y_{1-2}$ are placed at the $C_2$ and $C_4$ positions or the $C_4$ and $C_6$ positions of the pyrimidine, substituents of $Y_{1-3}$ are placed at the $C_2$ and $C_6$ positions of the pyrazine, substituents of $Y_{1-4}$ are placed at the $C_4$ and $C_6$ positions of the pyridazine, substituents of $Y_{1-5}$ are placed at the $C_2$ and $C_5$ positions or the $C_2$ and $C_4$ positions of the thiophen, substituents of $Y_{1-6}$ are placed at the $C_2$ and $C_5$ positions or the $C_2$ and $C_4$ positions of the furan, substituents of $Y_{1-7}$ are placed at the $C_2$ and $C_5$ positions or the $C_2$ and $C_4$ positions of the pyrrole, substituents of $Y_{1-8}$ are placed at the $C_2$ and $C_5$ positions or the $C_2$ and $C_4$ positions of the imidazole, substituents of $Y_{1-9}$ are placed at the $C_2$ and $C_5$ positions of the ring, substituents of $Y_{1-10}$ are placed at the $C_3$ and $C_5$ positions of the ring, and substituents of $Y_{1-11}$ are placed at the $C_3$ and $C_5$ positions of the pyrazole;

wherein $R_{11}$ is hydrogen, a $C_1$ to $C_5$ alkyl, or $NHCOR_{12}$, $R_{12}$ is hydrogen, or a $C_1$ to $C_5$ alkyl; $Y_2$ is a $C_3$ to $C_5$ saturated ring; $Y_3$ is represented by the following formula of a $C_2$ to $C_5$ heterocyclic ring:

In accordance with still another aspect of the present invention, there is provided methods for preparing the colchicine derivative (Ia) represented by the formulas (I) and (II) according to the reaction scheme 1.

Reaction scheme 1 (Method 1)

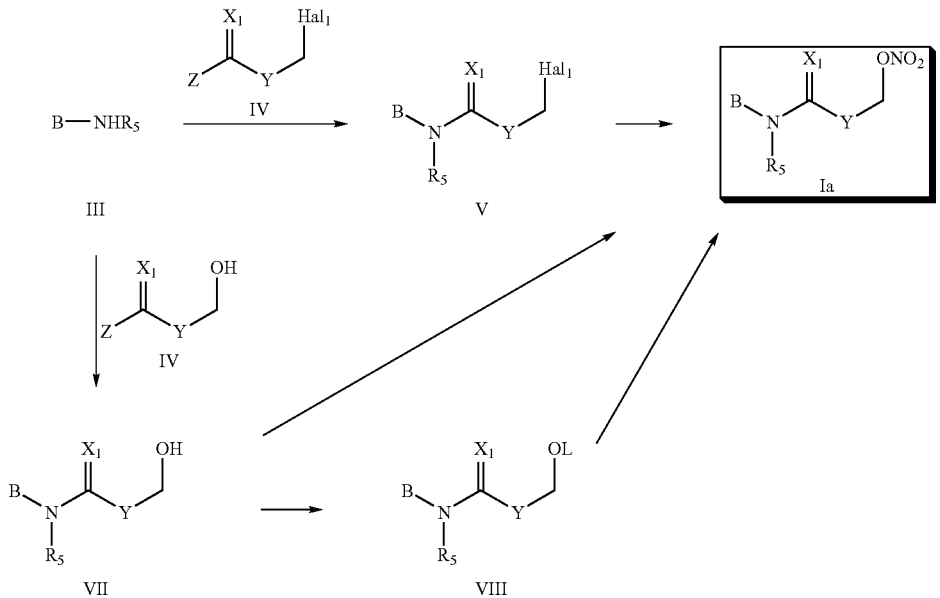

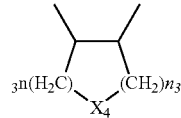

wherein $n_3$ is an integer of 0 or 1, and $X_4$ is a hetero atom of S or O; $Y_4$ is represented by the following formula of a $C_2$ to $C_4$ heterocyclic ring:

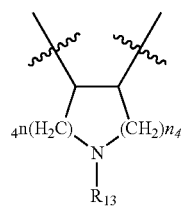

wherein $n_4$ is an integer of 0 or 1, and $R_{13}$ is hydrogen, a $C_1$ to $C_5$ alkyl or $NHCOR_{14}$, $R_{14}$ is hydrogen or a $C_1$ to $C_5$ alkyl; and $Y_5$ is a $C_2$ to $C_{10}$ straight chain or branched alkyl or alkene having 1 to 3 double bonds.

In accordance with another aspect of the present invention, there is provided a pharmaceutical composition containing the colchicine derivatives represented by the formulas (I) or (II) and pharmaceutically acceptable salts thereof as effective components, the pharmaceutical composition having anti-cancer, anti-proliferative and anti-inflammatory effects and immunosuppressive and muscle-relaxing functions.

wherein, B in the formula is represented by the formula C1 or C2:

wherein $R_2$, $R_3$, and $R_4$ and X are defined as the above in the compounds of the formulas (I) and (II).

In the reaction scheme 1, $R_5$ is hydrogen or a lower alkyl; $X_1$ is O or S; $Hal_1$ is halogen; Z in the (IV) and (VI) may be the same or different and represents OH or halogen; L is a leaving group selected from methanesulfonyl, p-toluenesulfonyl and triflate; and Y is selected from the formula (a'), (b'), (c'), (d') (e'), (f') and (g'):

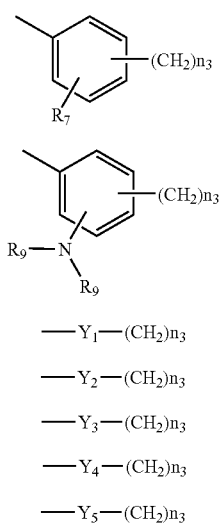

(a')
(b')
—Y₁—(CH₂)n₃  (c')
—Y₂—(CH₂)n₃  (d')
—Y₃—(CH₂)n₃  (e')
—Y₄—(CH₂)n₃  (f')
—Y₅—(CH₂)n₃  (g')

wherein, $Y_1$ through $Y_5$ and $R_7$ through $R_9$ are independently the same as defined in the formula (I) and (II), and $n_3$ is an integer of 0 to 2.

The present invention will now be described in more detail.

Throughout the specification, a lower alkyl represents a $C_1$ to $C_6$, preferably, $C_1$ to $C_4$ straight chain or branched hydrocarbon.

Preferred examples of the colchicine derivatives of the formulas (I) or (II) according to the present invention include:

2-Fluoro-3-nitrooxymethyl-N-(1,2,3-trimethoxy-10-methylsulfanyl-9-oxo-5,6,7,9-tetrahydro-benzo[α]heptalen-7-yl)-benzamide;
2-Fluoro-5-bromomethyl-N-(1,2,3-trimethoxy-10-methylsulfanyl-9-oxo-5,6,7,9-tetrahydro-benzo[α]heptalen-7-yl)-benzamide;
2-Chloro-3-nitrooxymethyl-N-(1,2,3-trimethoxy-10-methylsulfanyl-9-oxo-5,6,7,9-tetrahydro-benzo[α]heptalen-7-yl)-benzamide;
2-Chloro-5-chloromethyl-N-(1,2,3-trimethoxy-10-methylsulfanyl-9-oxo-5,6,7,9-tetrahydro-benzo[α]heptalen-7-yl)-benzamide;
2-Iodo-3-nitrooxymethyl-N-(1,2,3-trimethoxy-10-methylsulfanyl-9-oxo-5,6,7,9-tetrahydro-benzo[α]heptalen-7-yl)-benzamide;
2-Cyano-3-nitrooxymethyl-N-(1,2,3-trimethoxy-10-methylsulfanyl-9-oxo-5,6,7,9-tetrahydro-benzo[α]heptalen-7-yl)-benzamide;
2-Bromo-3-nitrooxymethyl-N-(1,2,3-trimethoxy-10-methylsulfanyl-9-oxo-5,6,7,9-tetrahydro-benzo[α]heptalen-7-yl)-benzamide;
2-Phenyl-3-nitrooxymethyl-N-(1,2,3-trimethoxy-10-methylsulfanyl-9-oxo-5,6,7,9-tetrahydro-benzo[α]heptalen-7-yl)-benzamide;
2-Iodo-3-methyl-N-(1,2,3-trimethoxy-10-methylsulfanyl-9-oxo-5,6,7,9-tetrahydro-benzo[α]heptalen-7-yl)-benzamide;
2-Chloro-3-methyl-N-(1,2,3-trimethoxy-10-methylsulfanyl-9-oxo-5,6,7,9-tetrahydro-benzo[α]heptalen-7-yl)-benzamide;
2-Cyano-3-methyl-N-(1,2,3-trimethoxy-10-methylsulfanyl-9-oxo-5,6,7,9-tetrahydro-benzo[α]heptalen-7-yl)-benzamide;
2-Fluoro-5-methyl-N-(1,2,3-trimethoxy-10-methylsulfanyl-9-oxo-5,6,7,9-tetrahydro-benzo[α]heptalen-7-yl)-benzamide;
3-Methyl-N-(1,2,3-trimethoxy-10-methylsulfanyl-9-oxo-5,6,7,9-tetrahydro-benzo[α]heptalen-7-yl)-benzamide;
2-Nitro-3-nitrooxymethyl-N-(1,2,3-trimethoxy-10-methylsulfanyl-9-oxo-5,6,7,9-tetrahydro-benzo[α]heptalen-7-yl)-benzamide;
3-Methyl-5-nitrooxymethyl-N-(1,2,3-trimethoxy-10-methylsulfanyl-9-oxo-5,6,7,9-tetrahydro-benzo[α]heptalen-7-yl)-benzamide;
2-Methoxy-5-nitrooxymethyl-N-(1,2,3-trimethoxy-10-methylsulfanyl-9-oxo-5,6,7,9-tetrahydro-benzo[α]heptalen-7-yl)-benzamide;
3-Dimethylamino-N-(1,2,3-trimethoxy-10-methylsulfanyl-9-oxo-5,6,7,9-tetrahydro-benzo[α]heptalen-7-yl)-benzamide;
2-(2-Mercapto-4-methyl-thiazol-5-yl)-N-(1,2,3-trimethoxy-10-methylsulfanyl-9-oxo-5,6,7,9-tetrahydro-benzo[α]heptalen-7-yl)-acetamide;
2-(2-Thionitrite-4-methyl-thiazol-5-yl)-N-(1,2,3-trimethoxy-10-methylsulfanyl-9-oxo-5,6,7,9-tetrahydro-benzo[α]heptalen-7-yl)-acetamide;
2-(2,5-Dioxo-imidazolidin-4-yl)-N-(1,2,3-trimethoxy-10-methylsulfanyl-9-oxo-5,6,7,9-tetrahydro-benzo[α]heptalen-7-yl)-acetamide;
6-Methyl-pyrimidine-4-carboxylic acid (1,2,3-trimethoxy-10-methylsulfanyl-9-oxo-5,6,7,9-tetrahydro-benzo[α]heptalen-7-yl)-amide;
6-Bromomethyl-pyrimidine-4-carboxylic acid (1,2,3-trimethoxy-10-methylsulfanyl-9-oxo-5,6,7,9-tetrahydro-benzo[α]heptalen-7-yl)-amide;
6-Nitrooxymethyl-pyridine-2-carboxylic acid (1,2,3-trimethoxy-10-methylsulfanyl-9-oxo-5,6,7,9-tetrahydro-benzo[α]heptalen-7-yl)-amide;
5-Nitrooxymethyl-thiophene-2-carboxylic acid (1,2,3-trimethoxy-10-methylsulfanyl-9-oxo-5,6,7,9-tetrahydro-benzo[α]heptalen-7-yl)-amide;
2-Methyl-cyclopropanecarboxylic acid (1,2,3-trimethoxy-10-methylsulfanyl-9-oxo-5,6,7,9-tetrahydro-benzo[α]heptalen-7-yl)-amide;
2-Methyl-cyclopropanecarboxylic acid (10-methanesulfinyl-1,2,3-trimethoxy-10-methylsulfanyl-9-oxo-5,6,7,9-tetrahydro-benzo[α]heptalen-7-yl)-amide;
2-Methyl-cyclopropanecarboxylic acid (10-methanesulfonyl-1,2,3-trimethoxy-10-methylsulfanyl-9-oxo-5,6,7,9-tetrahydro-benzo[α]heptalen-7-yl)-amide;
2-Methyl-cyclopropanecarboxylic acid (1,2,3-trimethoxy-10-methylsulfanyl-9-thioxo-5,6,7,9-tetrahydro-benzo[α]heptalen-7-yl)-amide;
2-Methyl-cyclopropanecarboxylic acid (1,2,3-trimethoxy-9-oxo-5,6,7,9-tetrahydro-benzo[α]heptalen-7-yl)-amide;
2-Methyl-cyclopropanecarboxylic acid (1,2,3-trimethoxy-10-methylsulfanyl-9-oxo-5,6,7,9-tetrahydro-benzo[α]heptalen-7-yl)-amide;
2-Methyl-cyclopropanecarboxylic acid (1-hydroxy-2,3-dimethoxy-10-methylsulfanyl-9-oxo-5,6,7,9-tetrahydro-benzo[α]heptalen-7-yl)-amide;
2-Methyl-cyclopropanecarboxylic acid (2-hydroxy-1,3-dimethoxy-10-methylsulfanyl-9-oxo-5,6,7,9-tetrahydro-benzo[α]heptalen-7-yl)-amide;
3-Methyl-aziridine-2-carboxylic acid (1,2,3-trimethoxy-10-methylsulfanyl-9-oxo-5,6,7,9-tetrahydro-benzo[α]heptalen-7-yl)-amide;
1,3-Dimethyl-aziridine-2-carboxylic acid (1,2,3-trimethoxy-10-methylsulfanyl-9-oxo-5,6,7,9-tetrahydro-benzo[α]heptalen-7-yl)-amide;

But-2-enoic acid (1,2,3-trimethoxy-10-methylsulfanyl-9-oxo-5,6,7,9-tetrahydro-benzo[α]heptalen-7-yl)-amide;
But-2-enoic acid (10-methanesulfonyl-1,2,3-trimethoxy-9-oxo-5,6,7,9-tetrahydro-benzo[α]heptalen-7-yl)-amide;
Pent-3-enoic acid (1,2,3-trimethoxy-10-methylsulfanyl-9-oxo-5,6,7,9-tetrahydro-benzo[α]heptalen-7-yl)-amide;
But-3-enoic acid (1,2,3-trimethoxy-10-methylsulfanyl-9-oxo-5,6,7,9-tetrahydro-benzo[α]heptalen-7-yl)-amide;
Hexa-2,4-dienoic acid (1,2,3-trimethoxy-10-methylsulfanyl-9-oxo-5,6,7,9-tetrahydro-benzo[α]heptalen-7-yl)-amide;
2-Chloro-3-methyl-N-(3,9,10,11-tetramethoxy-6,7-dihydro-5H-dibenzo[a,c]cyclohepten-5-yl)-benzamide;
2-Methyl-cyclopropanecarboxylic acid (3,9,10,11-tetramethoxy-6,7-dihydro-5H-dibenzo[a,c]cyclohepten-5-yl)-amide;
2-Chloro-N-(3-methanesulfonyl-9,10,11-trimethoxy-6,7-dihydro-5H-dibenzo[a,c]cyclohepten-5-yl)-3-methyl-benzamide;
2-Methyl-cyclopropanecarboxylic acid (3-methanesulfonyl-9,10,11-trimethoxy-6,7-dihydro-5H-dibenzo[a,c]cyclohepten-5-yl)-amide;
But-2-enoic acid (3-methanesulfonyl-9,10,11-trimethoxy-6,7-dihydro-5H-dibenzo[a,c]cyclohepten-5-yl)-amide;
2-Chloro-3-methyl-N-(1,2,3-trimethoxy-10-methylsulfanyl-9-thioxo-5,6,7,9-tetrahydro-benzo[α]heptalen-7-yl)-benzamide;
2-Fluoro-5-nitrooxymethyl-N-(1,2,3-trimethoxy-10-methylsulfanyl-9-oxo-5,6,7,9-tetrahydro-benzo[α]heptalen-7-yl)-benzamide;
4-Fluoro-3-nitrooxymethyl-N-(1,2,3-trimethoxy-10-methylsulfanyl-9-oxo-5,6,7,9-tetrahydro-benzo[α]heptalen-7-yl)-benzamide;
2-Chloro-5-methyl-N-(1,2,3-trimethoxy-10-methylsulfanyl-9-oxo-5,6,7,9-tetrahydro-benzo[α]heptalen-7-yl)-benzamide;
2-Chloro-5-nitrooxymethyl-N-(1,2,3-trimethoxy-10-methylsulfanyl-9-oxo-5,6,7,9-tetrahydro-benzo[α]heptalen-7-yl)-benzamide;
4-Chloro-3-nitrooxymethyl-N-(1,2,3-trimethoxy-10-methylsulfanyl-9-oxo-5,6,7,9-tetrahydro-benzo[α]heptalen-7-yl)-benzamide;
2-Bromo-5-nitrooxymethyl-N-(1,2,3-trimethoxy-10-methylsulfanyl-9-oxo-5,6,7,9-tetrahydro-benzo[α]heptalen-7-yl)-benzamide;
4-Bromo-3-nitrooxymethyl-N-(1,2,3-trimethoxy-10-methylsulfanyl-9-oxo-5,6,7,9-tetrahydro-benzo[α]heptalen-7-yl)-benzamide;
2-Iodo-5-nitrooxymethyl-N-(1,2,3-trimethoxy-10-methylsulfanyl-9-oxo-5,6,7,9-tetrahydro-benzo[α]heptalen-7-yl)-benzamide;
4-Iodo-3-nitrooxymethyl-N-(1,2,3-trimethoxy-10-methylsulfanyl-9-oxo-5,6,7,9-tetrahydro-benzo[α]heptalen-7-yl)-benzamide;
2-Nitro-5-nitrooxymethyl-N-(1,2,3-trimethoxy-10-methylsulfanyl-9-oxo-5,6,7,9-tetrahydro-benzo[α]heptalen-7-yl)-benzamide;
4-Nitro-3-nitrooxymethyl-N-(1,2,3-trimethoxy-10-methylsulfanyl-9-oxo-5,6,7,9-tetrahydro-benzo[α]heptalen-7-yl)-benzamide;
2-Cyano-5-nitrooxymethyl-N-(1,2,3-trimethoxy-10-methylsulfanyl-9-oxo-5,6,7,9-tetrahydro-benzo[α]heptalen-7-yl)-benzamide;
4-Cyano-3-nitrooxymethyl-N-(1,2,3-trimethoxy-10-methylsulfanyl-9-oxo-5,6,7,9-tetrahydro-benzo[α]heptalen-7-yl)-benzamide;
4-Nitrooxymethyl-biphenyl-2-carboxylic acid (1,2,3-trimethoxy-10-methylsulfanyl-9-oxo-5,6,7,9-tetrahydro-benzo[α]heptalen-7-yl)-amide;
2-Nitrooxymethyl-biphenyl-4-carboxylic acid (1,2,3-trimethoxy-10-methylsulfanyl-9-oxo-5,6,7,9-tetrahydro-benzo[α]heptalen-7-yl)-amide;
2-Methoxy-3-nitrooxymethyl-N-(1,2,3-trimethoxy-10-methylsulfanyl-9-oxo-5,6,7,9-tetrahydro-benzo[α]heptalen-7-yl)-benzamide;
4-Methoxy-3-nitrooxymethyl-N-(1,2,3-trimethoxy-10-methylsulfanyl-9-oxo-5,6,7,9-tetrahydro-benzo[α]heptalen-7-yl)-benzamide;
[4-Nitrooxymethyl-2-(1,2,3-trimethoxy-10-methylsulfanyl-9-oxo-5,6,7,9-tetrahydro-benzo[α]heptalen-7-ylcarbamoyl)-phenyl]-carbamic acid tert-butyl ester;
4-Dimethylamino-N-(1,2,3-trimethoxy-10-methylsulfanyl-9-oxo-5,6,7,9-tetrahydro-benzo[α]heptalen-7-yl)-benzamide;
4-Aminomethyl-N-(1,2,3-trimethoxy-10-methylsulfanyl-9-oxo-5,6,7,9-tetrahydro-benzo[α]heptalen-7-yl)-benzamide;
2-Methyl-5-nitrooxymethyl-2H-pyrazole-3-carboxylic acid (1,2,3-trimethoxy-10-methylsulfanyl-9-oxo-5,6,7,9-tetrahydro-benzo[α]heptalen-7-yl)-amide;
2-(5-Methyl-2,4-dioxo-3,4-dihydro-2H-pyrimidin-1-yl)-N-(1,2,3-trimethoxy-10-methylsulfanyl-9-oxo-5,6,7,9-tetrahydro-benzo[α]heptalen-7-yl)-acetamide;
2-Methyl-cyclopropanecarboxylic acid (1,2,3-trimethoxy-9-oxo-5,6,7,8,9,10,11,12-octahydro-benzo[α]heptalen-7-yl)-amide;
N-(1,2,3-Trimethoxy-9-oxo-5,6,7,9-tetrahydro-benzo[α]heptalen-7-yl)-acetamide;
2-Methyl-cyclopropanecarboxylic acid (1,2,3-trimethoxy-5,6,7,8,9,10,11,12-octahydro-benzo[α]heptalen-7-yl)-amide;
2-Methyl-cyclopropanecarboxylic acid (1,2,3,10-tetramethoxy-9-oxo-5,6,7,9-tetrahydro-benzo[α]heptalen-7-yl)-amide;
2-Methyl-cyclopropanecarboxylic acid (1-hydroxy-10-methane sulfinyl-2,3-dimethoxy-9-oxo-5,6,7,9-tetrahydro-benzo[α]heptalen-7-yl)-amide;
2-Methyl-cyclopropanecarboxylic acid (1-hydroxy-10-methanesulfonyl-2,3-dimethoxy-9-oxo-5,6,7,9-tetrahydro-benzo[α]heptalen-7-yl)-amide;
But-2-enoic acid (1-hydroxy-2,3-dimethoxy-10-methylsulfanyl-9-oxo-5,6,7,9-tetrahydro-benzo[α]heptalen-7-yl)-amide;
But-2-enoic acid (1-hydroxy-10-methanesulfinyl-2,3-dimethoxy-9-oxo-5,6,7,9-tetrahydro-benzo[α]heptalen-7-yl)-amide;
But-2-enoic acid (1-hydroxy-10-methanesulfonyl-2,3-dimethoxy-9-oxo-5,6,7,9-tetrahydro-benzo[α]heptalen-7-yl)-amide;
4-Methoxy-but-2-enoic acid (1,2,3-trimethoxy-10-methylsulfanyl-9-oxo-5,6,7,9-tetrahydro-benzo[α]heptalen-7-yl)-amide;
But-2-enoic acid (2-hydroxy-1,3-dimethoxy-10-methylsulfanyl-9-oxo-5,6,7,9-tetrahydro-benzo[α]heptalen-7-yl)-amide;
But-2-enoic acid (2-hydroxy-10-methylsulfinyl-1,3-dimethoxy-9-oxo-5,6,7,9-tetrahydro-benzo[α]heptalen-7-yl)-amide;
2-Ethyl-N-(1,2,3-trimethoxy-10-methylsulfanyl-9-oxo-5,6,7,9-tetrahydro-benzo[α]heptalen-7-yl)-acrylamide;
2-Ethyl-N-(10-methanesulfinyl-1,2,3-trimethoxy-9-oxo-5,6,7,9-tetrahydro-benzo[α]heptalen-7-yl)-acrylamide;

2-Methylene-but-3-enoic acid (1,2,3-trimethoxy-10-methyl-sulfanyl-9-oxo-5,6,7,9-tetrahydro-benzo[α]heptalen-7-yl)-amide;

Hexa-2,4-dienoic acid (1,2,3-trimethoxy-10-methylsulfanyl-9-oxo-5,6,7,9-tetrahydro-benzo[α]heptalen-7-yl)-amide; and 2-Ethyl-4-methyl-penta-2,4-dienoic acid (1,2,3-trimethoxy-10-methylsulfanyl-9-oxo-5,6,7,9-tetrahydro-benzo[α]heptalen-7-yl)-amide.

Examples of the pharmaceutically acceptable salt of the colchicine derivative of the formulas (I) and (II) include, but are not limited to, salts with inorganic bases such as sodium, potassium, magnesium or calcium and salts with organic bases such as ammonium, lysine, ethanolamine, N,N'-dibenzylethylenediamine and angelic acid.

Methods for preparing the colchicines derivatives according to the present invention will now be described in more detail.

In Method 1 for preparing a compound of the formula (Ia), first, a compound of the formula (III) is reacted with a compound of the formula (IV) to produce a compound (V). If Z is halogen, the reaction can be carried out without using a base, but is generally carried out in the presence of a base used for amidation. Preferred examples of the base include pyridine, triethylamine, diethylisopropylamine and dimethylphenylamine, and a phase transfer catalyst such as sodium hydrocarbonate or benzyltriethylammonium chloride. The reaction can be carried out without using a solvent, but is advantageously carried out in the presence of a solvent that does not adversely affect the reaction. Examples of the solvent used include dichloromethane, chloroform, tetrahydrofuran, diethylether, toluene and dimethylformamide. The reaction temperature is not specifically limited and is generally carried out at reduced or elevated temperature, preferably at room temperature. On the other hand, if Z is OH, a condensation reaction using an activating reagent that activates OH in carboxylic acid diimides (this can be used for amide synthesis by the reaction of carboxylic acid with amine) is used. The amidation resulted from the condensation reaction can be carried out without using a base, but is generally carried out in the presence of a base that can be used with a carboxylic acid activating reagent, such as, 1-(3-dimethylaminopropyl)-3-ethylcarboimide (EDCI), 1-hydroxybenzotriazol (HOBT), 1,3-dicyclohexylcarboimide (DCC), 2-ethoxy-1-ethoxycarbonyl-1,2-dihydroquinoline (EEDQ), and the like. Preferred examples of the base include pyridine, triethylamine, diethylisopropylamine and dimethylphenylamine, and a phase transfer catalyst such as sodium hydrocarbonate or benzyltriethylammonium chloride. The reaction can be carried out without using a solvent, but is advantageously carried out in the presence of a solvent that does not adversely affect the reaction. Examples of the solvent used include dichloromethane, chloroform, tetrahydrofuran, diethylether, toluene and dimethylformamide. The reaction temperature is not specifically limited and is generally carried out at reduced or elevated temperature, preferably at room temperature.

Second, the compound of the formula (V) is subjected to nitration to convert it into a compound of the formula (Ia). Compounds capable of nitrating halogen are generally used for the reaction, and examples of such compounds include $AgNO_3$ and t-butylammonium nitrate ($Bu_4NNO_3$). The reaction is preferably carried out in the presence of a solvent that does not adversely affect the reaction, and examples of such solvent include chloroform, acetonitrile, a mixed solution of acetonitrile and water, dichloromethane, and the like. The reaction temperature is not specifically limited and is generally carried out at reduced or elevated temperature, preferably at room temperature.

Alternatively, the compound of the formula (Ia) can be synthesized by reacting the compound of the formula (III) with a compound of the formula (VI) to produce a compound (VII), followed by converting it into the compound (Ia). The conditions for a reaction between the compound of the formula (III) and the compound of the formula (VI) are the same as those for amidation reaction between the compound of the formula (III) and the compound of the formula (IV). In order to convert the compound (VII) into the compound of the formula (Ia), the reaction is generally carried out under nitrating conditions of alcohol. Preferably, nitric acid and sulfuric acid, dinitrogen pentaoxide ($N_2O_5$) and aluminum chloride III, potassium nitrate and boron trifluoride ($BF_3$), acetylnitrate, etc., may be used, most preferably nitric acid and acetic anhydride ($Ac_2O$) are used. The reaction is preferably carried out in the presence of a solvent that does not adversely affect the reaction, and examples of the solvent used include chloroform, dichloromethane, and the like. The reaction temperature is not specifically limited and is generally carried out at reduced or elevated temperature, preferably at room temperature.

The compound of the formula (Ia) can also be synthesized by performing nitration on a compound of the formula (VIII) prepared by converting hydrogen of alcohol in the compound of the formula (VII) into a leaving group such as methane sulfonyl, p-toluene sulfonyl or triflate. In order to convert the compound (VIII) into the compound of the formula (Ia), the reaction is generally carried out under nitrating conditions. Most preferably, t-butylammonium nitrate ($Bu_4NNO_3$), t-butylammonium nitrate ($Bu_4NNO_3$) and sodium nitrate, nitric acid and silver nitrate, or potassium nitrate is used. The reaction is preferably carried out in the presence of a solvent that does not adversely affect the reaction. Examples of the solvent used include chloroform, dichloromethane, a mixed solution of benzene and water, acetonitrile, ethylalcohol, and the like. The reaction temperature is not specifically limited and is generally carried out at reduced or elevated temperature, preferably at room temperature.

Desired products can be isolated and purified by known methods, for example, column chromatography or recrystallization.

As another aspect, the present invention relates to a pharmaceutical composition comprising a colchicine derivative or its pharmaceutically acceptable salt according to the present invention as an active ingredient.

As another aspect, the present invention relates to a method for providing an immuno-suppressive or immuno-modulating effect, an anti-inflammatory effect, an anti-proliferative effect, or for treating cancer administering to a patient in need of such an effect a pharmaceutical composition comprising an effective amount of one or more colchicine derivatives according to the present invention.

The pharmaceutical composition according to the present invention including one or more colchicine derivatives of the formulas (I) and (II), and its pharmaceutically acceptable salt as effective components can be used for gout treatment agents, anticancer agents, anti-proliferative agents, anti-inflammatory agents, immunosuppressive agents and muscle relaxing agents.

In detail, the pharmaceutical composition comprising one or more colchicine derivatives or its pharmaceutically acceptable salt according to the present invention as effective components suppresses the toxicity and growth of cells that proliferate in response to an external stimulus. In effect, it exerts cytotoxic effect equal to or stronger than cyclosporine A, the immunosuppressive agent.

The pharmaceutical composition according to the present invention showed a marked cytotoxic effect when the degree of inhibition of cell proliferation was tested. For the test, a responding cell (BALB/c mouse spleen) and a stimulating cell (DBA/2 mouse spleen) were cultured simultaneously to induce an antigen-antibody reaction (or immunoreaction) allowing cell proliferation, and the proliferated cells were treated with a candidate substance of the immunosuppressive agent, followed by the proliferation inhibition test.

The pharmaceutical composition according to the present invention showed a marked cytotoxic effect on B cells and T cells. For the test, the responding cell (BALB/c mouse spleen) was treated with an immunosuppressive candidate material, lipopolysaccharide (LPS) (B cell activator), and concanvalin A (ConA) (T cell activator) to induce B cells and T cells, and proliferation of cells was checked.

The pharmaceutical composition according to the present invention exerted a marked immunosuppressive effect at a skin graft test. For the test, a tail tissue of a donor mouse (BALB/c, H-$2^d$) is grafted onto the chest of a recipient mouse (C57BL/6, H-$2^b$) using the tail-skin grafts method. It turned out the survival rate of grated skin was equal to or higher than the existing immunosuppressive agent.

The pharmaceutical composition according to the present invention suppresses inflammatory cytokines and NO generation when used in the culture medium of macrophage and osteoblast extracted from mice (6-8 weeks, BALB/c mice).

The pharmaceutical composition according to the present invention substantially reduced collagen-induced inflammation when it was used for treatment of DBA/1J mice suffering from arthritis induced by collagen.

Therefore, the above-described tests prove that the pharmaceutical composition according to the present invention comprising one or more colchicine derivatives of the formulas (I) and (II) and its pharmaceutically acceptable salt as effective components can be advantageously used as immunosuppressive agents, immunomodulating agents, anti-proliferative agents, anti-inflammatory agents and anticancer agents.

The pharmaceutical composition according to the present invention can be prepared in various parenterally or orally administrable formulations. Typical examples of formulation for parenteral administration preferably include in the form of an isotonic aqueous saline solution or suspension for injection. Examples of formulations for oral administration include tablets, capsules and the like, which may further contain a diluent (e.g.: lactose, dextrose, sucrose, mannitol, sorbitol, cellulose and/or glycine) or a lubricant (e.g.: silica, talc, stearic acid and its magnesium or potassium salt, and/or polyethylene glycol) in addition to effective components. Tablets can further be prepared with a binder such as magnesium aluminum silicate, starch paste, gelatins, tragacanth, methylcellulose, sodium carboxymethylcellulose and/or polyvinylpyrrolidine. In some cases, there may be further contained an disintegrator such as starch, agar, and alginate or sodium salts thereof, boiling mixtures and/or absorbents, a coloring agent, a flavoring agent, or a sweetener. The formulations can be prepared by known techniques of mixing, granulation or coating.

The pharmaceutical composition according to the present invention is sterilized and/or contains additives such as an antiseptic, a stabilizer, a hydrator or emulsifier, osmosis adjusting salts and/or a buffering agent, and other therapeutically effective materials. These preparations can be formulated in accordance with known methods typically employed in the formulation process.

As the effective components of the pharmaceutical composition of the present invention, the colchicine derivative of the formula (I) and its pharmaceutically acceptable salt can be administered to mammals including humans through parenteral or oral routes in an amount of 1 to 200 mg/kg (body weight) once or several times per day.

EXAMPLES

The present invention will be further described by the following Examples. It is also to be understood that the Examples are for illustrative purposes only and are not intended to be limiting.

The preparation of 7-deacetylcolchicine used in Examples was carried out in accordance with the method described in EP 0493064, Synthetic Communications 1997, 27(2), pp 293-296.

The preparation of (−)-thiodeacetylcolchicine was carried out in accordance with the method described in WO 9421598, Bioorganic & Medicinal Chemistry, Vol 5, No. 12, pp 2277-2282 (1997).

The preparation of (+)-deacetylcolchicine was carried out in accordance with the method described in Tetrahedron, Vol 14, pp 8-34, 1961).

The preparation of (+)-thiodeacetylcolchicine was carried out in accordance with the method described in Bioorganic & Medicinal Chemistry, Vol 5, No. 12, pp 2277-2282, 1997).

The preparation of (−)-1-demetylcolchicine was carried out in accordance with the method described in Journal of Medicinal Chemistry, Vol 33, No. 9, pp 2311-2319, 1990).

The preparation of (−)-2-demetylcolchicine was carried out in accordance with the method described in Journal of Medicinal Chemistry, Vol 33, No. 9, pp 2311-2319, 1990).

The preparation of (−)-deacetyl-9-methoxyallocolchicine was carried out in accordance with the method described in Bioorganic & Medicinal Chemistry, Vol 46, No. 11, pp 1269-1281, 2003).

Example 1

Preparation of 2-Fluoro-3-nitrooxymethyl-N-(1,2,3-trimethoxy-10-methylsulfanyl-9-oxo-5,6,7,9-tetrahydro-benzo[α]heptalen-7-yl)-benzamide

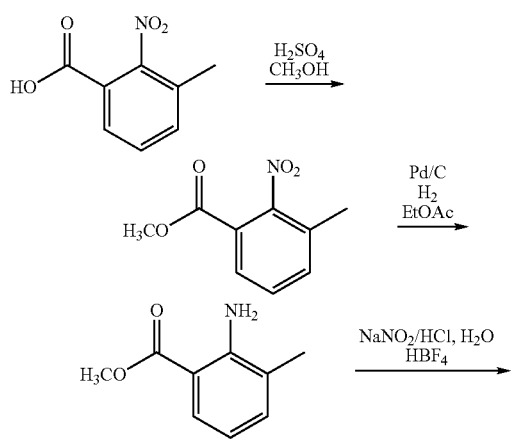

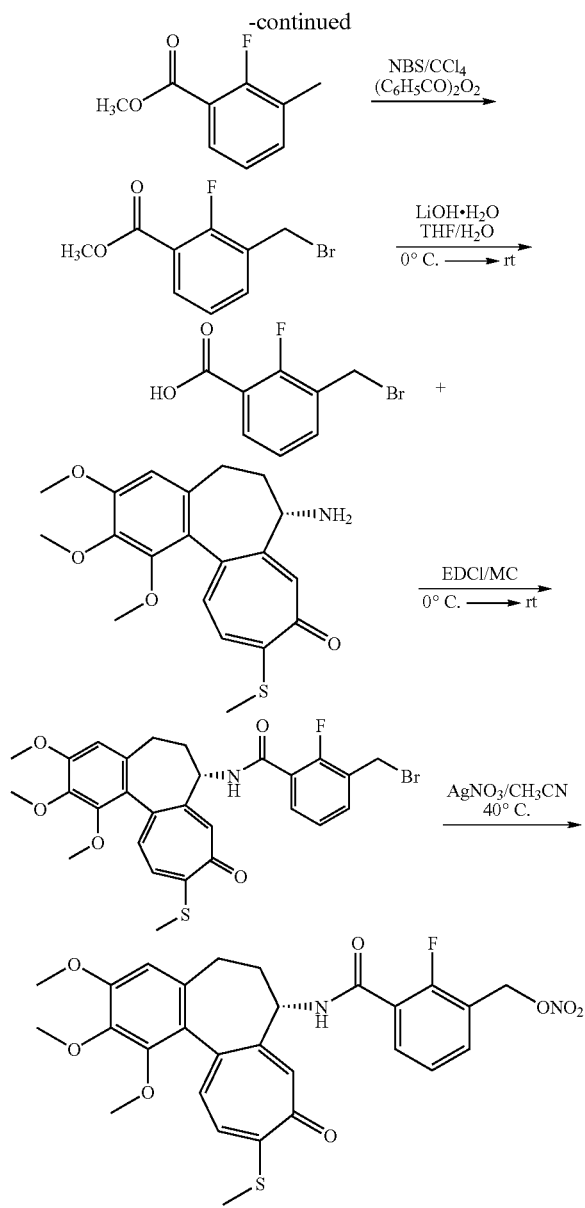

10 g (55.2 mmol) of 3-methyl-2-nitrobenzoic acid was placed into a flask and was dissolved by methanol. 7 ml of sulfuric acid was added slowly thereto and the mixture was refluxed under heating. After the reaction was completed, the mixture was concentrated under reduced pressure and then the residue was extracted with dichloromethane. The separated organic layer was dried over anhydrous magnesium sulfate, filtered and concentrated under reduced pressure to produce a pure methyl ester compound (Intermediate compound 1, 9,28 g, Yield of the first step: 86%). 9.28 g (47.5 mmol) of the intermediate compound I was placed into a flask and was dissolved by ethyl acetate. 3.09 g of 10% palladium/carbon (Pd/C) (⅓ of the sample weight) was added thereto, and the mixture was stirred under hydrogen (gas) for 1-2 days. After the reaction was completed, an excess of Pd/C was removed by filtration. And, the solvent in the mixture was concentrated under reduced pressure. The concentrated product thusly obtained was purified by the column chromatography (ethylacetate:hexane=1:20) to obtain an amino-substituted compound (Intermediate compound 2, 7.69 g, Yield of the second step: 98%). To 1 g (6.05 mmol) of the intermediate compound 2 in 3 ml of water, 1.1 ml of conc. hydrochloric acid was added and stirred. Then, 0.543 g (7.87 mmol) sodium nitrite solution in 5 ml of water was slowly added over 1 hour at a temperature range of 0° C.-5° C. The mixture was stirred for 2 hours while maintaining the reaction temperature range of 0° C.-5° C. to obtain diazonium solution. To the diazonium solution, 1.25 ml (9.08 mmol) of tetrafluoroborate 54% was added and the mixture was stirred for about 2 hours at the same reaction temperature of 0° C.-5° C. A white salt thusly produced was washed with ice water and then cold methanol, and was dried completely. The dry salt was then placed into a 25 ml flask and was heated. The mixture was cooled and extracted with ethylacetate. The separated organic layer was dried over anhydrous magnesium sulfate and filtered. The filtrate was evaporated under reduced pressure and the concentrated product was purified by the column chromatography (ethylacetate:hexane=1:20) to obtain fluoro-substituted benzoyl methyl ester (Intermediate compound 3, 204 mg, Yield of the third step: 20%). 202 mg (1.2 mmol) of the intermediate compound 3 was dissolved in 10 ml of carbon tetrachloride, and 214 mg (1.2 mmol) of N-bromosuccinimide and 87 mg (0.36 mmol) of benzoyl peroxide were added thereto. The mixture was refluxed under heating for 1 hour. After the reaction was completed, the reaction mixture was concentrated under reduced pressure and the residue was extracted through dichloromethane. The separated organic layer was dried over anhydrous magnesium sulfate, filtered and then concentrated under reduced pressure. The concentrated product was purified by the column chromatography (ethylacetate:hexane=1:10) to obtain 3-bromomethyl benzoyl methyl ester (Intermediate compound 4, 173 mg, Yield of the fourth step: 58%). 173 mg (0.7 mmol) of the intermediate compound 4 was dissolved in 5 ml of tetrahydrofuran, and 32 mg (0.77 mmol) of lithium hydroxide monohydrate solution in 2 ml of water was added at 0° C. and stirred. The temperature was raised to room temperature for the reaction. When the reaction was completed, the mixture was neutralized with acid and ethyl acetate was added thereto for extraction of an organic layer. The organic layer thusly obtained was washed with saturated brine, and dried over anhydrous magnesium sulfate. Solvent was concentrated under reduced pressure to obtain 3-bromomethyl benzoic acid (Intermediate compound 5, 131 mg, Yield of the fifth step: 80%). 126 mg (0.54 mmol) of the intermediate compound 5 and 202 mg (0.54 mmol) of (−)-thiodeacetylcolchicine were dissolved in 10 ml of dichloromethane and were stirred. To the mixture, 113 mg (0.59 mmol) of 1-(3-dimethylaminopropyl)-3-ethyl-carboimide (EDCI) was added at 0° C. and stirred for 22 hours. When the reaction was completed, the reaction mixture was concentrated under reduced pressure. The concentrated product was then purified by the column chromatography (ethylacetate:hexane=2:1) to obtain 2-fluoro-3-bromomethyl-N-(1,2,3-trimethoxy-10-methylsulfanyl-9-oxo-5,6,7,9-tetrahydro-benzo[α]heptalen-7-yl)-benzamide (Intermediate compound 6, 126 mg, Yield of the sixth step: 40%). 122 mg (0.21 mmol) of the intermediate compound 6 was dissolved in 20 ml of acetonitrile and was stirred. To the mixture, 352 mg (2.07 mmol) of silver nitrate was added and stirred for 2 days at 40° C. Silver bromide produced from the reaction was filtered with celite. The filtrate was concentrated under reduced pressure and the residue was extracted through dichloromethane and water. The organic layer was dried over anhydrous magnesium sulfate and filtered. The filtrate was evaporated under reduced pressure and the residue was then purified by the column chromatography (ethylacetate:hexane=1:1) to obtain the title product 3 (109 mg, Yield of the third step: 91%).

$^1$H NMR of the intermediate compound 1:

$^1$H NMR (300 MHz, CDCl$_3$): δ 7.78 (d, J=7.32 Hz, 1H), 7.41 (m, 2H), 3.80 (s, 3H), 2.28 (s, 3H)

$^1$H NMR of the intermediate compound 3:

$^1$H NMR (300 MHz, CDCl$_3$): δ 7.74 (dd, 1H), 7.37 (dd, 1H), 7.08 (dd, 1H), 3.93 (s, 3H), 2.31 (s, 3H)

$^1$H NMR of the intermediate compound 4:

$^1$H NMR (300 MHz, CDCl$_3$): δ 7.90 (dd, 1H), 7.59 (dd, 1H), 7.23 (dd, 1H), 4.53 (s, 2H), 3.94 (s, 3H)

$^1$H NMR of the intermediate compound 5:

$^1$H NMR (300 MHz, CDCl$_3$): δ 7.95 (dd, 1H), 7.61 (dd, 1H), 7.21 (dd, 1H), 4.55 (s, 2H)

$^1$H NMR of the intermediate compound 6:

$^1$H NMR (300 MHz, CDCl$_3$): δ 7.93~7.89 (m, 1H), 7.59~7.54 (m, 1H), 7.34~7.20 (m, 4H), 7.06 (d, J=10.44 Hz, 1H), 6.57 (s, 1H), 4.84~4.76 (m, 1H), 4.72~4.49 (AB quartet, 2H), 3.96 (s, 3H), 3.92 (s, 3H), 3.73 (s, 3H), 2.60~2.36 (m, 3H), 2.43 (s, 3H), 1.90~2.00 (m, 1H)

$^1$H NMR of the compound 1:

$^1$H NMR (300 MHz, CDCl$_3$): δ 8.00~7.96 (m, 1H), 7.60~7.56 (m, 1H), 7.34~7.24 (m, 4H), 7.06 (d, J=10.26 Hz, 1H), 6.58 (s, 1H), 5.64~5.50 (AB quartet, 2H), 4.80~4.90 (m, 1H), 3.96 (s, 3H), 3.92 (s, 3H), 3.73 (s, 3H), 2.65~2.30 (m, 3H), 2.43 (s, 3H), 1.90~2.00 (m, 1H)

Example 2

Preparation of 2-Fluoro-5-bromomethyl-N-(1,2,3-trimethoxy-10-methylsulfanyl-9-oxo-5,6,7,9-tetrahydro-benzo[α]heptalen-7-yl)-benzamide

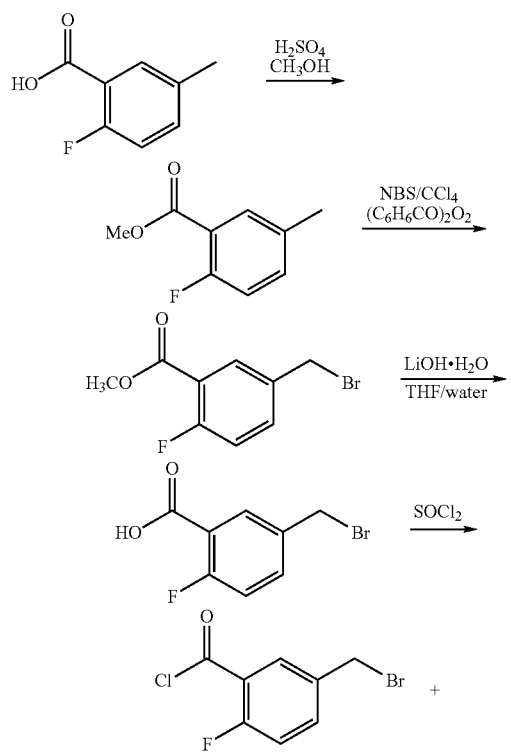

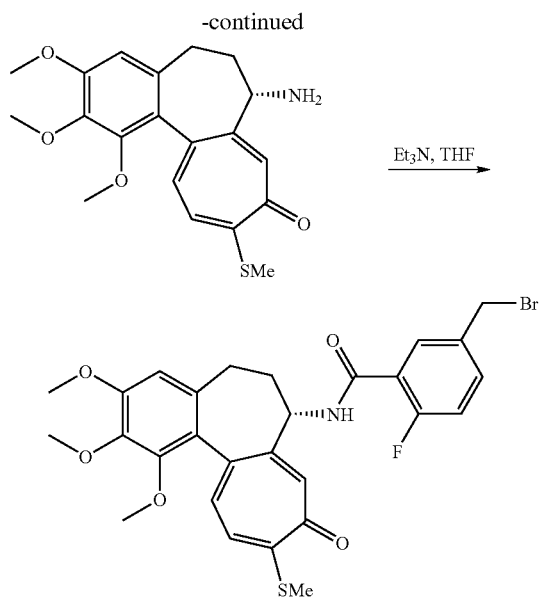

2-Fluoro-5-methyl benzoic acid was subjected to the first step in the reaction of Example 1 to obtain 2-fluoro-5-methyl benzoic acid methyl ester (Intermediate compound 7), and the second through fifth steps in the reaction were carried out in accordance with the same method with Example 3 (to be described) to obtain the title compound 2 (190 mg, Yield of the fifth step: 18%).

$^1$H NMR of the intermediate compound 7:

$^1$H NMR (300 MHz, CDCl$_3$): δ 7.73 (d, J=9.33 Hz, 1H), 7.30 (m, 1H), 7.02 (d, J=8.40 Hz, 1H), 3.92 (s, 3H), 2.35 (s, 3H)

$^1$H NMR of the compound 2:

$^1$H NMR (300 MHz, CDCl$_3$): δ 7.95 (d, J=7.32 Hz, 1H), 7.59~7.48 (m, 1H), 7.34~7.04 (m, 5H), 6.57 (s, 1H), 4.96~4.87 (m, 1H), 4.52~4.42 (m, 2H), 3.96 (s, 3H), 3.92 (s, 3H), 3.72 (s, 3H), 2.70~2.36 (m, 3H), 2.48 (s, 3H), 2.01~1.88 (m, 1H)

Example 3

Preparation of 2-Chloro-3-nitrooxymethyl-N-(1,2,3-trimethoxy-10-methylsulfanyl-9-oxo-5,6,7,9-tetrahydro-benzo[α]heptalen-7-yl)-benzamide;

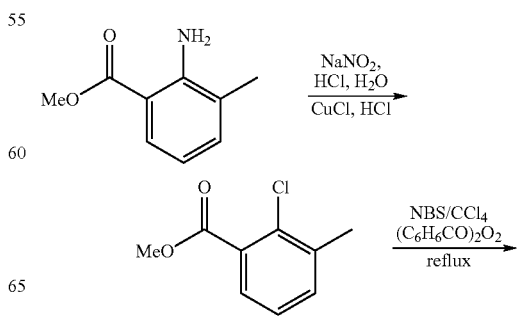

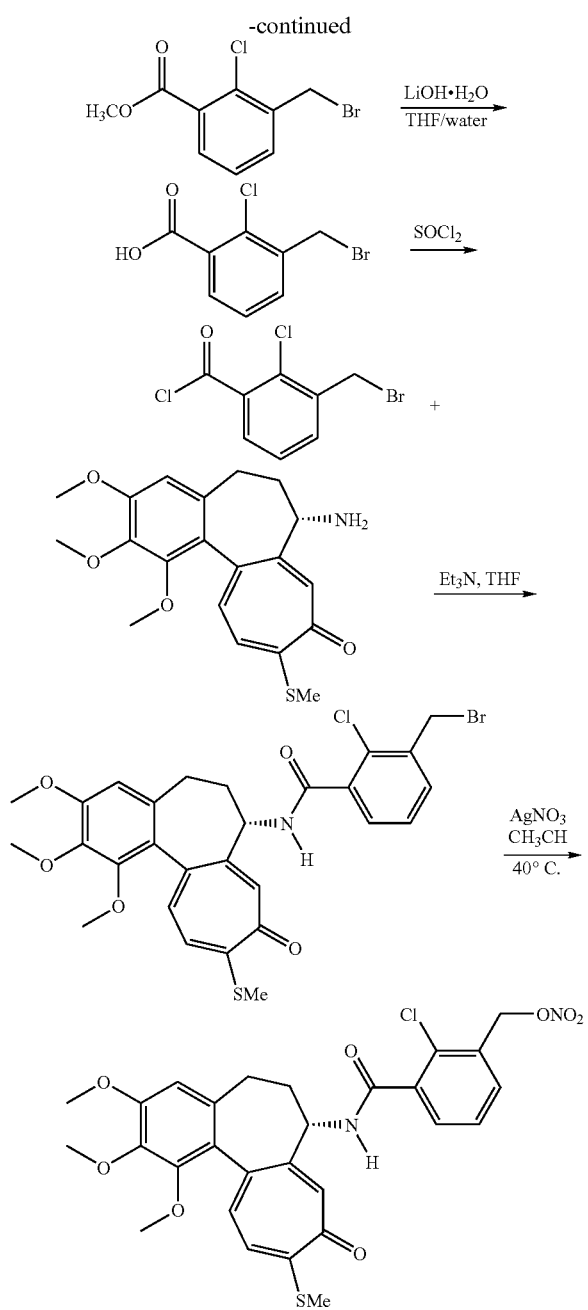

1.52 g (9.2 mmol) of 2-amino-3-methyl-benzoul methyl acetate obtained from Example 1 was added by 1.6 ml of conc. hydrochloric acid in 4 ml of water was stirred. At a temperature range of 0° C.-5° C., 0.825 g (11.96 mmol) of sodium nitrite solution in 8 ml of water was slowly added to the mixture over 20 minutes and the reaction was continued for 1 hour to obtain diazonium solution. At the same temperature range, 1.09 g (11.04 mmol) of copper chloride was mixed with 1.6 ml of conc. hydrochloric acid, and the diazonium solution was slowly added to this mixture over 40 minutes. The reaction was continued for another hour at the same temperature and for two hours at room temperature. An organic layer was extracted with ethylacetate, dried over anhydrous magnesium sulfate, filtered and concentrated under reduced pressure, and the concentrated product was purified by the column chromatography (ethylacetate:hexane=1:8) to obtain chloro-substituted benzoyl methyl ester (Intermediate compound 11, 1.18 g, Yield of the first step: 70%). Meanwhile, the fourth and fifth steps in the reaction of Example 1 were carried out to obtain 3-bromomethyl-2-chloro-benzoic acid (Intermediate compound 13, Yield of the third step: 75%) through the intermediate compound 12 (Yield of the second step: 63%). At the temperature range of 0° C.-5° C., 535 mg (2.14 mmol) of the intermediate compound 13 was mixed with 10 ml of thionylchloride. For the reaction, the temperature was raised up to 60° C., and the mixture was heated for 15 hours. Thionylchloride was then removed under reduced pressure (the fourth step). 800 mg (2.14 mmol) of (−)-thiodeacetylcolchicine was dissolved in 10 ml of tetrahydrofuran and 1.5 ml of triethylamine was added thereto. At the temperature range of 0° C.-5° C., acyl chloride solution was slowly added to the mixture. The reaction was continued for one hour at temperature of 0° C.-5° C., and for two hours at room temperature. The reaction mixture was concentrated under reduced pressure, and the residue was extracted with dichloromethane and dried over anhydrous magnesium sulfate and filtered. The filtrate was evaporated under reduced pressure, and the concentrated product was purified by the column chromatography (ethylacetate:hexane:dichloromethane=1:1:1) to obtain 2-chloro-3-bromomethyl-N-(1,2,3-trimethoxy-10-methylsulfanyl-9-oxo-5,6,7,9-tetrahydro-benzo[α]heptalen-7-yl)-benzamide (Intermediate compound 15, 776 mg, Yield of the fifth step: 60%). The seventh step in the reaction of Example 1 was carried out to obtain the title compound 3 (590 mg, Yield of the sixth step: 85%) except that the intermediate compound 15 obtained from Example 3 was used.

$^1$H NMR of the intermediate compound 11:

$^1$H NMR (300 MHz, CDCl$_3$): δ 7.57 (d, J=7.68 Hz, 1H), 7.36 (d, J=7.71 Hz, 1H), 7.20 (t, 1H), 3.93 (s, 3H), 2.43 (s, 3H)

$^1$H NMR of the intermediate compound 12:

$^1$H NMR (300 MHz, CDCl$_3$): δ 7.72 (dd, 1H), 7.58 (dd, 1H), 7.31 (dd, 1H), 4.64 (s, 2H), 3.95 (s, 3H)

$^1$H NMR of the intermediate compound 13:

$^1$H NMR (300 MHz, CDCl$_3$): δ 7.80 (dd, 1H), 7.58 (dd, 1H), 7.32 (dd, 1H), 4.66 (s, 2H)

$^1$H NMR of the intermediate compound 15:

$^1$H NMR (300 MHz, CDCl$_3$): δ 7.56~7.48 (m, 2H), 7.35~7.29 (m, 3H), 7.06 (d, J=10.62 Hz, 1H), 6.62 (d, J=6.6 Hz, 1H), 6.58 (s, 1H), 4.92~4.84 (m, 1H), 4.60 (s, 2H), 3.97 (s, 3H), 3.93 (s, 3H), 3.72 (s, 3H). 2.61~2.34 (m, 3H), 2.44 (s, 3H), 1.96~1.86 (m, 3H)

$^1$H NMR of the compound 3:

$^1$H NMR (300 MHz, CDCl$_3$): δ 7.58~7.49 (m, 2H), 7.37~7.25 (m, 3H), 7.06 (d, J=10.44 Hz, 1H), 6.70 (d, J=7.32 Hz, 1H), 6.57 (s, 1H), 5.59 (s, 2H), 4.93~4.84 (m, 1H), 3.97 (s, 3H), 3.93 (s, 3H), 3.72 (s, 3H). 2.63~2.53 (m, 3H), 2.44 (s, 3H), 2.00~1.85 (m, 1H)

Example 4

Preparation of 2-Chloro-5-chloromethyl-N-(1,2,3-trimethoxy-10-methylsulfanyl-9-oxo-5,6,7,9-tetrahydro-benzo[α]heptalen-7-yl)-benzamide

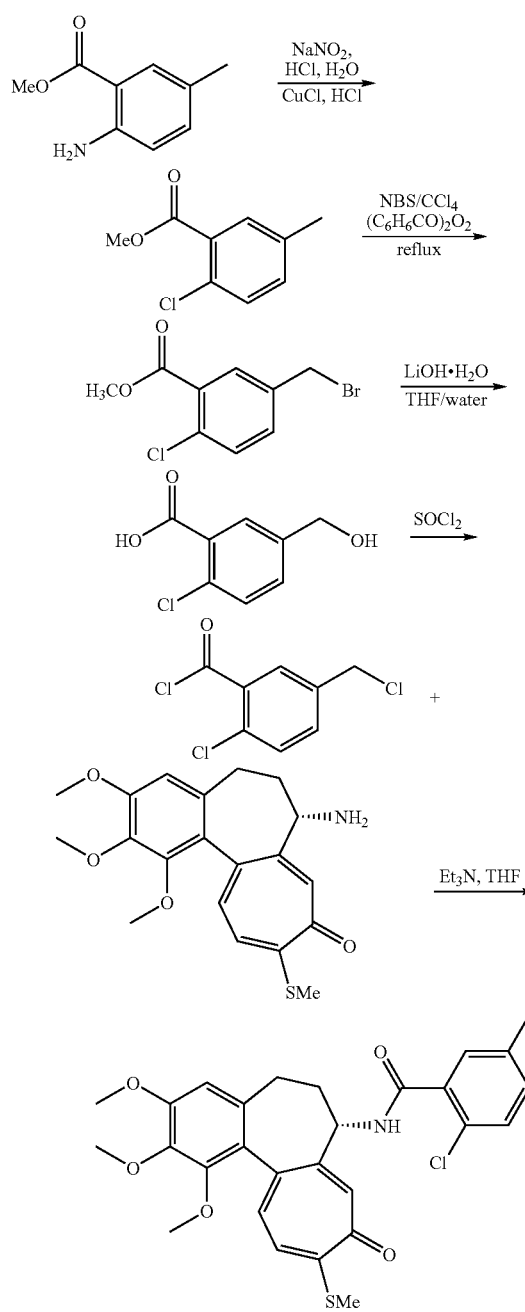

2-Amino-5-methyl benzoic acid methyl ester was subjected to the first through fifth steps in the reaction of Example 3 to obtain the title compound 4 (Yield of the fourth and fifth steps: 24%) except that 2.5 equivalence of lithium hydroxide monohydrate in the third step was used.

$^1$H NMR of the intermediate compound 16:

$^1$H NMR (300 MHz, CDCl$_3$): δ 7.63 (s, 1H), 7.31 (s, 1H), 7.22 (d, J=8.13 Hz, 1H), 3.91 (s, 3H), 2.34 (s, 3H)

$^1$H NMR of the intermediate compound 17:

$^1$H NMR (300 MHz, CDCl$_3$): δ 7.86 (s, 1H), 7.44 (s, 2H), 4.46 (s, 2H), 3.95 (s, 3H)

$^1$H NMR of the intermediate compound 18:

$^1$H NMR (300 MHz, CDCl$_3$): δ 7.86 (s, 1H), 7.43 (s, 2H), 4.65 (s, 2H), 3.40-3.38 (m, 1H)

$^1$H NMR of the compound 4:

$^1$H NMR (300 MHz, CDCl$_3$): δ 7.66 (s, 1H), 7.42~7.30 (m, 4H), 7.06 (d, J=10.26 Hz, 1H), 6.88 (d, J=6.78 Hz, 1H), 6.57 (s, 1H), 4.90~4.82 (m, 1H), 4.52 (s, 2H), 3.97 (s, 3H), 3.93 (s, 3H), 3.70 (s, 3H), 2.65~2.30 (m, 3H), 2.44 (s, 3H), 1.98~1.89 (m, 1H)

Example 5

Preparation of 2-Iodo-3-nitrooxymethyl-N-(1,2,3-trimethoxy-10-methylsulfanyl-9-oxo-5,6,7,9-tetrahydro-benzo[α]heptalen-7-yl)-benzamide

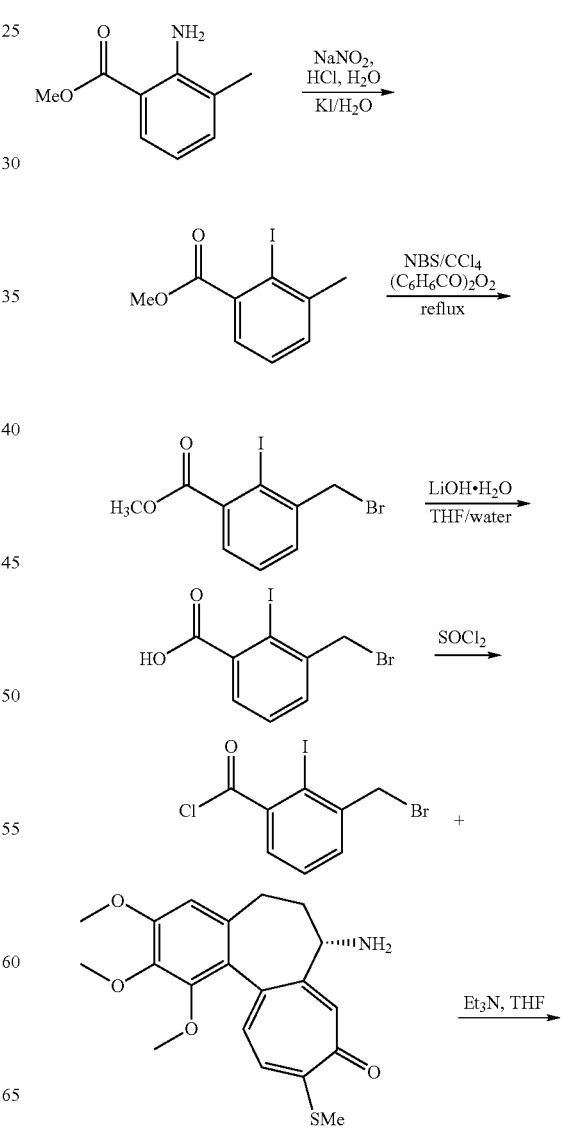

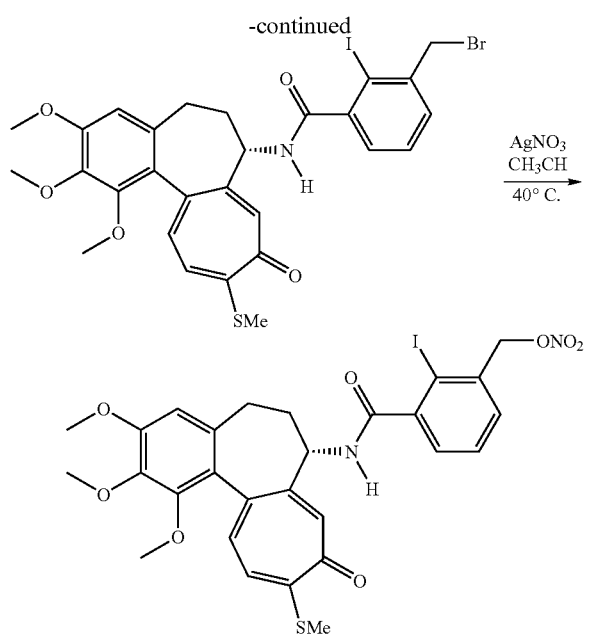

2H), 4.92~4.84 (m, 1H), 3.97 (s, 3H), 3.93 (s, 3H), 3.73 (s, 3H). 2.64~2.36 (m, 3H), 2.44 (s, 3H), 1.95~1.82 (m, 1H)

Example 6

Preparation of 2-Cyano-3-nitrooxymethyl-N-(1,2,3-trimethoxy-10-methylsulfanyl-9-oxo-5,6,7,9-tetrahydro-benzo[α]heptalen-7-yl)-benzamide

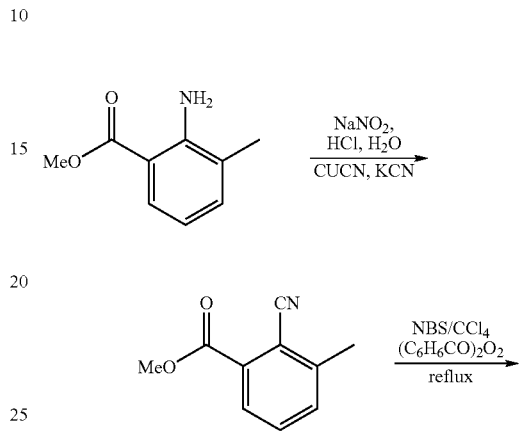

1 g (6.05 mmol) of 2-amino-3-methyl-benzoul methyl acetate obtained from Example 1 was added by 1.1 ml of conc. hydrochloric acid in 4 ml of water and stirred. At a temperature range of 0° C.-5° C., 0.543 g (7.87 mmol) of sodium nitrite solution in 5 ml of water was slowly added to the mixture over 30 minutes, and the reaction was continued for 2 hours to obtain diazonium solution. In the meantime, 1.2 g (7.26 mmol) of potassium iodide solution in 15 ml of water was heated up to 60° C., and the diazonium solution was slowly added thereto over 40 minutes. The reaction was continued for 1.5 hours at the same temperature range and cooled. The resulting mixture was then extracted with ethylacetate, dried over anhydrous magnesium sulfate and filtered. The filtrate was evaporated under reduced pressure, and the concentrated product was purified by the column chromatography (ethylacetate:hexane=1:20) to obtain iodine-substituted benzoyl methyl ester (Intermediate compound 20, 1.45 g, Yield of the first step: 87%). Meanwhile, the fourth and fifth steps in the reaction of Example 1 were carried out to obtain 3-bromomethyl-2-iodo-benzoic acid (Intermediate compound 22, Yield of the third step: 74%) through the intermediate compound 21 (Yield of the second step: 53%). The fourth and fifth steps in the reaction of Example 3 were carried out to obtain the intermediate compound 24 (Yield of the fifth step: 71%), and the seventh step in the reaction of Example 1 was carried out to obtain the title compound 5 (160 mg, Yield of the sixth step: 73%).

¹H NMR of the intermediate compound 21:

¹H NMR (300 MHz, CDCl₃): δ 7.59 (dd, 1H), 7.40 (d, J=9.33 Hz 1H), 7.30 (t, 1H), 3.92 (s, 3H), 2.49 (s, 3H)

¹H NMR of the intermediate compound 22:

¹H NMR (300 MHz, CDCl₃): δ 7.56 (dd, 1H), 7.47 (d, J=9.54 Hz, 1H), 7.37 (t, 1H), 4.70 (s, 2H), 3.94 (s, 3H)

¹H NMR of the compound 5:

¹H NMR (300 MHz, CDCl₃): δ 7.46~7.29 (m, 5H), 7.06 (d, J=10.62 Hz, 1H), 6.62~6.51 (m, 1H), 6.57 (s, 1H), 5.53 (s,

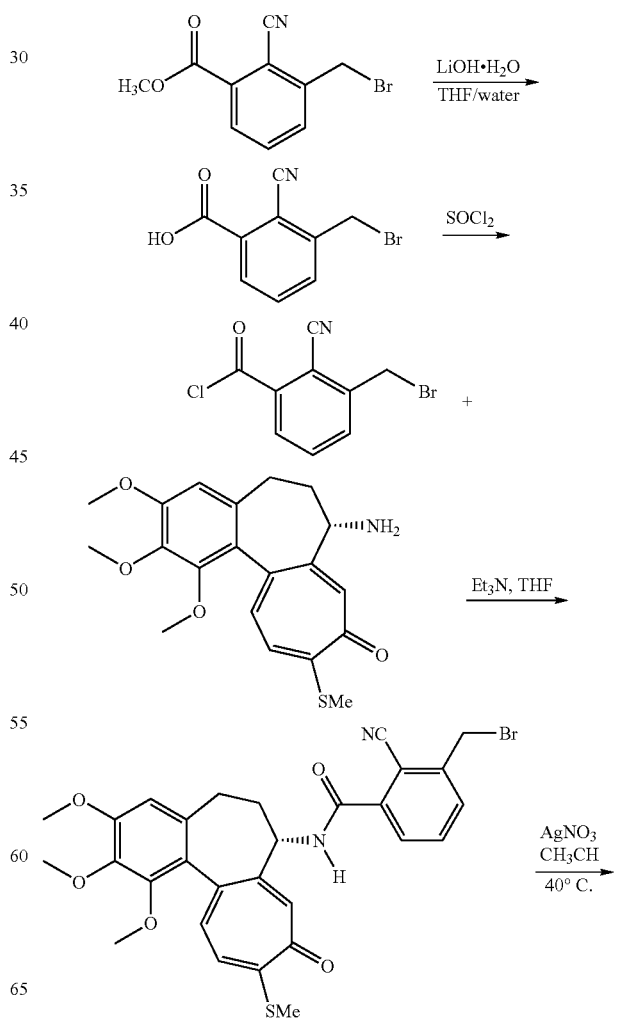

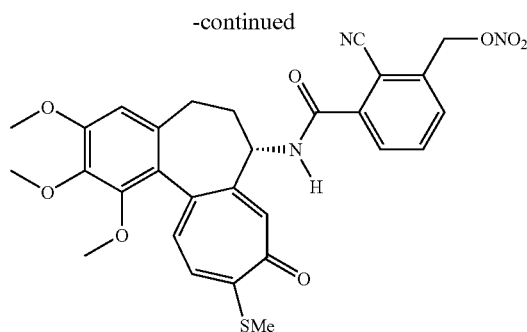

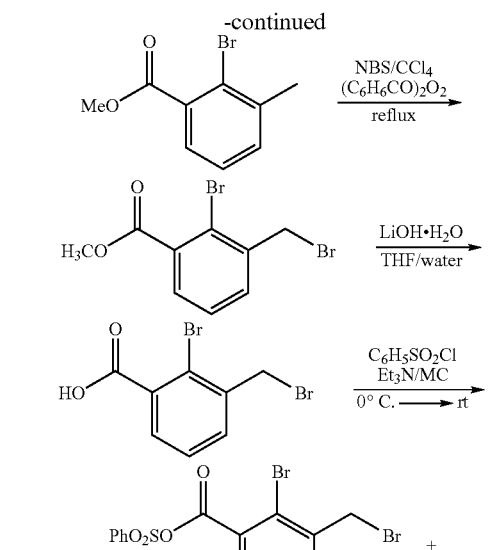

The first step in the reaction of Example 5 was carried out to obtain cyano-substituted benzoyl methyl ester (Intermediate compound 25, 15.16 g, Yield of the first step: 72%) except that copper(I) cyanide and potassium cyanide were used instead of potassium iodide. The fourth and fifth steps in the reaction of Example 1 were carried out to obtain 3-bromomethyl-2-cyano-benzoic acid (Intermediate compound 27, Yield of the third step: 80%) through the intermediate compound 26 (Yield of the second step: 54%). Next, the fourth and fifth steps in the reaction of Example 3 were carried to obtain the intermediate compound 29 (Yield of the fifth step: 54%), and the seventh step in the reaction of Example 1 was carried out to obtain the title compound 6 (7.35 g, Yield of the sixth step: 62%).

$^1$H NMR of the intermediate compound 26:

$^1$H NMR (300 MHz, CDCl$_3$): δ 8.10 (d, J=7.68 Hz, 1H), 7.76 (d, J=7.20 Hz, 1H), 7.67 (t, 1H), 4.73 (s, 2H), 4.01 (s, 3H)

$^1$H NMR of the intermediate compound 27:

$^1$H NMR (300 MHz, CDCl$_3$): δ 8.14 (d, J=7.71 Hz, 1H), 7.75 (d, J=7.89 Hz, 1H), 7.66 (t, 1H), 4.74 (s, 2H)

$^1$H NMR of the intermediate compound 29:

$^1$H NMR (300 MHz, CDCl$_3$): δ 7.83 (d, J=6.21 Hz, 1H), 7.66~7.54 (m, 2H), 7.42 (s, 1H), 7.34 (d, J=110.44 Hz, 1H), 7.08 (d, J=10.62 Hz, 1H), 6.58 (s, 1H), 5.00~4.90 (m, 1H), 4.78 (s, 2H), 3.97 (s, 3H), 3.93 (s, 3H), 3.74 (s, 3H). 2.61~2.40 (m, 3H), 2.44 (s, 3H), 2.10~2.00 (m, 1H)

$^1$H NMR of the compound 6:

$^1$H NMR (300 MHz, CDCl$_3$): δ 7.61~7.49 (m, 2H), 7.37~7.21 (m, 3H), 7.07 (d, J=10.62 Hz, 1H), 6.73 (d, 1H), 6.57 (s, 1H), 5.58 (s, 2H), 4.92~4.83 (m, 1H), 3.96 (s, 3H), 3.93 (s, 3H), 3.72 (s, 3H), 2.63~2.34 (m, 3H), 2.44 (s, 3H), 1.95~1.86 (m, 1H)

Example 7

Preparation of 2-Bromo-3-nitrooxymethyl-N-(1,2,3-trimethoxy-10-methylsulfanyl-9-oxo-5,6,7,9-tetrahydro-benzo[α]heptalen-7-yl)-benzamide

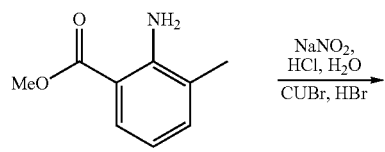

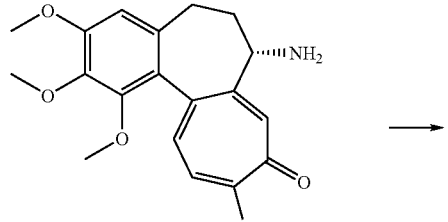

The first step in the reaction of Example 3 was carried out to obtain bromo-substituted benzoyl methyl ester (Intermediate compound 30, 958 mg, Yield of the first step: 74%) except that copper bromide and bromic acid were used instead of copper chloride and hydrochloric acid. The fourth and fifth steps in the reaction of Example 1 were carried out to obtain 3-bromomethyl-2-bromo-benzoic acid (Intermediate compound 32, Yield of the third step: 56%) through the intermediate compound 31 (Yield of the second step: 65%). 245 mg (0.83 mmol) of the intermediate compound 32 was mixed with 25 ml of dichloromethane and was stirred. At a temperature range of 0° C. to 5° C., 0.23 ml of triethylamine and 0.11 ml of benzene sulfonyl chloride were added and the mixture was stirred for 3 hours. The reaction temperature was then slowly raised to room temperature and the reaction was continued for 6 hours. 311 mg (0.83 mmol) of (−)-thiodeacetyl chochicine was added thereto and the mixture was stirred again for 15 hours. The reaction mixture was concentrated under reduced pressure, and the concentrated product was purified by the column chromatography (ethylacetate:hexane=2:1) to obtain 2-bromo-3-bromomethyl-N-(1,2,3-trimethoxy-10-methylsulfanyl-9-oxo-5,6,7,9-tetrahydro-benzo[α]heptalen-7-yl)-benzamide (Intermediate compound 34, 280 mg, Yield of the fifth step: 52%). As for the sixth step, the seventh step in the reaction of Example 1 was carried out to obtain the title compound 7 (156 mg, Yield of the sixth step: 65%).

$^1$H NMR of the intermediate compound 30:

$^1$H NMR (300 MHz, CDCl$_3$): δ 7.46 (d, J=7.59 Hz, 1H), 7.33 (d, J=7.59 Hz, 1H), 7.23 (t, 1H), 3.92 (s, 3H), 2.45 (s, 3H)

$^1$H NMR of the intermediate compound 31:

$^1$H NMR (300 MHz, CDCl$_3$): δ 7.59 (m, 2H), 7.35 (t, 1H), 4.67 (s, 2H), 3.94 (s, 3H)

$^1$H NMR of the intermediate compound 32:

$^1$H NMR (300 MHz, CDCl$_3$): δ 7.70 (d, J=7.41 Hz, 1H), 7.58 (d, J=7.50 Hz, 1H), 7.36 (t, 1H), 4.69 (s, 2H)

$^1$H NMR of the intermediate compound 34:

$^1$H NMR (300 MHz, CDCl$_3$): δ 7.50~7.46 (m, 2H), 7.37~7.28 (m, 3H), 7.05 (d, J=10.41 Hz, 1H), 6.95 (d, J=7.68 Hz, 1H), 6.57 (s, 1H), 4.93~4.90 (m, 1H), 4.70 (s, 2H), 3.97 (s, 3H), 3.93 (s, 3H), 3.73 (s, 3H), 2.60~2.30 (m, 3H), 2.43 (s, 3H), 2.00~1.90 (m, 1H)

$^1$H NMR of the compound 7:

$^1$H NMR (300 MHz, CDCl$_3$): δ 7.47~7.45 (m, 2H), 7.40~7.35 (m, 2H), 7.31 (d, J=10.44 Hz, 1H), 7.06 (d, J=10.26 Hz, 1H), 6.56 (d, J=8.97 Hz, 2H), 5.57 (s, 2H), 4.93~4.84 (m, 1H), 3.97 (s, 3H), 3.93 (s, 3H), 3.72 (s, 3H). 2.61~2.32 (m, 3H), 2.44 (s, 3H), 1.95~1.85 (m, 1H)

Example 8

Preparation of 2-Phenyl-3-nitrooxymethyl-N-(1,2,3-trimethoxy10-methylsulfanyl-9-oxo-5,6,7,9-tetrahydro-benzo[α]heptalen-7-yl)-benzamide

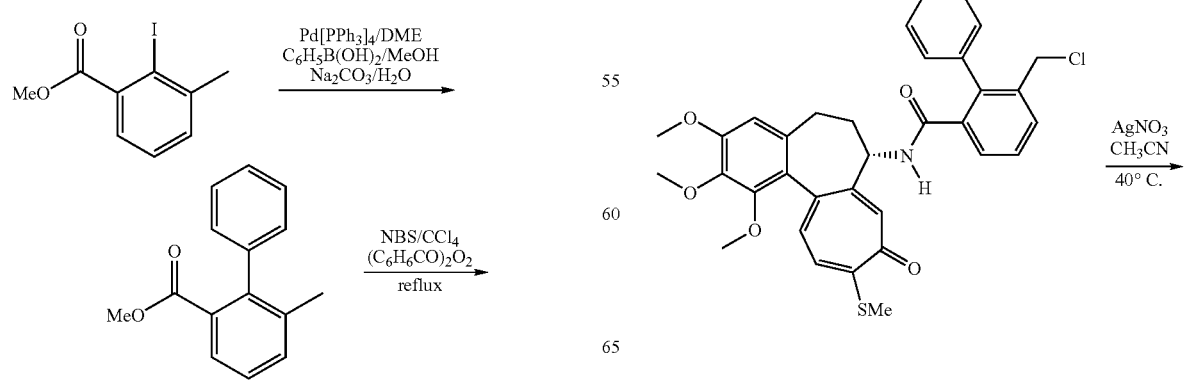

-continued

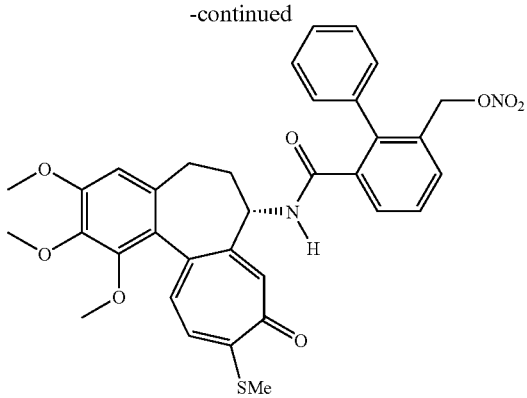

890 mg (0.77 mmol) of Pd[PPh₃]₄ was mixed with 150 ml of 1,2-dimethoxyethane (DME) and was stirred. To the mixture, 854 mg (3.09 mmol) of 2-iodo-3-methyl-benzoylmethylester obtained from Example 5 was added and the reaction was continued for 0.5 hour. Next, 566 mg (4.64 mmol) of phenylboric acid [C₆H₅B(OH)₂] solution in 6 ml of methanol and 982 mg (9.27 mmol) of sodium carbonate solution in 6 ml of water were added and refluxed under heating for 28 hours. The resulting mixture was concentrated under reduced pressure. The residue was extracted with ethylacetate, dried over anhydrous sodium sulfate, filtered and concentrated. The concentrated product was purified by the column chromatography (ethylacetate:hexane=1:20) to obtain 2-phenyl-3-methyl-benzoyl methyl ester (Intermediate compound 35, 580 mg, Yield of the first step: 83%). The fourth and fifth steps in the reaction of Example 1 were carried out to obtain 3-hydromethyl-2-phenyl-benzoic acid (Intermediate compound 37, Yield of the third step: 98%) through the intermediate compound 36 (Yield of the second step: 53%) except that 3 equivalence of lithium hydroxide monohydrate was used. Next, the sixth step in the reaction of Example 1 was carried out to obtain 2-phenyl-3-hydromethyl-N-(1,2,3-trimethoxy-10-methylsulfanyl-9-oxo-5,6,7,9-tetrahydro-benzo[α]heptalen-7-yl)-benzamide (Intermediate compound 38, Yield of the fourth step: 60%). 185 mg (0.32 mmol) of the intermediate compound 38 was then mixed with 20 ml of dichloromethane and stirred. At a temperature range of 0° C. to 5° C., 0.05 ml of triethylamine and 0.04 ml of benzene sulfonyl chloride were added dropwise. The reaction temperature was then slowly raised to room temperature and the reaction was continued for two days. The resulting mixture was concentrated under reduced pressure, and the concentrated product was purified by the column chromatography (ethylacetate:hexane=2:1) to obtain 2-phenyl-3-chloromethyl-N-(1,2,3-trimethoxy-10-methylsulfanyl-9-oxo-5,6,7,9-tetrahydro-benzo[α]heptalen-yl)-benzamide (Intermediate compound 39, 106 mg, Yield of the fifth step: 55%). As for the sixth step, the seventh step in the reaction of Example 1 was carried out to obtain the title compound 8 (112 mg, Yield of the sixth step: 100%).

¹H NMR of the intermediate compound 35:
¹H NMR (300 MHz, CDCl₃): δ 7.68 (d, J=7.68 Hz, 1H), 7.42-7.25 (m, 5H), 7.16 (d, J=6.96 Hz, 2H), 3.53 (s, 3H), 2.10 (s, 3H)

¹H NMR of the intermediate compound 36:
¹H NMR (300 MHz, CDCl₃): δ 7.80 (d, J=7.71 Hz, 1H), 7.67 (d, J=7.77 Hz, 1H), 7.46~7.39 (m, 4H), 7.30-7.26 (m, 2H), 4.28 (s, 2H), 3.54 (s, 3H)

¹H NMR of the intermediate compound 37:
¹H NMR (300 MHz, CDCl₃): δ 7.84 (d, J=7.22 Hz, 1H), 7.74 (d, J=7.68 Hz, 1H), 7.48~7.32 (m, 4H), 7.22~7.19 (m, 2H), 4.38 (s, 2H)

¹H NMR of the intermediate compound 38:
¹H NMR (300 MHz, CDCl₃): δ 7.70 (dd, 2H), 7.50~7.42 (m, 4H), 7.22 (d, J=10.26 Hz, 1H), 6.99 (d, J=10.44 Hz, 1H), 6.85 (s, 1H), 6.46 (s, 1H), 5.54 (d, J=6.96 Hz, 1H), 4.46~4.40 (m, 3H), 3.94 (s, 3H), 3.90 (s, 3H), 3.66 (s, 3H), 2.42 (s, 3H), 2.41~2.18 (m, 2H), 1.44 (m, 1H), 1.10 (m, 1H)

¹H NMR of the intermediate compound 39:
¹H NMR (300 MHz, CDCl₃): δ 7.76 (dd, 1H), 7.65~7.42 (m, 5H), 7.28~7.20 (m, 3H), 6.99 (d, J=10.26 Hz, 1H), 6.84 (s, 1H), 6.46 (s, 1H), 5.53 (d, J=7.14 Hz, 1H), 4.45~4.30 (m, 3H), 3.94 (s, 3H), 3.90 (s, 3H), 3.66 (s, 3H), 2.42 (s, 3H), 2.36~2.17 (m, 3H), 1.47~1.09 (m, 1H)

¹H NMR of the compound 8:
¹H NMR (300 MHz, CDCl₃): δ 7.84 (dd, 1H), 7.63~7.58 (m, 2H), 7.52~7.45 (m, 5H), 7.22 (d, J=10.26 Hz, 1H), 7.00 (d, J=10.62 Hz, 1H), 6.83 (s, 1H), 6.46 (s, 1H), 5.57 (d, J=7.14 Hz, 1H), 5.25~5.14 (AB quartet, 2H), 4.42 (m, 1H), 3.94 (s, 3H), 3.90 (s, 3H), 3.66 (s, 3H), 2.42 (s, 3H), 2.41~2.17 (m, 2H), 1.55~1.40 (m, 1H), 1.20~1.05 (m, 1H)

Example 9

Preparation of 2-Iodo-3-methyl-N-(1,2,3-trimethoxy-10-methylsulfanyl-9-oxo-5,6,7,9-tetrahydro-benzo[α]heptalen-7-yl)-benzamide

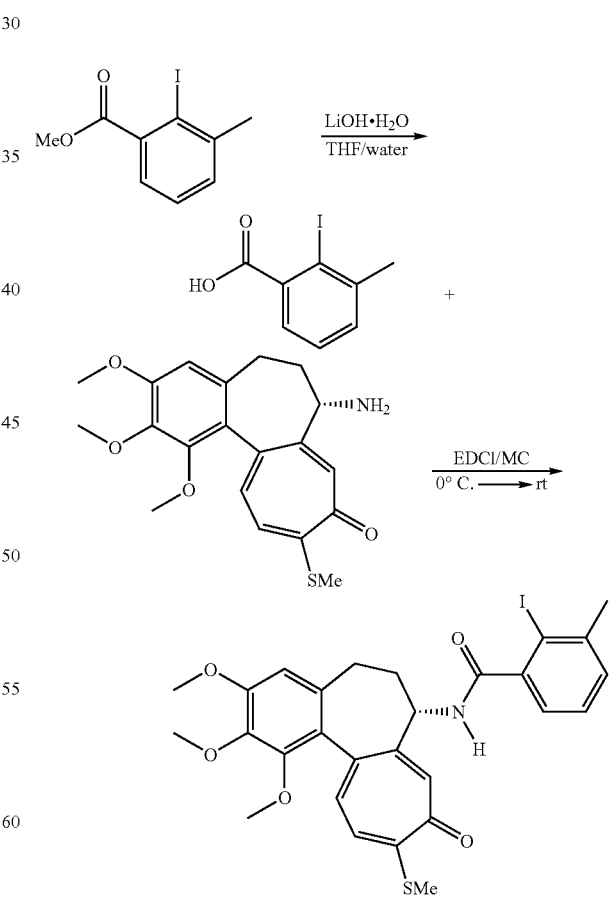

2-Iodo-3-methyl-benzoyl methyl ester obtained from Example 5 went through the fifth step in the reaction of Example 1 to obtain 2-iodo-3-methyl benzoic acid (Intermediate compound 40, Yield of the first step: 83%). Then, the intermediate compound 40 and (−)-thiodeacetyl colchicine was subjected to the sixth step in the reaction of Example 1 to obtain the title compound 9 (215 mg, Yield of the second step: 83%).

¹H NMR of the intermediate compound 40:

¹H NMR (300 MHz, CDCl₃): δ 7.65 (dd, 1H), 7.40 (dd, 1H), 7.31 (t, 1H), 2.49 (s, 3H)

¹H NMR of the compound 9:

¹H NMR (300 MHz, CDCl₃): δ 7.36~7.25 (m, 5H), 7.06 (d, J=10.80 Hz, 1H), 6.57 (s, 1H), 6.29 (d, 1H), 4.95~4.80 (m, 1H), 3.97 (s, 3H), 3.93 (s, 3H), 3.72 (s, 3H), 2.65~2.30 (m, 3H), 2.45 (s, 3H), 2.00~1.80 (m, 1H)

Example 10

Preparation of 2-Chloro-3-methyl-N-(1,2,3-trimethoxy-10-methylsulfanyl-9-oxo-5,6,7,9-tetrahydro-benzo[α]heptalen-7-yl)-benzamide

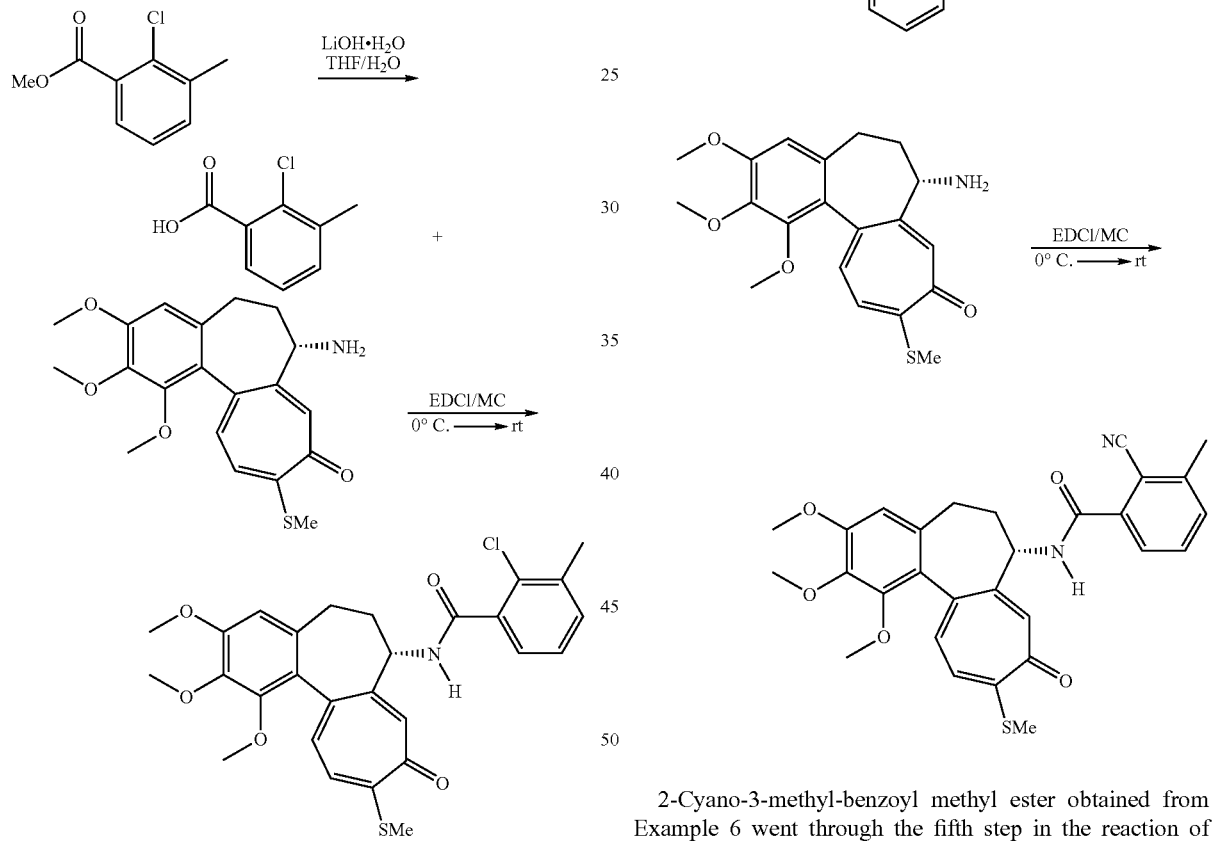

2-Chloro-3-methyl-benzoyl methyl ester obtained from Example 3 went through the fifth step in the reaction of Example 1 to obtain 2-chloro-3-methyl benzoic acid (Intermediate compound 41). Then, the intermediate compound 41 and (−)-thiodeacetyl colchicine was subjected to the sixth step in the reaction of Example 1 to obtain the title compound 10 (Yield of the second step: 45%).

¹H NMR of the compound 10:

¹H NMR (300 MHz, CDCl₃): δ 7.46~7.29 (m, 5H), 7.06 (d, J=9.9 Hz, 1H), 6.57 (s, 1H), 6.51 (d, J=7.32 Hz, 1H), 4.91~4.85 (m, 1H), 3.96 (s, 3H), 3.91 (s, 3H) 3.70 (s, 3H), 2.40 (s, 3H), 2.04 (s, 2H), 1.56 (s, 3H), 1.32~1.20 (m, 2H)

Example 11

Preparation of 2-Cyano-3-methyl-N-(1,2,3-trimethoxy-10-methylsulfanyl-9-oxo-5,6,7,9-tetrahydro-benzo[α]heptalen-7-yl)-benzamide

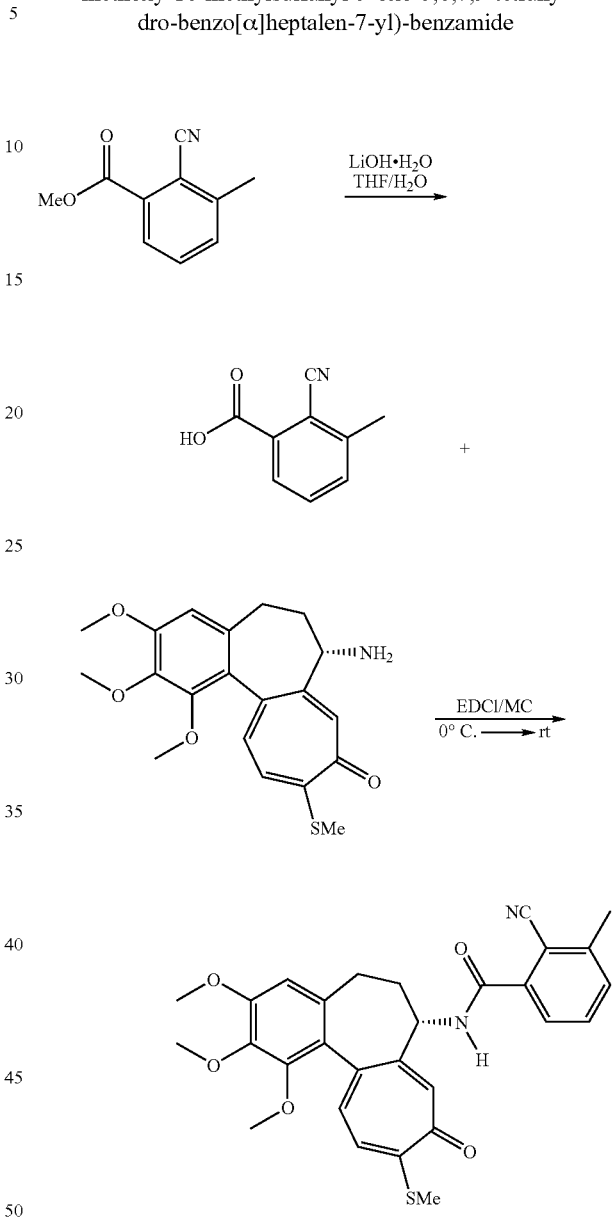

2-Cyano-3-methyl-benzoyl methyl ester obtained from Example 6 went through the fifth step in the reaction of Example 1 to obtain 2-cyano-3-methyl benzoic acid (Intermediate compound 42, Yield of the first step: 78%). Then, the intermediate compound 42 and (−)-thiodeacetyl colchicine was subjected to the sixth step in the reaction of Example 1 to obtain the title compound 11 (136 mg, Yield of the second step: 39%).

¹H NMR the compound 11:

¹H NMR (300 MHz, CDCl₃): δ 7.37 (s, 1H), 7.34~7.25 (m, 3H), 7.18 (d, J=7.50 Hz, 1H), 7.05 (d, J=10.62 Hz, 1H), 6.67 (d, J=7.50 Hz, 1H), 6.57 (s, 1H), 4.92~4.86 (m, 1H), 3.96 (s, 3H), 3.92 (s, 3H), 3.72 (s, 3H), 2.59~2.30 (m, 3H), 2.43 (s, 3H), 2.39 (s, 3H), 1.94~1.88 (m, 1H)

Example 12

Preparation of 2-Fluoro-5-methyl-N-(1,2,3-trimethoxy-10-methylsulfanyl-9-oxo-5,6,7,9-tetrahydro-benzo[α]heptalen-7-yl)-benzamide

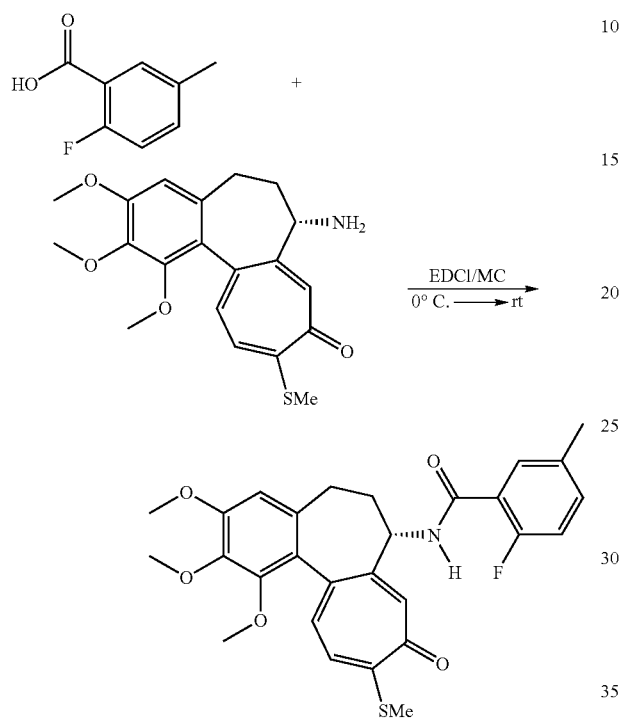

The sixth step in the reaction of Example 1 was carried out to obtain the title compound 12 (85 mg, Yield of the first step: 37%) except that 2-fluoro-5-methyl benzoic acid was used instead of 2-fluoro-3-bromomethyl benzoic acid.

$^1$H NMR (300 MHz, CDCl$_3$): δ 7.71 (d, J=7.68 Hz, 1H), 7.31 (d, J=10.26 Hz, 1H), 7.27~7.11 (m, 3H), 7.02~76.99 (m, 2H), 6.56 (s, 1H), 4.83~4.80 (m, 1H), 3.96 (s, 3H), 3.91 (s, 3H), 3.72 (s, 3H), 2.75~2.25 (m, 3H), 2.42 (s, 3H), 1.98~1.92 (m, 1H)

Example 13

Preparation of 3-Methyl-N-(1,2,3-trimethoxy-10-methylsulfanyl-9-oxo-5,6,7,9-tetrahydro-benzo[α]heptalen-7-yl)-benzamide

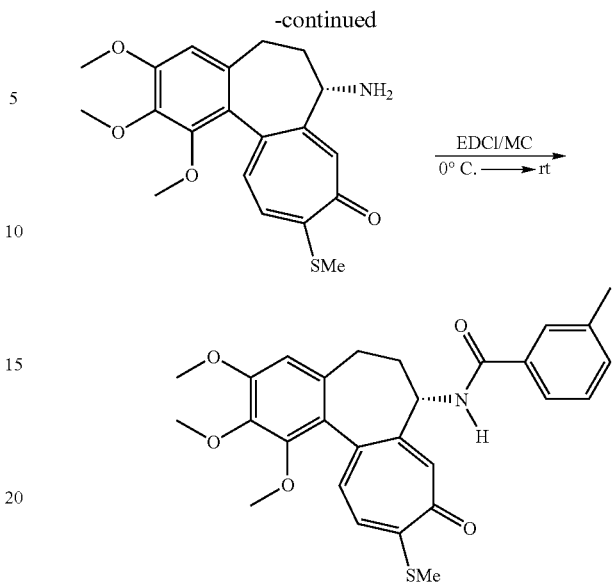

The sixth step in the reaction of Example 1 was carried out to obtain the title compound 13 (212 mg, Yield of the first step: 67%) except that 3-methyl benzoic acid was used instead of 2-fluoro-3-bromomethyl benzoic acid.

$^1$H NMR (300 MHz, CDCl$_3$): δ 7.68~7053 (m, 2H), 7.34~7.25 (m, 4H), 7.06 (d, J=9.33 Hz, 1H), 6.76 (d, J=6.78 Hz, 1H), 6.56 (s, 1H), 4.91~4.80 (m, 1H), 3.96 (s, 3H), 3.91 (s, 3H), 3.73 (s, 3H), 2.62~2.30 (m, 3H), 2.43 (s, 3H), 2.35 (s, 3H), 2.03~1.91 (m, 1H)

Example 14

Preparation of 2-Nitro-3-nitrooxymethyl-N-(1,2,3-trimethoxy-10-methylsulfanyl-9-oxo-5,6,7,9-tetrahydro-benzo[α]heptalen-7-yl)-benzamide

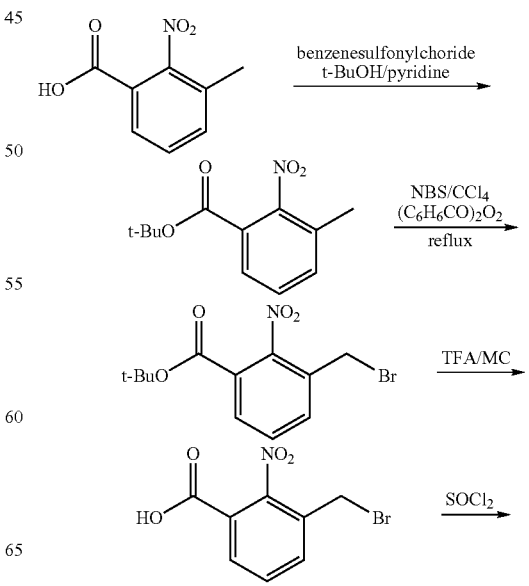

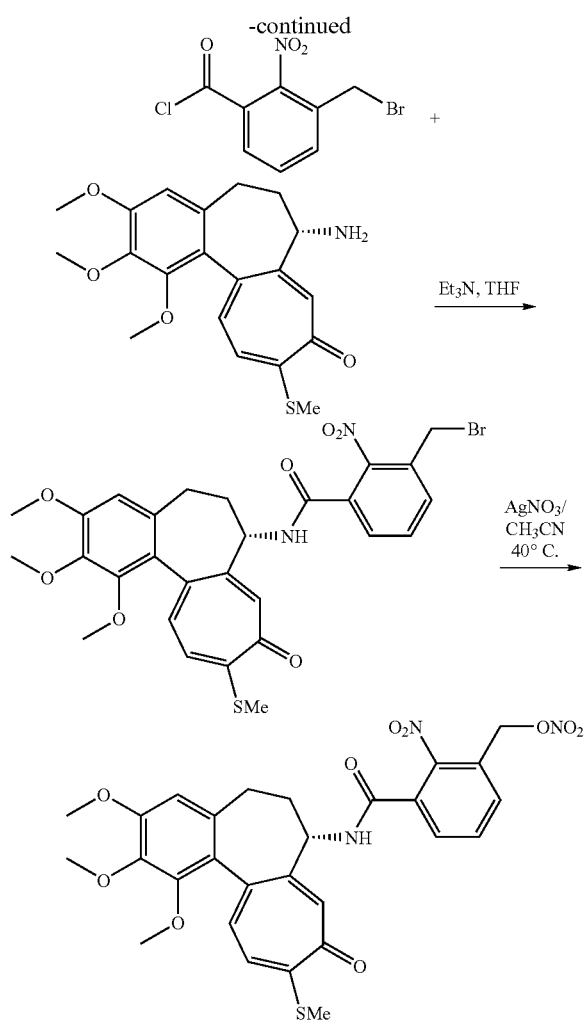

200 mg (1.104 mmol) of 2-nitro-3-methyl benzoic acid was dissolved in 16 ml of pyridine. 468 mg (2.208 mmol) of benzene sulfonyl chloride was added thereto and stirred at room temperature for 2 hours. 329 mg (4.146 mmol) of t-butanol was added thereto and stirred at room temperature for 15 hours. The reaction mixture was extracted with dichloromethane and pyridine was removed by using 2N hydrochloric acid. The organic layer was then neutralized with sodium bicarbonate solution and dried over anhydrous magnesium sulfate. The resulting mixture was concentrated under reduced pressure. The concentrated product was then purified by the column chromatography (ethylacetate:hexane=1:30) to obtain 2-nitro-3-methyl benzoic acid t-butyl ester (Intermediate compound 43, 194 mg, Yield of the first step: 74%). 190 mg (0.800 mmol) of the first intermediate compound 43 as a starting material was subjected to the third step in the reaction of Example 1 to obtain 3-bromomethyl-2-nitrobenzoic acid t-butyl ester (Intermediate compound 44, 160 mg, Yield of the second step: 63%). 154 mg (0.487 mmol) of the intermediate compound 44 was dissolved in 7 ml of dichloromethane, and trifluoroacetic acid was added thereto. The mixture was stirred for 6 hours. When the reaction was completed, the resulting mixture was concentrated under reduced pressure and 3-bromomethyl-2-nitrobenzoic acid (Intermediate compound 45, 121 mg, Yield of the third step: 96%) was obtained. The intermediate compound 45 as a starting material was subjected to the fourth through sixth steps in the reaction of Example 3 to obtain the title compound 14 (83 mg, Yield of the sixth step: 14%).

¹H NMR of the intermediate compound 43:
¹H NMR (300 MHz, CDCl₃): δ 7.79 (m, 1H), 7.44~7.42 (m, 2H), 2.12 (s, 3H), 1.54 (s, 9H)

¹H NMR of the intermediate compound 44:
¹H NMR (300 MHz, CDCl₃): δ 8.26 (d, J=9.33 Hz, 1H), 7.93 (d, 1H), 7.67 (t, 1H), 4.44 (s, 2H), 1.54 (s, 9H)

¹H NMR of the intermediate compound 45:
¹H NMR (300 MHz, CDCl₃): δ 8.05 (d, 1H), 8.01 (d, J=6.90 Hz, 1H), 7.59 (t, 1H), 4.43 (s, 2H)

¹H NMR of the intermediate compound 47:
¹H NMR (300 MHz, CDCl₃): δ 7.75 (d, J=6.24 Hz, 1H), 7.58~7.47 (m, 3H), 7.32 (d, 1H), 7.07 (d, J=10.62 Hz, 1H), 6.55 (s, 1H), 4.87 (m, 1H), 3.95 (d, J=9.69 Hz 6H), 3.68 (s, 3H), 2.57~2.41 (m, 3H), 2.41 (s, 3H), 2.05~1.94 (m, 1H)

¹H NMR of the compound 14:
¹H NMR (300 MHz, CDCl₃): δ 8.12 (d, J=7.68 Hz, 1H), 7.87~7.84 (m, 1H), 7.59~7.54 (m, 3H), 7.33 (d, J=10.41 Hz, 1H), 7.07 (d, J=10.41 Hz, 1H), 6.56 (s, 1H), 5.58~5.46 (AB quartet, 2H), 4.95~4.85 (m, 1H), 3.96 (s, 3H), 3.93 (s, 3H), 3.69 (s, 3H), 2.57~2.41 (m, 3H), 2.41 (s, 3H), 2.05~1.94 (m, 1H)

Example 15

Preparation of 3-Methyl-N-(1,2,3-trimethoxy-10-methylsulfanyl-9-oxo-5,6,7,9-tetrahydro-benzo[α]heptalen-7-yl)-benzamide

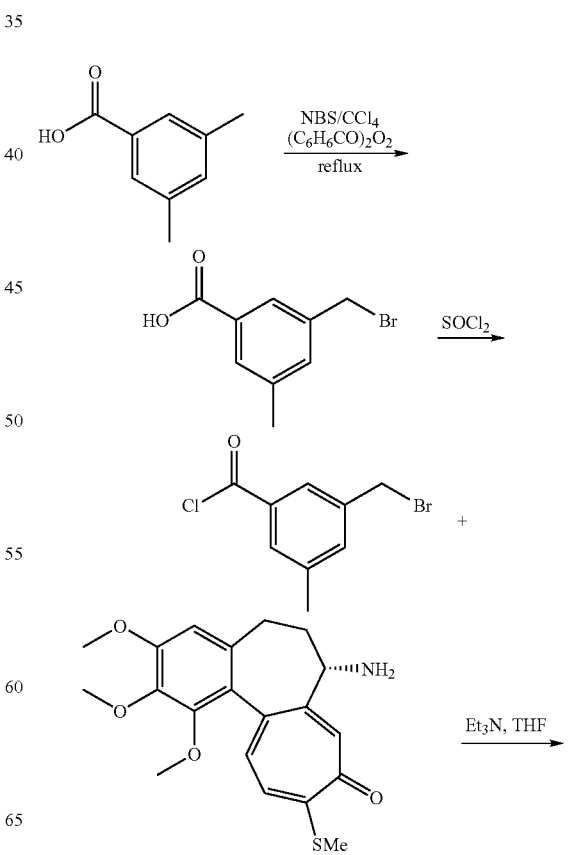

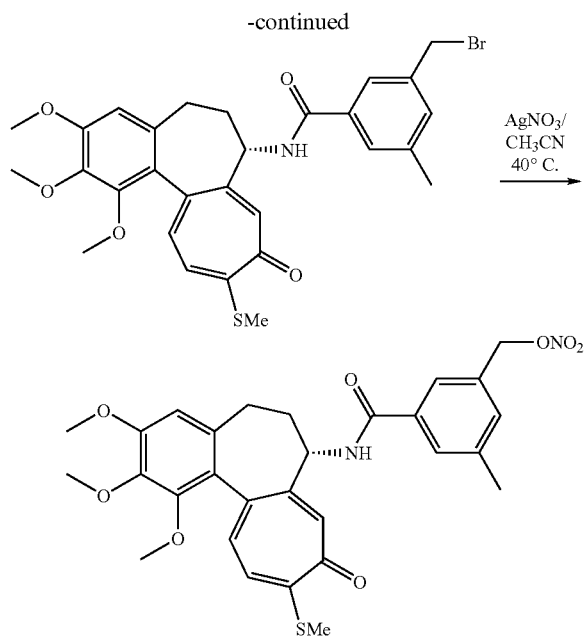

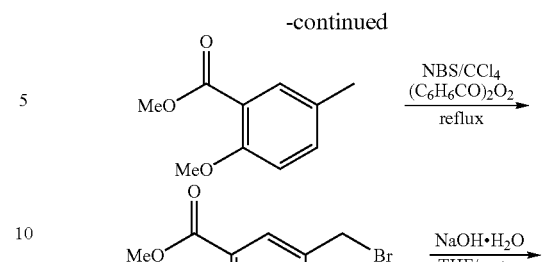

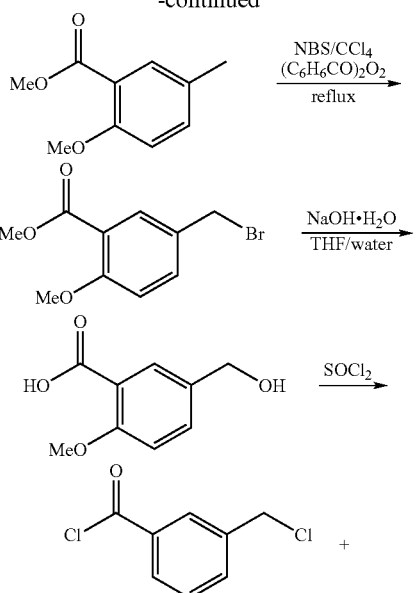

Using 3,5-dimethyl benzoic acid as a staring material, the fourth step in the reaction of Example 1 was carried out to obtain 3-bromomethyl-5-methyl benzoic acid (Intermediate compound 48, 64 mg, Yield of the first step: 36%). The fourth through sixth steps in the reaction of Example 3 were then carried out to obtain the title compound 15 (83 mg, Yield of the fourth step: 9%).

$^1$H NMR of the intermediate compound 48:

$^1$H NMR (300 MHz, CDCl$_3$): δ 7.94 (s, 1H), 7.86 (s, 1H), 7.46 (s, 1H), 4.50 (s, 2H), 2.42 (s, 3H)

$^1$H NMR of the compound 15:

$^1$H NMR (300 MHz, CDCl$_3$): δ 8.60 (d, J=7.14 Hz, 1H), 7.72 (s, 1H), 7.53~7.36 (m, 3H), 7.17~7.09 (m, 2H), 6.57 (s, 1H), 5.18~5.07 (AB quartet, 2H), 4.98~4.93 (m, 1H), 3.97 (s, 3H), 3.92 (s, 3H), 3.75 (s, 3H). 2.61~2.26 (m, 4H), 2.44 (s, 3H), 2.15 (s, 3H)

Example 16

Preparation of 2-Methoxy-5-nitrooxymethyl-N-(1,2,3-trimethoxy-10-methylsulfanyl-9-oxo-5,6,7,9-tetrahydro-benzo[α]heptalen-7-yl)-benzamide

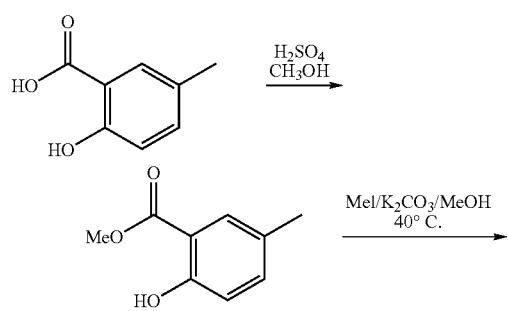

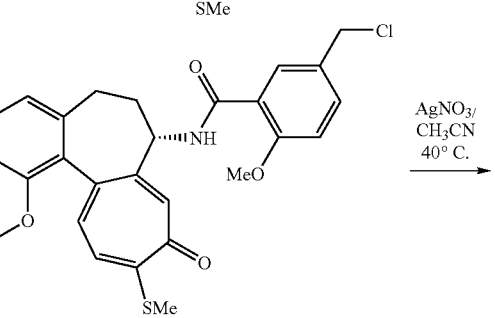

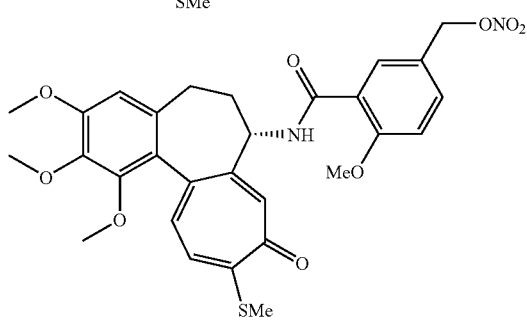

1 g (6.44 mmol) of 2-hydroxy-5-methyl benzoic acid was subjected to the first step in the reaction of Example 1 to obtain 2-hydroxy-5-methyl benzoyl methyl ester (Intermediate compound 51, 0.968 g, Yield of the first step: 90%). 450 mg (2.71 mmol) of the intermediate compound 51 was then dissolved in 15 ml of methanol, and 0.5 ml (8.12 mmol) of iodomethane and 375 mg (2.71 mmol) of potassium carbonate were added thereto. The mixture was stirred under heating at about 40° C. After the reaction was completed, the mixture was cooled to room temperature and concentrated under reduced pressure. The residue was extracted with ethyl acetate, dried over anhydrous magnesium sulfate, filtered and concentrated under reduced pressure. The concentrated product was purified by the column chromatography (ethylacetate:hexane=10:1) to obtain 2-methoxy-5-methyl benzoic acid methyl ester (Intermediate compound 52, 421 mg, Yield of the second step: 84%). The intermediate compound 52 was subjected to the second through sixth steps in the reaction of Example 3 to obtain the title compound 16 (83 mg, Yield of the seventh step: 11%).

$^1$H NMR of the intermediate compound 51:

$^1$H NMR (300 MHz, CDCl$_3$): δ 10.55 (s, 1H), 7.63 (s, 1H), 7.32~7.24 (m, 1H), 6.88 (d, J=8.43 Hz, 1H), 2.30 (s, 3H)

$^1$H NMR of the intermediate compound 52:

$^1$H NMR (300 MHz, CDCl$_3$): δ 7.60 (s, 1H), 7.27 (d, J=8.43 Hz, 1H), 7.68 (d, J=8.43 Hz, 1H), 3.88 (s, 3H), 3.87 (s, 3H), 2.30 (s, 3H)

$^1$H NMR of the intermediate compound 52:

$^1$H NMR (300 MHz, CDCl$_3$): δ 7.84 (s, 1H), 7.51 (d, J=8.58 Hz, 1H), 6.95 (d, J=8.58 Hz, 1H), 4.48 (s, 2H), 3.93 (s, 3H), 3.91 (s, 3H)

$^1$H NMR of the intermediate compound 54:

$^1$H NMR (300 MHz, CDCl$_3$): δ 9.92 (s, 1H), 8.33 (s, 1H), 8.03 (d, J=8.61 Hz, 1H), 7.12 (d, J=8.61 Hz, 1H), 4.00 (s, 2H), 3.91 (s, 3H), 3.91 (s, 3H)

$^1$H NMR of the intermediate compound 56:

$^1$H NMR (300 MHz, CDCl$_3$): δ 8.23 (d, J=7.14 Hz, 1H), 8.01 (s, 1H), 7.49 (d, J=8.61 Hz, 1H), 7.29 (s, 1H), 7.02 (t, J=10.26 Hz, 1H), 6.56 (s, 1H), 4.84 (m, 1H), 4.52 (s, 2H), 3.96 (s, 3H), 3.91 (s, 3H), 3.73 (s, 3H), 2.57~2.35 (m, 3H), 2.42 (s, 3H), 1.97~1.85 (m, 1H)

$^1$H NMR of the compound 16:

$^1$H NMR (300 MHz, CDCl$_3$): δ 8.09 (d, J=6.96 Hz, 1H), 8.06 (s, 1H), 7.50 (d, 8.46 Hz, 1H), 7.33-7.26 (m, 2H), 7.06-7.03 (m, 2H), 6.56 (s, 1H), 5.34 (s, 2H), 4.82 (m, 1H), 4.08 (s, 3H), 3.96 (s, 3H), 3.91 (s, 3H), 3.72 (s, 3H), 2.63-2.48 (m, 2H), 2.42 (s, 3H), 1.93-1.77 (m, 2H)

Example 17

Preparation of 3-Dimethylamino-N-(1,2,3-trimethoxy-10-methylsulfanyl-9-oxo-5,6,7,9-tetrahydro-benzo[α]heptalen-7-yl)-benzamide

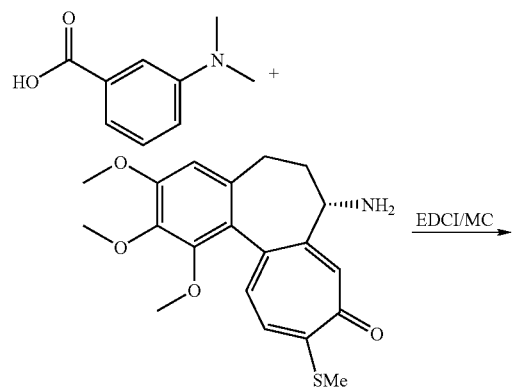

-continued

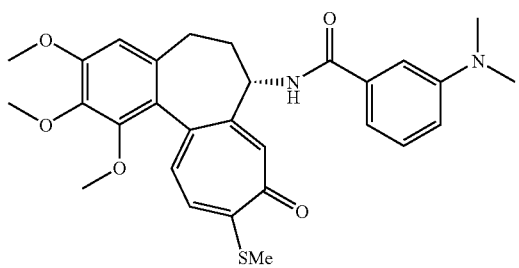

The sixth step in the reaction of Example 1 was carried out to obtain the title compound 17 (48 mg, Yield: 17%) except that 3-dimethylaminobenzoic acid was used instead of 2-fluoro-3-bromomethyl benzoic acid.

$^1$H NMR (300 MHz, CDCl$_3$): $^1$H NMR (300 MHz, CDCl$_3$): δ 7.45 (d, J=6.78 Hz, 1H), 7.29 (t, 1H), 7.18~7.03 (m, 3H), 6.76 (s, 1H), 6.55 (s, 1H), 4.90 (m, 1H), 3.95 (s, 3H), 3.90 (s, 3H), 3.73 (s, 3H), 2.89 (s, 6H), 2.45 (m, 3H), 2.42 (s, 3H), 2.02 (m, 1H)

Example 18

Preparation of 2-(2-Mercapto-4-methyl-thiazol-5-yl)-N-(1,2,3-trimethoxy-10-methylsulfanyl-9-oxo-5,6,7,9-tetrahydro-benzo[α]heptalen-7-yl)-acetamide

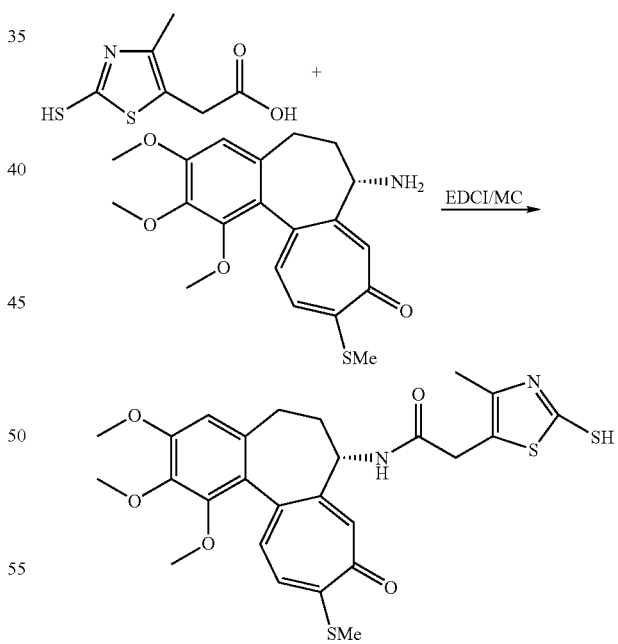

The sixth step in the reaction of Example 1 was carried out to obtain the title compound 18 (58 mg, Yield: 83%) except that 2-mercapto-4-methyl-5-thiazolacetic acid was used instead of 2-fluoro-3-bromomethyl benzoic acid.

$^1$H NMR (300 MHz, CDCl$_3$): δ 12.18 (s, 1H), 7.80 (d, J=3.06 Hz, 1H), 7.67 (s, 1H), 7.35 (d, J=10.26 Hz, 1H), 7.14 (d, J=10.8 Hz, 1H), 6.53 (s, H), 4.73 (m, 1H), 3.93 (s, 3H), 3.90 (s, 3H), 3.65 (s, 3H), 3.53 (m, 2H), 2.45 (s, 3H), 2.37 (m, 2H), 2.17 (s, 3H), 1.98 (m, 2H)

Example 19

Preparation of 2-(2-Thionitrite-4-methyl-thiazol-5-yl)-N-(1,2,3-trimethoxy-10-methylsulfanyl-9-oxo-5,6,7,9-tetrahydro-benzo[α]heptalen-7-yl)-acetamide

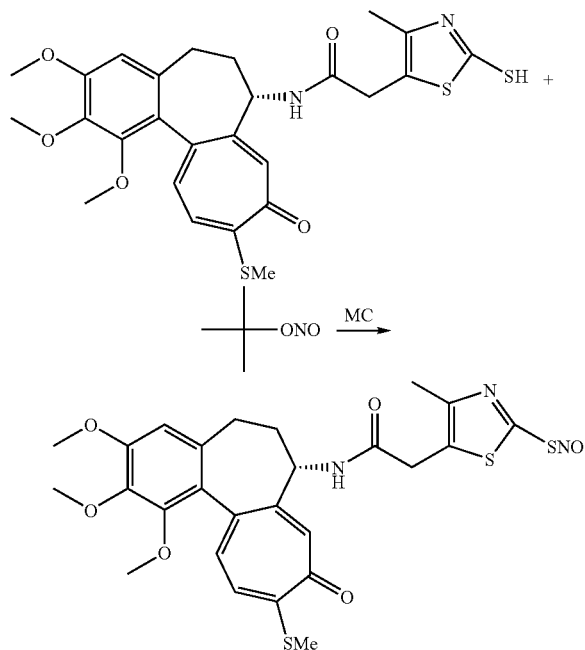

100 mg (0.189 mmol) of 2-(2-mercapto-4-methyl-thiazol-5-yl)-N-(1,2,3-trimethoxy-10-methylsulfanyl-9-oxo-5,6,7,9-tetrahydro-benzo[α]heptalen-7-yl)-acetamide obtained from Example 18 was dissolved in 40 ml of dichloromethane and 59 mg (0.567 mmol) of t-butyl nitrite was added thereto. The mixture was stirred at room temperature for 1 hour. The resulting mixture was concentrated under reduced pressure, and the concentrated product was purified by the column chromatography (dichloromethane: methanol=9:1) to obtain the title compound 19 (72 mg, Yield: 65%).

¹H NMR (300 MHz, CDCl₃): δ 8.52 (d, J=8.79 Hz, 1H), 7.85 (s, 1H), 7.35 (d, J=10.44 Hz, 1H), 7.11 (d, J=10.62 Hz, 1H), 6.50 (s, H), 4.84 (m, 1H), 4.22 (s, 1H), 3.94 (s, 3H), 3.89 (s, 3H), 3.69 (s, 3H), 3.66 (d, 1H), 2.45 (s, 3H), 2.42 (s, 3H), 2.25 (m, 2H), 1.72 (m, 2H)

Example 20

Preparation of 2-(2,5-Dioxo-imidazolidin-4-yl)-N-(1,2,3-trimethoxy-10-methylsulfanyl-9-oxo-5,6,7,9-tetrahydro-benzo[α]heptalen-7-yl)-acetamide

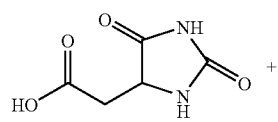

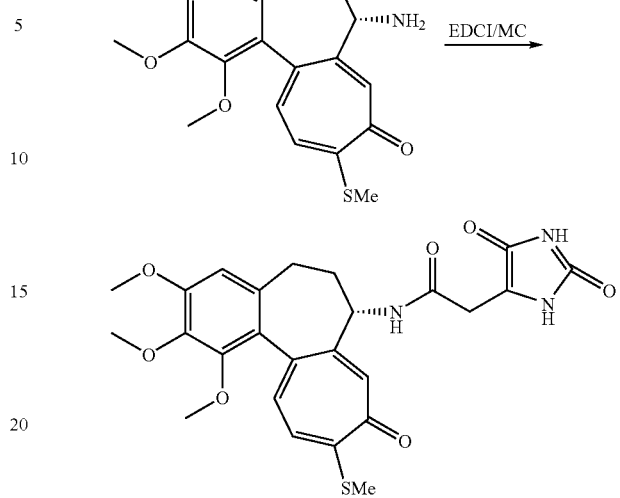

The sixth step in the reaction of Example 1 was carried out to obtain the title compound 20 (434 mg, Yield: 60%) except that thymine-1-acetic acid was used instead of 2-fluoro-3-bromomethyl benzoic acid.

¹H NMR (300 MHz, CDCl₃): δ 9.85 (s, 1H), 8.17 (dd, 1H), 7.44 (s, 1H), 7.30 (d, J=10.44 Hz, 1H), 7.09 (d, J=12.46 Hz, 1H), 6.75 (s, 1H), 6.54 (s, H), 4.63 (m, 1H), 4.32 (m, 1H), 3.92 (s, 3H), 3.89 (s, 3H), 3.65 (s, 3H), 2.56 (m, 3H), 2.40 (s, 3H), 1.96 (m, 1H)

Example 21

Preparation of 6-Methyl-pyrimidine-4-carboxylic acid (1,2,3-trimethoxy-10-methylsulfanyl-9-oxo-5,6,7,9-tetrahydro-benzo[α]heptalen-7-yl)-amide

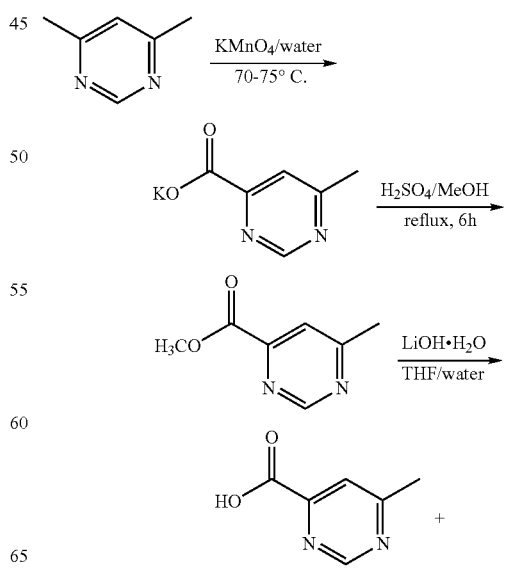

-continued

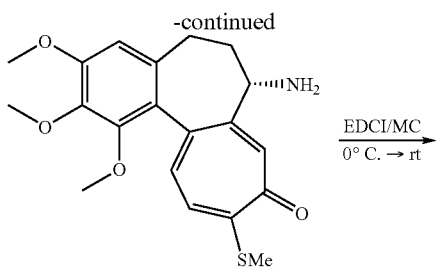

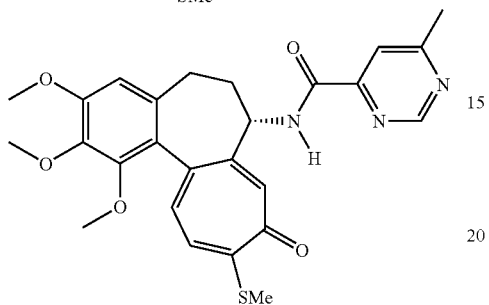

1.77 g (16.37 mmol) of 4,6-dimethylpyrimidine was dissolved in 20 ml of water and stirred. 5.69 g (36.01 mmol) of potassium permanganate solution in 60 ml of water was added thereto and heated at temperature of 70° C. to 75° C. After the color of potassium permanganate disappeared, the mixture was filtered with celite and extracted with dichloromethane to collect the remaining starting material. The aqueous layer was removed under reduced pressure to obtain potassium 6-methylpyrimidine-4-carboxylate (Intermediate compound 57). 3.45 g of the intermediate compound 57 was mixed with 250 ml of methanol and 1.7 ml of conc. sulfuric acid, and the mixture was refluxed under heating for 6 hours. The solvent in the mixture was then removed under reduced pressure. The residue was diluted with ethyl acetate and water, and neutralized by sodium bicarbonate solution, and then extracted with ethyl acetate. The organic layer was dried over anhydrous magnesium sulfate, filtered and concentrated under reduced pressure. The concentrated product was purified by the column chromatography (ethylacetate:hexane=1:1) to obtain 6-methylpyrimidine-4-carboxylic acid methyl ester (Intermediate compound 58, 930 mg, Yield of the first and second steps: 37%). The intermediate compound 58 was then subjected to the fifth step in the reaction of Example 1 to obtain 6-methylpyrimine-4-carboxylic acid (Intermediate compound 59, Yield of the third step: 62%). Next, the intermediate compound 59 and (−)-thiodeacetyl colchicine were subjected to the sixth step in the reaction of Example 1 to obtain the title compound 21 (Yield of the fourth step: 37%).

¹H NMR of the intermediate compound 58:

¹H NMR (300 MHz, CDCl₃): δ 9.26 (s, 1H), 7.92 (s, 1H), 4.04 (s, 3H), 2.67 (s, 3H)

¹H NMR of the intermediate compound 59:

¹H NMR (300 MHz, CDCl₃): δ 9.22 (s, 1H), 7.95 (s, 1H), 2.67 (s, 3H)

¹H NMR of the compound 21:

¹H NMR (300 MHz, CDCl₃): δ 9.12 (s, 1H), 8.43 (d, J=7.5 Hz, 1H), 7.82 (s, 1H), 7.31 (d, J=10.26 Hz, 1H), 7.19 (s, 1H), 7.05 (d, J=10.44 Hz, 1H), 6.57 (s, 1H), 5.30 (s, 2H), 4.81~4.77 (m, 1H), 3.96 (s, 3H), 3.91 (s, 3H), 3.72 (s, 3H), 2.60~2.30 (m, 3H), 2.55 (s, 3H), 2.43 (s, 3H), 2.10~1.90 (m, 1H)

Example 22

Preparation of 6-Bromomethyl-pyrimidine-4-carboxylic acid (1,2,3-trimethoxy-10-methylsulfanyl-9-oxo-5,6,7,9-tetrahydro-benzo[α]heptalen-7-yl)-amide

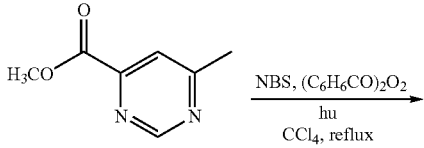

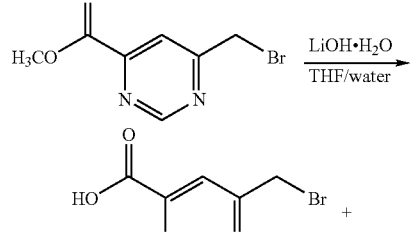

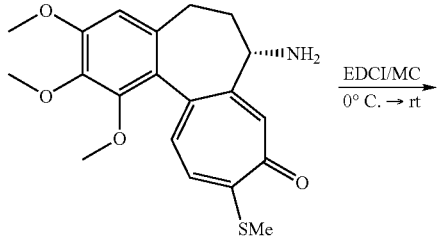

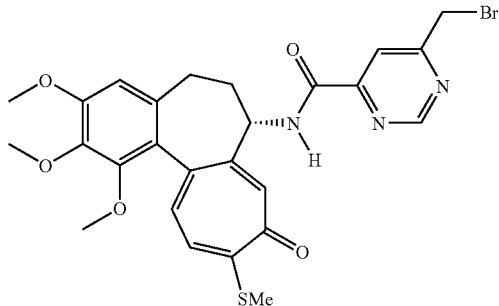

6-Methyl-pyrimidine-4-carboxylic acid methyl ester obtained from Example 21 was subjected to the fourth through sixth steps in the reaction of Example 1 to obtain the title compound 22 (Yield of the third step: 18%).

¹H NMR of the intermediate compound 60:

¹H NMR (300 MHz, CDCl₃): δ 9.35 (s, 1H), 8.19 (s, 1H), 4.54 (s, 2H), 4.07 (s, 3H)

¹H NMR of the intermediate compound 61:

¹H NMR (300 MHz, CDCl₃): δ 9.33 (s, 1H), 8.22 (s, 1H), 4.55 (s, 2H)

¹H NMR of the compound 22:

¹H NMR (300 MHz, CDCl₃): δ 9.21 (s, 1H), 8.41 (d, J=7.5 Hz, 1H), 8.18 (s, 1H), 7.32 (d, J=10.44 Hz, 1H), 7.20 (s, 1H), 7.06 (d, J=10.44 Hz, 1H), 6.58 (s, 1H), 4.85~4.76 (m, 2H), 4.66 (s, 2H), 3.96 (s, 3H), 3.91 (s, 3H), 3.73 (s, 3H), 2.66~2.28 (m, 3H), 2.43 (s, 3H), 2.10~2.05 (m, 1H)

Example 23

Preparation of 6-Nitrooxymethyl-pyridine-2-carboxylic acid (1,2,3-trimethoxy-10-methylsulfanyl-9-oxo-5,6,7,9-tetrahydro-benzo[α]heptalen-7-yl)-amide

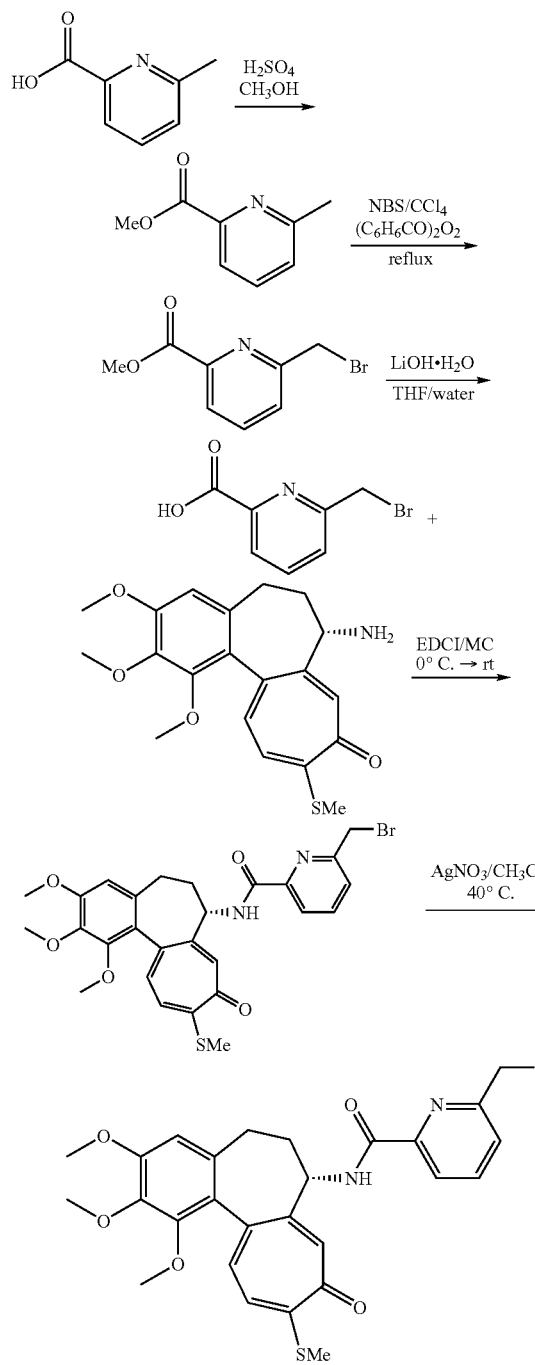

1 g (6.93 mmol) of 3-methyl-5-carboxilic acid pyridine was subjected to the first step in the reaction of Example 1 to obtain 3-methyl-5-carboxylic acid pyridine methyl ester (Intermediate compound 62, 546 mg, Yield of the first step: 52%). Then, the intermediate compound 62 was subjected to the fourth through seventh steps in the reaction of Example 1 to obtain the title compound 23 (46 mg, Yield of the fifth step: 5%).

¹H NMR of the intermediate compound 62:
¹H NMR (300 MHz, CDCl₃): δ 7.97 (d, J=7.86 Hz, 1H), 7.73 (t, J=7.68 Hz, 1H), 7.35 (d, J=7.86 Hz, 1H), 4.00 (s, 3H), 2.67 (s, 3H)

¹H NMR of the intermediate compound 63:
¹H NMR (300 MHz, CDCl₃): δ 8.07 (d, J=7.86 Hz, 1H), 7.88 (t, J=7.68 Hz, 1H), 7.70 (d, J=7.86 Hz, 1H), 4.65 (s, 2H), 4.02 (s, 3H)

¹H NMR of the intermediate compound 64:
¹H NMR (300 MHz, CD₃OD): δ 8.05 (d, J=7.8 Hz, 1H), 7.97 (t, J=7.68 Hz, 1H), 7.75 (d, J=7.86 Hz, 1H), 4.67 (s, 2H)

¹H NMR of the intermediate compound 65:
¹H NMR (300 MHz, CDCl₃): δ 8.43 (d, J=7.32 Hz, 1H), 8.99 (d, J=7.86 Hz, 1H), 7.86 (t, J=7.86 Hz, 1H), 7.66 (d, J=7.86 Hz, 1H), 7.32 (d, J=10.26 Hz, 1H), 7.05 (d, J=10.26 Hz, 1H), 6.57 (s, 1H), 4.79 (m, 1H), 4.74 (s, 2H), 3.96 (s, 3H), 3.91 (s, 3H), 3.73 (s, 3H), 2.68~2.35 (m, 3H), 2.42 (s, 3H), 2.13~2.05 (m, 1H)

¹H NMR of the compound 23:
¹H NMR (300 MHz, CDCl₃): δ 8.50~8.36 (m, 1H), 8.06~7.85 (m, 2H), 7.71-7.52 (m, 2H), 7.25 (d, J=11.34 Hz, 2H), 7.05 (d, J=10.62 Hz, 1H), 6.57 (s, 1H), 5.63 (s, 2H), 4.91~4.79 (m, 1H), 3.96 (s, 3H), 3.91 (s, 3H), 3.73 (s, 3H), 2.70~2.07 (m, 4H), 2.42 (s, 3H)

Example 24

Preparation of 5-Nitrooxymethyl-thiophene-2-carboxylic acid (1,2,3-trimethoxy-10-methylsulfanyl-9-oxo-5,6,7,9-tetrahydro-benzo[α]heptalen-7-yl)-amide

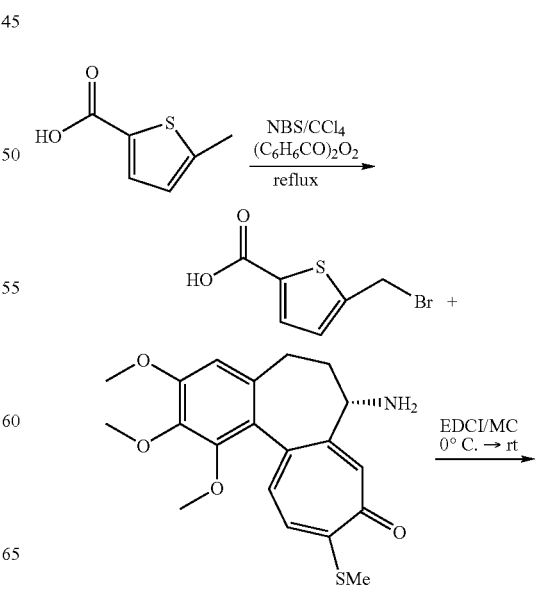

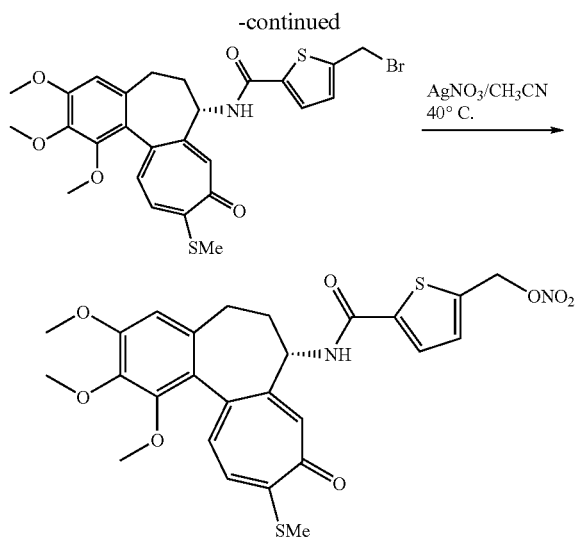
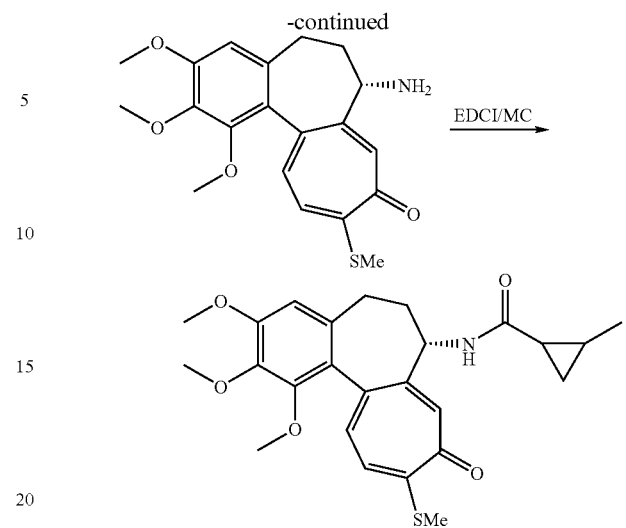

1 g (6.96 mmol) of 5-methyl-2-thiophene-carboxylic acid was subjected to the first step in the reaction of Example 1 to obtain 5-methyl-2-thiophene carboxylic acid methyl ester (Intermediate compound 66, 1 g, Yield: 65%). Then, the intermediate compound 66 was subjected to the sixth and seventh steps in the reaction of Example 1 to obtain the title compound 24 (47 mg, Yield of the third step: 12%).

$^1$H NMR of the intermediate compound 66:

$^1$H NMR (300 MHz, CDCl$_3$): δ 7.51 (d, J=3.66 Hz 1H), 6.96 (d, J=3.66 Hz, 1H), 4.64 (s, 2H)

$^1$H NMR of the intermediate compound 67:

$^1$H NMR (300 MHz, CDCl$_3$): δ 8.26 (s, 1H), 7.57 (s, 1H), 7.51 (d, J=7.86 Hz, 1H), 7.34 (d, J=10.44, 1H), 7.10 (d, 1H), 6.87 (d, 1H), 6.55 (s, 1H), 4.87 (m, 1H), 4.66 (s, 2H), 3.95 (s, 3H), 3.91 (s, 3H), 3.71 (s, 3H), 2.43 (s, 3H), 2.41~2.32 (m, 2H), 2.04 (m, 1H)

$^1$H NMR of the compound 24:

$^1$H NMR (300 MHz, CDCl$_3$): δ 7.81 (d, J=6.60 Hz, 1H), 7.54 (d, J=3.66 Hz, 1H), 7.48 (s, 1H), 7.35 (d, J=10.26 Hz, 2H), 7.10 (d, J=10.62 Hz, 1H), 7.02 (d, J=3.66 Hz, 1H), 6.55 (s, 1H), 5.49 (s, 2H), 4.86~4.83 (m, 1H), 3.96 (s, 3H), 3.91 (s, 3H), 3.75 (s, 3H), 2.58~2.04 (m, 4H), 2.44 (s, 3H)

Example 25

Preparation of 2-Methyl-cyclopropanecarboxylic acid (1,2,3-trimethoxy-10-methylsulfanyl-9-oxo-5,6,7,9-tetrahydro-benzo[α]heptalen-7-yl)-amide

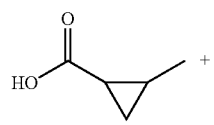

The sixth step in the reaction of Example 1 was carried out to obtain the title compound 25 (357 mg, Yield: 98%) except 2-methyl-cyclopropanecarboxylic acid was used instead of 2-fluoro-3-bromomethyl benzoic acid.

$^1$H NMR (300 MHz, CDCl$_3$): δ 7.31 (d, J=5.85 Hz, 1H), 7.04 (d, J=10.26 Hz, 1H), 6.52 (s, 1H), 6.40 (dd, 1H), 4.66 (m, 1H), 3.92 (s, 3H), 3.89 (s, 3H), 3.63 (s, 3H), 2.60-2.21 (m, 3H), 2.43 (s, 3H), 1.89~1.77 (m, 1H), 1.20 (m, 2H), 1.17 (m, 1H) 1.05 (d, 3H), 0.55 (m, 1H)

Example 26

Preparation of 2-Methyl-cyclopropanecarboxylic acid (10-methanesulfinyl-1,2,3-trimethoxy-10-methylsulfanyl-9-oxo-5,6,7,9-tetrahydro-benzo[α]heptalen-7-yl)-amide

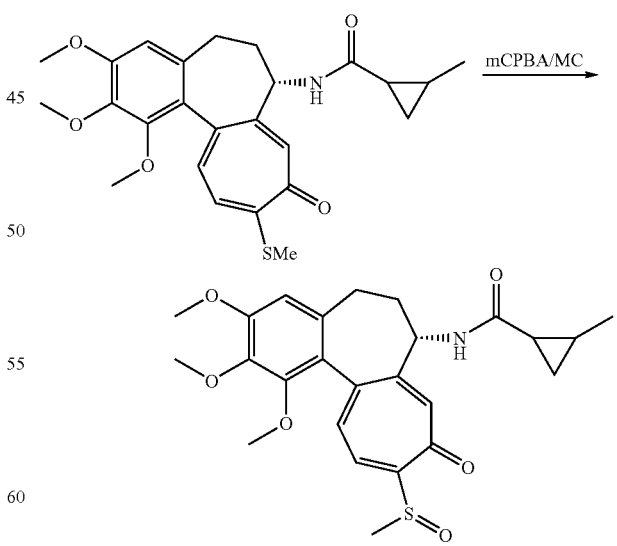

100 mg (0.219 mmol) of 2-methyl-cyclopropanecarboxylic acid (1,2,3-trimethoxy-10-methylsulfanyl-9-oxo-5,6,7,9-tetrahydro-benzo[α]heptalen-7-yl)-amide obtained from Example 25 was dissolved in 5 ml of dichloromethane. 56 mg (0.226 mmol) of m-chloroperbenzoic acid was added thereto and stirred for 2 hours. When the reaction was completed, the mixture was extracted through dichloromethane, washed with saturated sodium bicarbonate solution and then with saturated brine. The organic layer was dried over anhydrous magnesium sulfate, filtered, and then concentrated under reduced pressure. The concentrated product was purified by column chromatography (ethylacetate) to obtain the title compound 26 (84 mg, Yield 82%).

¹H NMR (300 MHz, CDCl₃): δ 8.25 (s, 1H), 7.46 (d, J=4.92 Hz, 1H), 7.34 (d, J=9.52 Hz, 1H), 6.46 (s, 1H), 6.36 (s, 1H), 4.59 (m, 1H), 3.91 (d, J=6.24 Hz, 6H), 3.69 (s, 3H), 3.38 (,3H), 2.43 (m, 2H), 1.81 (m, 1H), 1.20 (m, 3H), 1.07 (m, 4H), 0.58 (m, 1H)

Example 27

Preparation of 2-Methyl-cyclopropanecarboxylic acid (10-methanesulfonyl-1,2,3-trimethoxy-10-methylsulfanyl-9-oxo-5,6,7,9-tetrahydro-benzo[α]heptalen-7-yl)-amide

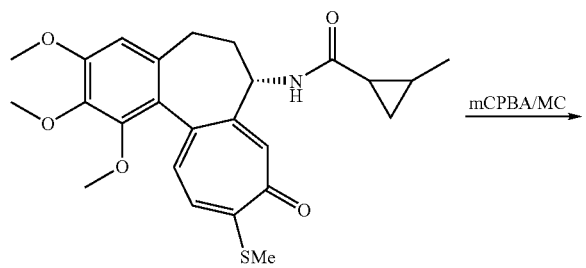

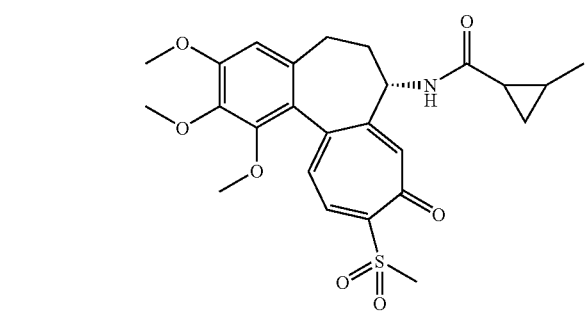

The same method used in Example 26 was carried out to 2-methyl-cyclopropanecarboxylic acid (1,2,3-trimethoxy-10-methylsulfanyl-9-oxo-5,6,7,9-tetrahydro-benzo[α]heptalen-7-yl)-amide obtained from Example 25 to obtain the title compound 27 (87 mg, Yield: 84%) except that 2.5 equivalence of m-chloroperbenzoic acid was used.

¹H NMR (300 MHz, CDCl₃): δ 8.27 (d, J=9.72 Hz, 1H), 7.47 (s, 1H), 7.35 (d, J=9.52 Hz, 1H), 6.46 (s, 1H), 6.35 (dd, 1H), 4.59 (m, 1H), 3.90 (s, 6H), 3.69 (s, 3H), 3.57 (s, 3H), 2.43 (m, 2H), 1.81 (m, 1H), 1.20 (m, 3H), 1.07 (m, 4H), 0.58 (m, 1H)

Example 28

Preparation of 2-Methyl-cyclopropanecarboxylic acid (1,2,3-trimethoxy-10-methylsulfanyl-9-thioxo-5,6,7,9-tetrahydro-benzo[α]heptalen-7-yl)-amide

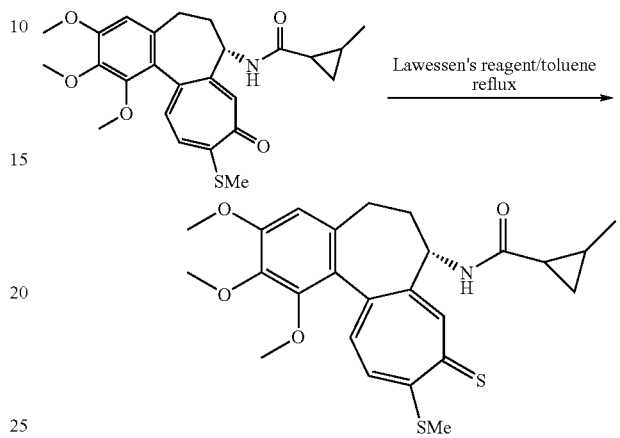

300 mg (0.658 mmol) of 2-methyl-cyclopropanecarboxylic acid (1,2,3-trimethoxy-10-methylsulfanyl-9-oxo-5,6,7,9-tetrahydro-benzo[α]heptalen-7-yl)-amide obtained from Example 25 was dissolved in 10 ml of toluene. 137 mg (0.329 mmol) Lawesson's reagent (2,4-bis(4-methoxyphenyl)-1,3-dithia-2,4-diphosphetane-2,4-disulfide) was added thereto and stirred at temperature of 45° C. to 50° C. for 2 hours. When the reaction was completed, the mixture was cooled to room temperature and filtered. The filtrate was evaporated under reduced pressure, and the concentrated product was purified by the column chromatography (ethylacetate:hexane=1:1) to obtain the title compound 28 (193 mg, Yield: 62%).

¹H NMR (300 MHz, CDCl₃): δ 8.51 (s, 1H), 7.43 (d, J=10.62 1H), 7.32 (d, 1H), 7.15 (s, 1H), 6.54 (s, 1H), 4.62 (m, 1H), 3.93 (s, 6H), 3.67 (s, 3H), 2.50 (s, 3H), 2.46~2.23 (m, 2H), 1.89 (m, 1H), 1.69 (s, 2H), 1.17 (m, 2H), 1.03 (d, 3H), 0.57 (m, 1H)

Example 29

Preparation of 2-Methyl-cyclopropanecarboxylic acid (1,2,3-trimethoxy-9-oxo-5,6,7,9-tetrahydro-benzo[α]heptalen-7-yl)-amide

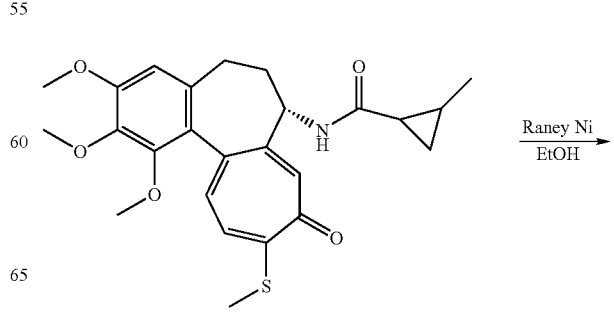

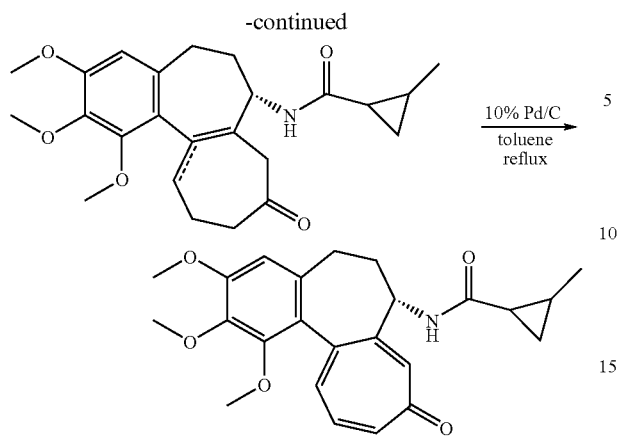

290 mg (0.64 mmol) of 2-methyl-cyclopropanecarboxylic acid (1,2,3-trimethoxy-10-methylsulfanyl-9-oxo-5,6,7,9-tetrahydro-benzo[α]heptalen-7-yl)-amide obtained from Example 25 was dissolved in 60 ml of anhydrous ethanol and stirred. Meanwhile, Raney Ni wet in water was washed with anhydrous ethanol in three times, and wet Raney Ni was added to the mixture. Then, yellow color of the mixture disappeared. After removing Raney Ni, The resulting mixture was concentrated under reduced pressure. The concentrated product was purified by the column chromatography (ethylacetate) to obtain compound 69 (183 mg, Yield: 70%). 59 mg (0.14 mmol) of the compound 69 was dissolved in 20 ml of toluene, and 180 mg of 10% Pd/C was added thereto. The mixture was then heated to reflux under a nitrogen atmosphere for 15 hours. When the reaction was completed, the mixture was cooled to room temperature and Pd/C was removed by filtration through celite. The filtrate was evaporated under reduced pressure and the concentrated product was purified by the column chromatography (dichloromethane:methanol=15:1) to obtain the title compound 29 (18 mg, Yield: 31%).

$^1$H NMR of the compound 29:

$^1$H NMR (300 MHz, CDCl$_3$): δ 7.32 (dd, 1H), 7.24~7.17 (m, 2H), 7.06 (dd, 1H), 6.51 (s, 1H), 4.60 (m, 1H), 3.92 (s, 3H), 3.89 (s, 3H), 3.69 (s, 3H), 2.58~2.41 (m, 3H), 2.34~2.17 (m, 1H), 1.79 (m, 1H), 1.17 (m, 1H), 1.06 (d, J=5.85 Hz, 3H), 0.88~0.86 (m, 1H), 0.57~0.56 (m, 1H)

Example 30

Preparation of (+)-2-Methyl-cyclopropanecarboxylic acid (1,2,3-trimethoxy-10-methylsulfanyl-9-oxo-5,6,7,9-tetrahydro-benzo[α]heptalen-7-yl)-amide

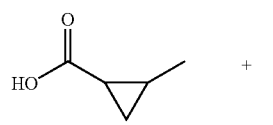 +

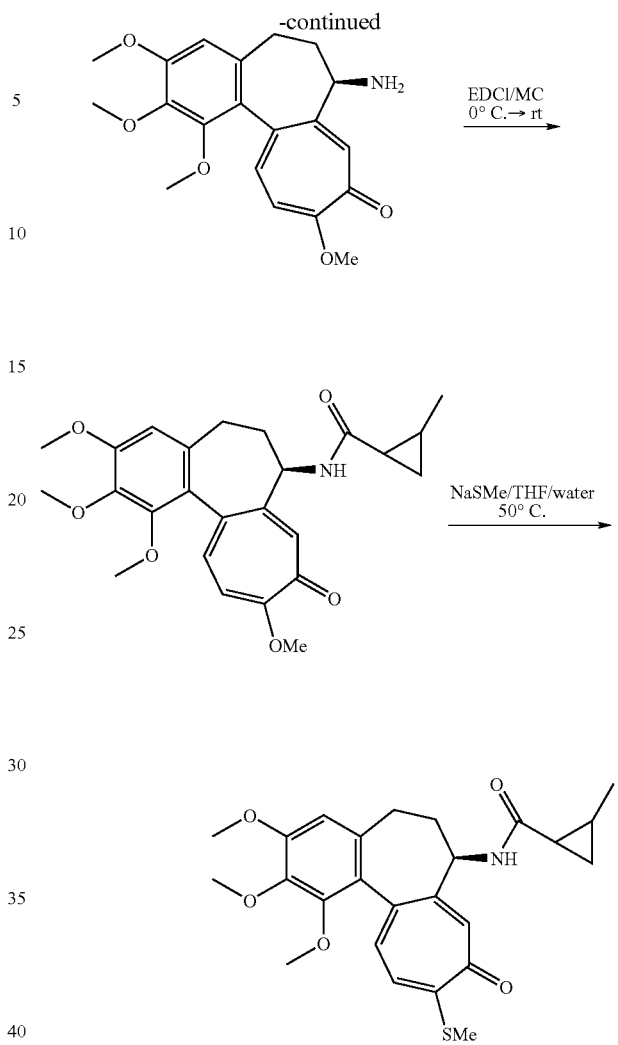

The sixth step in the reaction of Example 1 was carried out to obtain (+)-2-methyl-cyclopropanecarboxylic acid (1,2,3,10-tetramethoxy-9-oxo-5,6,7,9-tetrahydro-benzo[α]heptalen-7-yl)-amide (Compound 71, 690 mg, Yield of the first step: 94%) except that 171 mg (1.679 mmol) of 2-methyl-cyclopropanecarboxylic acid and 600 mg (1.679 mmol) of (+)-deacetyl colchicine were used instead of 2-fluoro-3-bromomethyl benzoic acid and (−)-thiodeacetyl colchicine, respectively. Next, 552 mg (1.256 mmol) of compound 71 was dissolved in a mixed solution of tetrahydrofuran (10 ml) and water (20 ml). 188 mg (2.55 mmol) of sodium thiomethoxide was added thereto and stirred at 50° C. for 10 hours. When the reaction was completed, an organic layer was extracted through dichloromethane, dried over anhydrous magnesium sulfate and filtered. The filtrate was evaporated under reduced pressure, and the concentrated product was purified by the column chromatography (ethylacetate) to obtain the title compound 30 (360 mg, Yield of the second step: 59%).

$^1$H NMR of the compound 30:

$^1$H NMR (300 MHz, CDCl$_3$): δ 7.37 (s, 1H), 7.30 (d, 1H), 7.06 (d, 1H), 6.52 (s, 1H), 4.69 (m, 1H), 3.94 (s, 6H), 3.86 (s, 3H), 2.52 (s, 3H), 2.43 (m, 2H), 1.83 (m, 1H), 1.20 (m, 3H), 1.03 (m, 4H), 0.58 (m, 1H)

Example 31

Preparation of 2-Methyl-cyclopropanecarboxylic acid (1-hydroxy-2,3-dimethoxy-10-methylsulfanyl-9-oxo-5,6,7,9-tetrahydro-benzo[α]heptalen-7-yl)-amide

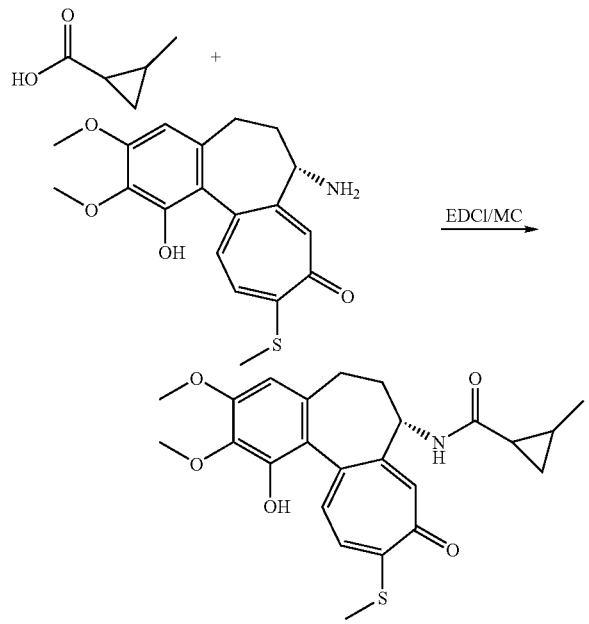

The sixth step in the reaction of Example 1 was carried out to obtain the title compound 31 (66 mg, Yield: 85%) except that (−)-1-hydroxy thiodeacetyl colchicine was used instead of (−)-thiodeacetyl colchicine.

$^1$H NMR (300 MHz, CDCl$_3$): δ 7.46 (m, 1H), 7.24~7.18 (m, 2H), 6.39 (s, 1H), 4.63 (m, 1H), 3.90 (m, 6H), 2.47 (s, 3H), 2.32 (m, 3H), 1.92 (m, 1H), 1.36~1.21 (m, 3H) 1.09 (d, J=5.49 Hz, 3H), 0.56 (s, 1H)

Example 32

Preparation of 2-Methyl-cyclopropanecarboxylic acid (2-hydroxy-1,3-dimethoxy-10-methylsulfanyl-9-oxo-5,6,7,9-tetrahydro-benzo[α]heptalen-7-yl)-amide

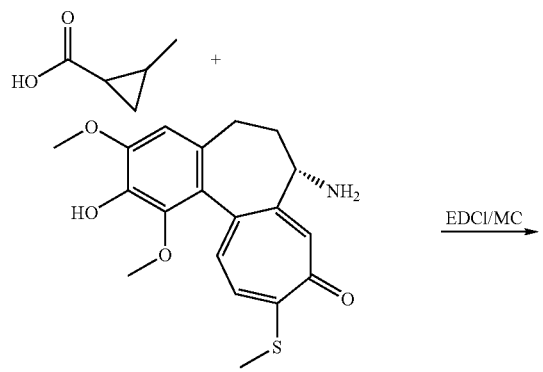

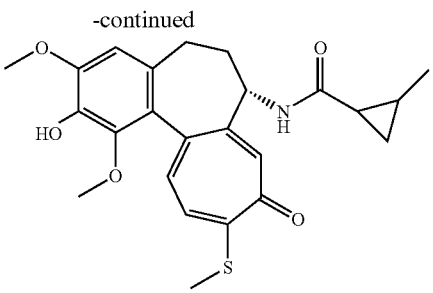

The sixth step in the reaction of Example 1 was carried out to obtain the title compound 32 (369 mg, Yield: 67%) except that (−)-2-hydroxy thiodeacetyl colchicine was used instead of (−)-thiodeacetyl colchicine.

$^1$H NMR (300 MHz, CDCl$_3$): δ 7.35 (s, 1H), 7.29 (d, J=10.35 Hz, 1H), 7.05 (d, J=10.44 Hz, 1H), 6.50 (s, 1H), 6.36 (d, J=7.32 Hz, 1H), 4.65 (m, 1H), 3.92 (s, 3H), 3.61 (s, 3H), 2.43 (s, 3H), 2.52~2.23 (m, 3H), 1.82~1.80 (m, 1H), 1.46~1.43 (m, 1H), 1.36~1.20 (m, 1H), 1.06 (d, J=5.88 Hz, 3H), 0.77~0.71 (m, 1H), 0.56~0.50 (m, 1H)

Example 33

Preparation of 3-Methyl-aziridine-2-carboxylic acid (1,2,3-trimethoxy-10-methylsulfanyl-9-oxo-5,6,7,9-tetrahydro-benzo[α]heptalen-7-yl)-amide

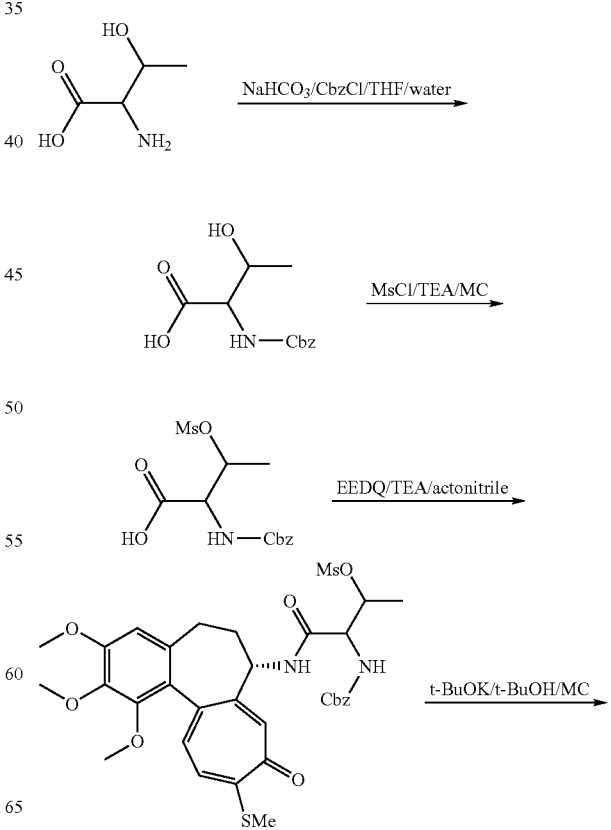

-continued

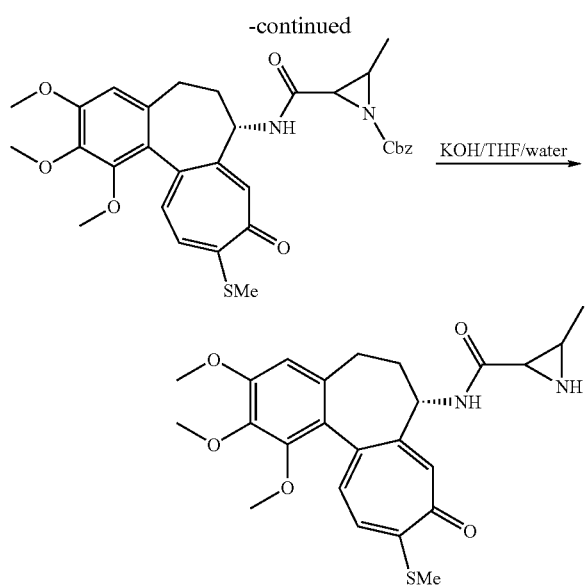

2.4 g (20 mmol) of L-threonine and 3.4 g (40 mmol) of sodium bicarbonate were dissolved in 35 ml of water. 3.69 g (21 mmol) of chlorobenzyloxyformate was added thereto and stirred at room temperature for one day. When the reaction was completed, the reaction mixture was concentrated under reduced pressure. The residue was acidified to a pH of 3 by 10% citric acid, and extracted with ethylacetate. The organic layer obtained was washed with saturated brine, dried over anhydrous magnesium sulfate and filtered. The filtrate was concentrated under reduced pressure to obtain intermediate compound 68 (4.72 g, Yield of the first step: 93%). 200 mg (0.790 mmol) of the intermediate compound 68 was dissolved in 10 ml of acetonitrile. Then, 212 mg (0.848 mmol) of EEDQ, 289 mg (0.774 mmol) of (−)-thiodeacetyl colchicine, and 0.11 ml (0.774 mmol) of triethylamine were sequentially added thereto, and stirred for one day. When the reaction was completed, the mixture was extracted with dichloromethane and dried over anhydrous magnesium sulfate, and then concentrated under reduced pressure. The concentrated product was purified by the column chromatography (ethylacetate:hexane=2:1) to obtain intermediate compound 69 (116 mg, Yield of the second step: 48%). Next, 2.54 g (4.184 mmol) of the intermediate compound 69 was dissolved in 70 ml of dichloromethane. 2.97 ml (20.92 mmol) of triethylamine was first added thereto dropwise and then 0.43 ml (5.440 mmol) of methane sulfonyl chloride was slowly added dropwise at 0° C. For the reaction, the mixture was stirred for two hours, and then extracted through dichloromethane and dried over anhydrous magnesium sulfate, and then concentrated under reduced pressure to obtain intermediate compound 70 (2.87 g, Yield of the third step: 100%). 2.87 g (4.184 mmol) of the intermediate compound 70 was dissolved in a mixed solution of 60 ml of t-butanol and 10 ml of dichloromethane. To this mixture, 502 mg (4.337 mmol) of t-potassium butoxide was added and stirred at room temperature for one day. When the reaction was completed, the organic layer in the mixture was extracted through dichloromethane, washed with saturated brine, and dried over anhydrous magnesium sulfate, and then concentrated under reduced pressure. The concentrated product was purified by the column chromatography (ethylacetate:hexane: 2:1) to obtain intermediate compound 71 (938 mg, Yield of the fourth step: 38%). 1.62 g (2.744 mmol) of the intermediate compound 71 was dissolved in a mixed solution of tetrahydrofuran (20 ml) and water (20 ml). 0.308 g (5.490 mmol) of potassium hydroxide was added thereto and stirred at room temperature for one day. When the reaction was completed, an organic layer was extracted through dichloromethane, washed with saturated brine, dried over anhydrous magnesium sulfate, and then concentrated under reduced pressure. The concentrated product was purified by the column chromatography (dichloromethane:methanol=20:1) to obtain the title compound 33 (726 mg, Yield of the fifth step: 9%).

¹H NMR of the intermediate compound 68:
¹H NMR (300 MHz, CDCl₃): δ 7.37~7.22 (m, 1H), 5.97 (d, J=8.79 Hz, 1H), 5.78 (br, 1H), 5.09 (d, J=3.48, 2H), 4.41~4.20 (m, 2H), 1.19 (d, J=6.00 Hz, 3H)

¹H NMR of the intermediate compound 69:
¹H NMR (300 MHz, CDCl₃): δ 7.40~7.26 (m, 6H), 7.06 (d, J=10.62 Hz, 1H), 6.53 (s, 1H), 5.68 (d, J=7.89 Hz, 1H), 5.08 (s, 2H), 4.57 (m, 1H), 4.29~4.21 (m, 1H), 3.94 (s, 3H), 3.90 (s, 3H), 3.65 (s, 3H), 3.67~3.63 (m, 1H), 2.53~2.38 (m, 2H), 2.48 (s, 3H), 2.25~2.15 (m, 1H), 1.90~1.78 (m, 1H), 1.15 (d, J=6.42, 3H)

¹H NMR of the intermediate compound 70:
¹H NMR (300 MHz, CDCl₃): δ 7.42~7.25 (m, 5H), 7.04 (d, J=10.62 Hz, 1H), 6.54 (s, 1H), 5.59 (d, J=7.35 Hz, 1H), 5.16~5.03 (m, 3H), 4.63 (m, 1H), 3.94 (s, 3H), 3.91 (s, 3H), 3.64 (s, 3H), 3.00~2.93 (m, 2H), 2.53~2.40 (m, 2H), 2.41 (s, 3H), 2.21~2.17 (m, 1H), 2.00~1.93 (m, 1H), 1.31 (m, 3H)

¹H NMR of the intermediate compound 71:
¹H NMR (300 MHz, CDCl₃): δ 7.43~7.34 (m, 4H), 7.27 (d, J=10.44 Hz, 1H), 7.17 (s, 1H), 7.03 (d, J=10.62 Hz, 1H), 6.77 (d, 4.53 J=7.68 Hz, 1H), 6.52 (s, 1H), 5.19 (d, J=5.31 Hz, 2H), 4.56 (m, 1H), 3.94 (s, 3H), 3.90 (s, 3H), 3.65 (s, 3H), 3.11 (d, J=6.96 Hz, 1H), 2.80~2.76 (m, 1H), 2.61~2.45 (m, 2H), 2.25~1.752 (m, 2H), 1.22 (d, J=5.67 Hz, 3H)

¹H NMR of the compound 33:
¹H NMR (300 MHz, CDCl₃): δ 7.32~7.17 (m, 2H), 7.08~7.02 (m, 1H), 6.53 (s, 1H), 4.53 (m, 1H), 3.94 (s, 3H), 3.90 (s, 3H), 3.66 (s, 3H), 2.70 (d, 1H), 2.60~2.35 (m, 2H), 2.43 (s, 3H), 2.20~1.82 (m, 3H), 1.12 (d, J=5.70 Hz, 3H)

Example 34

Preparation of 1,3-Dimethyl-aziridine-2-carboxylic acid (1,2,3-trimethoxy-10-methylsulfanyl-9-oxo-5,6,7,9-tetrahydro-benzo[α]heptalen-7-yl)-amide

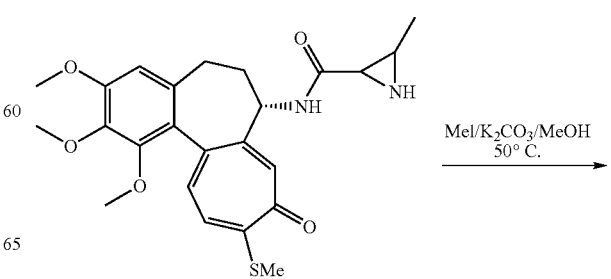

-continued

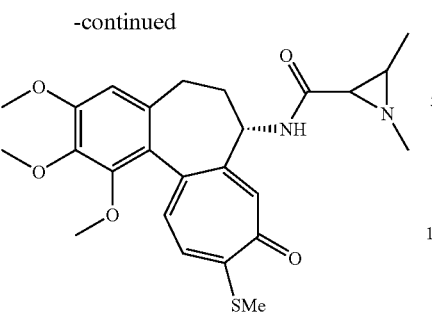

100 mg (0.219 mmol) of 3-methyl-aziridine-2-carboxylic acid (1,2,3-trimethoxy-10-methylsulfanyl-9-oxo-5,6,7,9-tetrahydro-benzo[α]heptalen-7-yl)-amide obtained from Example 33 was dissolved in 5 ml of methanol. Next, 30 mg (0.219 mmol) of potassium carbonate and 0.14 ml (2.190 mmol) of iodomethane were added thereto and stirred at 50° C. for one day. When the reaction was completed, an organic layer was extracted through dichloromethane, washed with saturated brine, dried over anhydrous magnesium sulfate, and then concentrated under reduced pressure. The concentrated product was purified by the column chromatography (ethylacetate) to obtain the title compound 34 (66 mg, Yield: 65%).

$^1$H NMR (300 MHz, CDCl$_3$): δ 7.41 (br s, 1H), 7.23~7.09 (m, 3H), 6.75 (s, 1H), 4.50 (m, 1H), 3.91 (s, 3H), 3.83 (s, 3H), 3.60 (s, 3H), 2.67~2.56 (m, 1H), 2.45~2.35 (m, 1H), 2.43 (s, 3H), 2.36 (s, 3H), 2.15~2.05 (m, 2H), 1.95~1.90 (m, 1H), 1.75~1.66 (m, 1H), 1.02 (d, J=5.67 Hz, 3H)

Example 35

Preparation of But-2-enoic acid (1,2,3-trimethoxy-10-methylsulfanyl-9-oxo-5,6,7,9-tetrahydro-benzo[α]heptalen-7-yl)-amide

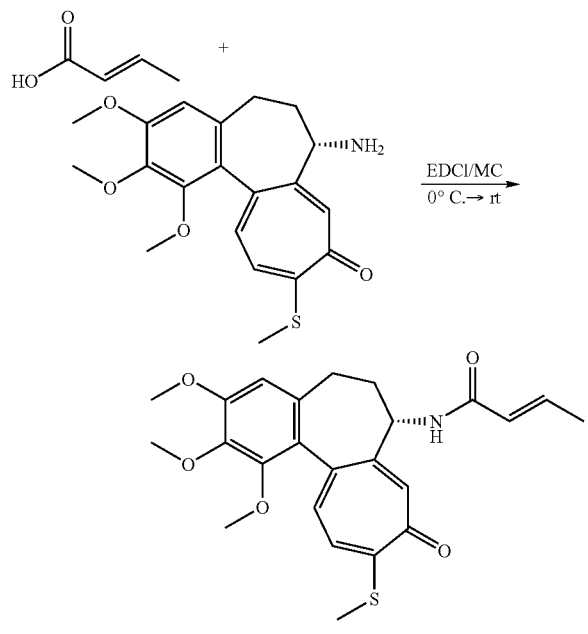

The sixth step in the reaction of Example 1 was carried out to obtain the title compound 35 (326 mg, Yield: 92%) except that crotonic acid was used instead of 2-fluoro-3-bromomethyl benzoic acid.

$^1$H NMR (300 MHz, CDCl$_3$): δ 7.34~7.30 (m, 2H), 7.07 (d, J=10.41 Hz, 1H), 6.97 (d, J=7.14 Hz, 1H), 6.83~6.71 (m, 1H), 6.54 (s, 1H), 5.91 (dd, 1H), 4.77~4.68 (m, 1H), 3.95 (s, 3H), 3.91 (s, 3H), 3.68 (s, 3H), 2.44 (s, 3H), 2.57~2.18 (m, 3H), 1.91~1.83 (m, 1H), 1.79 (d, 3H)

Example 36

Preparation of But-2-enoic acid (10-methanesulfonyl-1,2,3-trimethoxy-9-oxo-5,6,7,9-tetrahydro-benzo[α]heptalen-7-yl)-amide

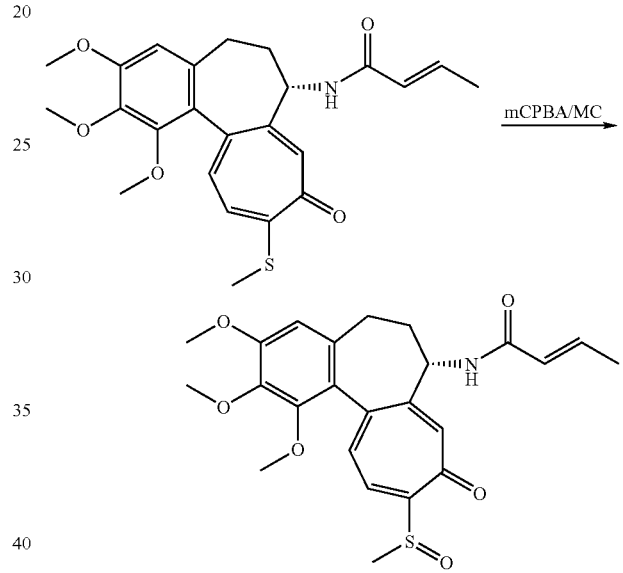

But-2-enoic acid (1,2,3-trimethoxy-10-methylsulfanyl-9-oxo-5,6,7,9-tetrahydro-benzo[α]heptalen-7-yl)-amide obtained from Example 35 was subjected to the same method described in Example 26 to obtain the title compound 36 (85 mg, Yield: 82%).

$^1$H NMR (300 MHz, CDCl$_3$): δ 7.87 (d, J=9.72 Hz, 1H), 7.49 (d, J=9.68 Hz, 1H), 6.81 (m, 1H), 6.54 (s, 1H), 6.33 (d, J=6.57 Hz, 1H), 5.87 (m, 1H), 4.67 (m, 1H), 3.94 (s, 3H), 3.91 (s, 3H), 3.72 (s, 3H), 2.91 (s, 3H), 2.66~2.21 (m, 3H), 1.89~1.77 (m, 1H), 1.84 (d, J=6.78 Hz, 3H)

Example 37

Preparation of Pent-3-enoic acid (1,2,3-trimethoxy-10-methylsulfanyl-9-oxo-5,6,7,9-tetrahydro-benzo[α]heptalen-7-yl)-amide

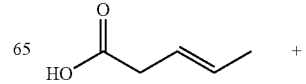

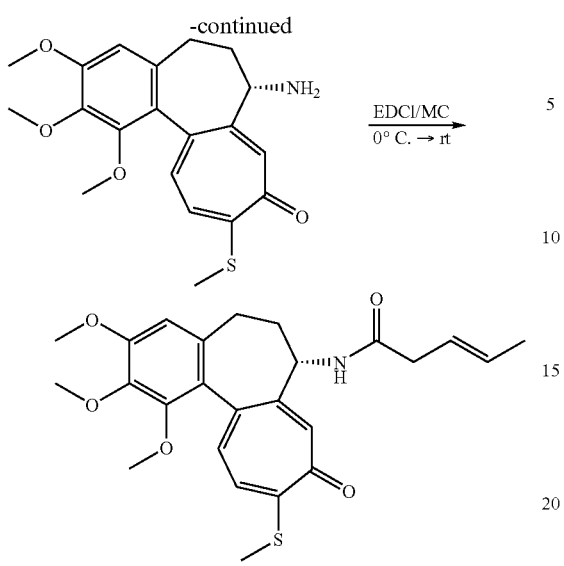

The sixth step in the reaction of Example 1 was carried out to obtain the title compound 37 (711 mg, Yield: 78%) except pent-3-enoic acid was used instead of 2-fluoro-3-bromomethyl benzoic acid.

$^1$H NMR (300 MHz, CDCl$_3$): δ 7.28 (d, 1H), 7.15 (s, 1H), 7.04 (d, J=10.44, 1H), 6.52 (s, 1H), 6.21 (d, J=6.78 Hz, 1H), 5.70~5.50 (m, 1H), 4.63 (m, 1H), 3.93 (s, 3H), 3.90 (s, 3H), 3.65 (s, 3H), 2.94 (d, J=7.59 Hz, 2H), 2.65~2.27 (m, 3H). 2.46 (s, 3H), 1.79 (m, 1H), 1.72 (d, J=6.24 Hz, 3H)

Example 38

Preparation of But-3-enoic acid (1,2,3-trimethoxy-10-methylsulfanyl-9-oxo-5,6,7,9-tetrahydro-benzo[α]heptalen-7-yl)-amide

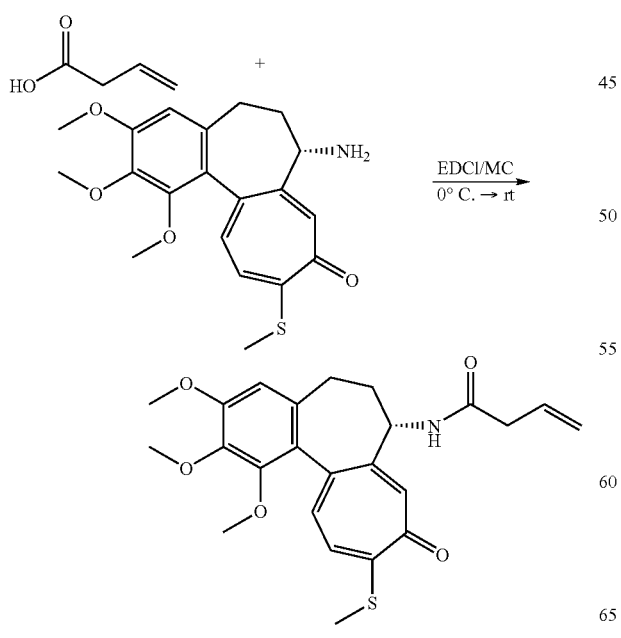

The sixth step in the reaction of Example 1 was carried out to obtain the title compound 38 (950 mg, Yield: 96%) except that but-3-enoic acid was used instead of 2-fluoro-3-bromomethyl benzoic acid.

$^1$H NMR (300 MHz, CDCl$_3$): δ 7.29 (d, J=10.44 Hz, 1H), 7.24 (s, 1H), 7.05 (d, J=10.62 Hz, 1H), 6.65 (d, J=7.14 Hz, 1H), 6.52 (s, 1H), 5.92 (m, 1H), 5.29 (s, 1H), 5.25-5.18 (m, 2H), 4.65 (m, 1H), 3.93 (s, 3H), 3.89 (s, 3H), 3.66 (s, 3H), 3.02 (d, J=7.14 Hz, 2H), 2.58~2.17 (m, 3H), 2.43 (s, 3H), 1.89~1.77 (m, 1H)

Example 39

Preparation of Hexa-2,4-dienoic acid (1,2,3-trimethoxy-10-methylsulfanyl-9-oxo-5,6,7,9-tetrahydro-benzo[α]heptalen-7-yl)-amide

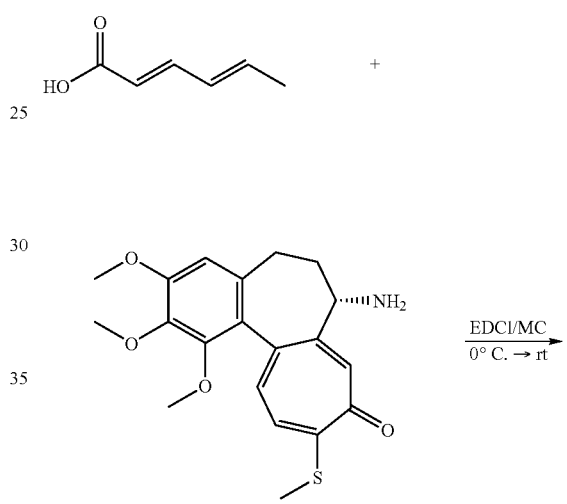

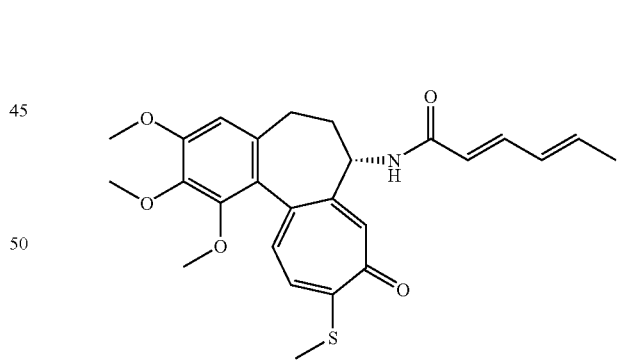

The sixth step in the reaction of Example 1 was carried out to obtain the title compound 39 (723 mg, Yield: 62%) except that hexa-2,4-dienoic acid was used instead of 2-fluoro-3-bromomethyl benzoic acid.

$^1$H NMR (300 MHz, CDCl$_3$): δ 7.33 (s, 1H), 7.28 (d, 1H), 7.12 (d, J=10.62 Hz, 1H), 7.07 (d, J=10.62, 1H), 6.94 (d, J=6.96 Hz, 1H), 6.53 (s, 1H), 6.16~5.94 (m, 2H), 5.85 (d, J=15.00 Hz, 1H), 4.74 (m, 1H), 3.94 (s, 3H), 3.90 (s, 3H), 3.69 (s, 3H), 2.60-2.25 (m, 3H). 2.43 (s, 3H), 1.79 (m, 1H), 1.78 (d, J=6.21 Hz, 3H)

Example 40

Preparation of 2-Chloro-3-methyl-N-(3,9,10,11-tetramethoxy-6,7-dihydro-5H-dibenzo[a,c]cyclohepten-5-yl)-benzamide

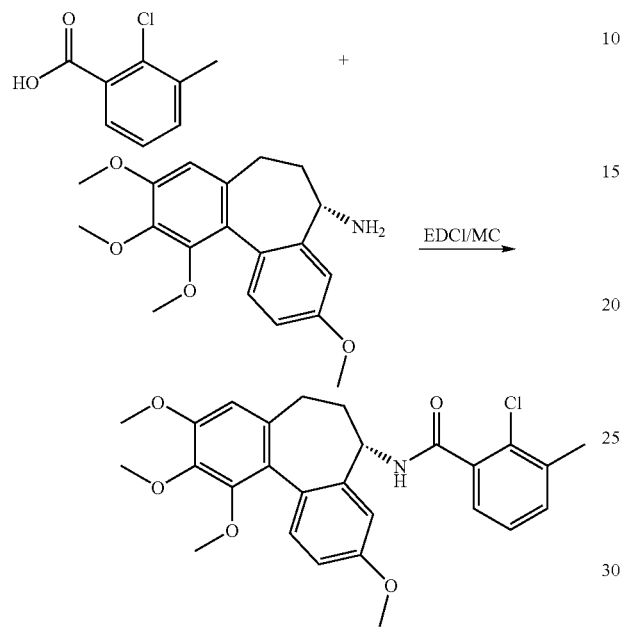

The second step in the reaction of Example 10 was carried out to obtain the title compound 40 (50 mg, Yield: 57%) except that (−)-7-deacetyl-9-methoxy allocolchicine was used instead of (−)-thiodeacetyl colchicine.

$^1$H NMR (300 MHz, CDCl$_3$): δ 7.48~7.41 (m, 2H), 7.32 (d, 1H), 7.24 (d, 1H), 7.04 (d, 1H), 6.90 (dd, 1H), 6.60 (s, 1H), 6.35 (d, 1H), 5.20~5.00 (m, 1H), 3.95 (s, 3H), 3.92 (s, 3H), 3.86 (s, 3H), 3.58 (s, 3H), 2.53~2.30 (m, 3H), 2.44 (s, 3H), 2.00~1.80 (m, 1H)

Example 41

Preparation of 2-Methyl-cyclopropanecarboxylic acid (3,9,10,11-tetramethoxy-6,7-dihydro-5H-dibenzo[a,c]cyclohepten-5-yl)-amide

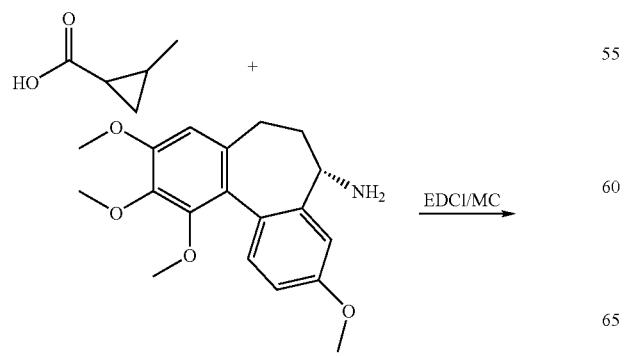

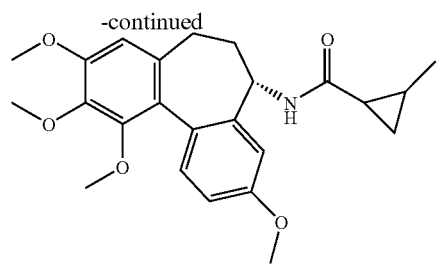

The same method used in Example 25 was carried out to obtain the title compound 41 (95 mg, Yield: 76%) except that (−)-7-deacetyl-9-methoxy allocolchicine was used instead of (−)-thiodeacetyl colchicine.

$^1$H NMR (300 MHz, CDCl$_3$): δ 7.43 (dd, 1H), 6.89~6.86 (m, 2H), 6.56 (s, 1H), 5.92 (d, 1H), 4.75~4.90 (m, 1H), 3.91 (s, 3H), 3.89 (s, 3H), 3.87 (s, 3H), 3.49 (s, 3H), 2.49~2.32 (m, 3H), 1.90~1.75 (m, 1H), 1.48~1.41 (m, 1H), 1.36~1.20 (m, 1H), 1.12 (d, 3H), 0.76~0.72 (m, 1H), 0.57 (m, 1H)

Example 42

Preparation of 2-Chloro-N-(3-methanesulfonyl-9,10,11-trimethoxy-6,7-dihydro-5H-dibenzo[a,c]cyclohepten-5-yl)-3-methyl-benzamide

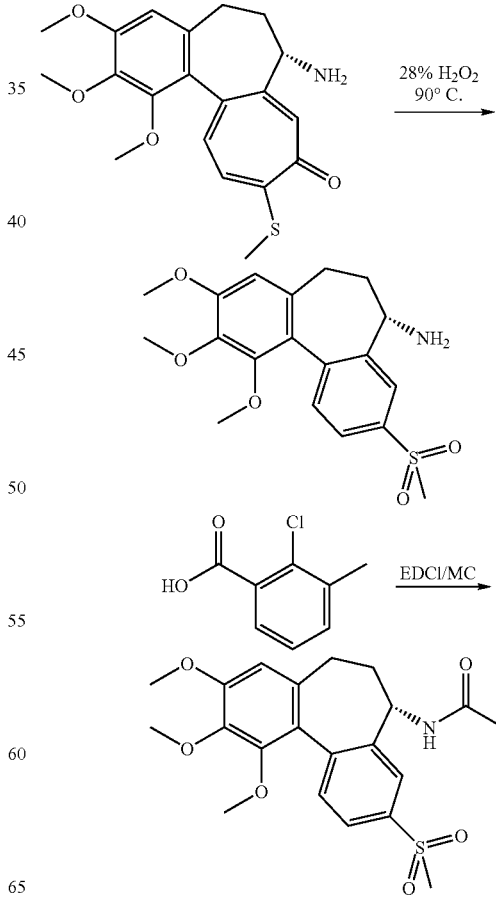

3 g (8.03 mmol) of (−)-thiodeacetyl colchicine was mixed with 100 ml of 28% hydrogen peroxide, and stirred. The mixture was then refluxed under heating at 90° C. After 7 hours, it was cooled at room temperature and extracted with dichloromethane to remove by-products. An aqueous layer was neutralized with sodium bicarbonate solution and extracted through dichloromethane. An organic layer thusly obtained was dried over anhydrous magnesium sulfate, filtered, and then concentrated under reduced pressure to obtain (−)-9-methanesulfonylacetyl allocolchicine (Intermediate compound 72, 0.691 g, 23%). Next, the second step in the reaction of Example 10 was carried out to obtain the title compound 42 (47 mg, Yield: 42%) except that the intermediate compound 72 was used instead of (−)-thiodeacetyl colchicine.

$^1$H NMR of the intermediate compound 72:
$^1$H NMR (300 MHz, CDCl$_3$): δ 8.25 (s, 1H), 7.89 (dd, 1H), 7.63 (d, 1H), 6.61 (s, 1H), 3.93 (s, 3H), 3.91 (s, 3H), 3.66 (s, 3H), 3.15 (s, 3H), 2.49~2.45 (m, 2H), 2.24~2.18 (m, 1H), 1.79~1.77 (m, 1H)

$^1$H NMR of the compound 42:
$^1$H NMR (300 MHz, CDCl$_3$): δ 8.13 (s, 1H), 7.90 (dd, 1H), 7.72 (d, 1H), 7.39~7.21 (m, 3H), 6.63 (s, 1H), 6.43 (d, J=7.86 Hz, 1H), 5.08 (m, 1H), 3.95 (s, 3H), 3.94 (s, 3H), 3.67 (s, 3H), 3.13 (s, 3H), 2.58~2.29 (m, 3H), 2.45 (s, 3H), 1.99 (m, 1H)

Example 43

Preparation of 2-Methyl-cyclopropanecarboxylic acid (3-methanesulfonyl-9,10,11-trimethoxy-6,7-dihydro-5H-dibenzo[a,c]cyclohepten-5-yl)-amide

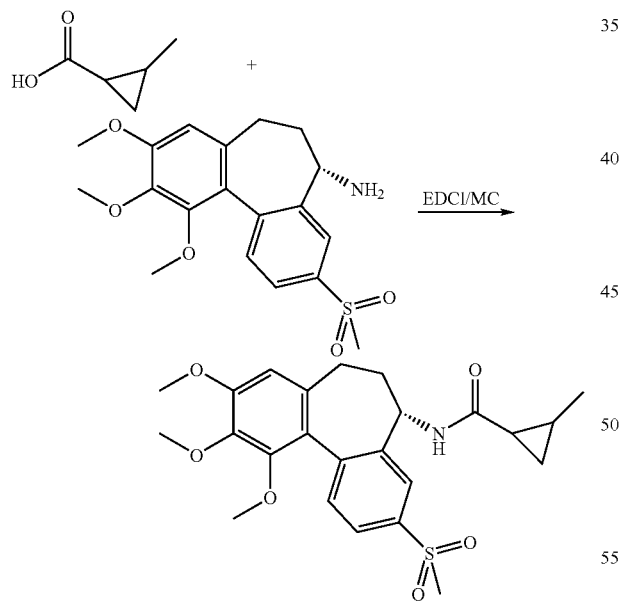

The same method used in Example 25 was carried out to obtain the title compound 43 (85 mg, Yield: 71%) except that (−)-9-methanesulfonylacetyl allocolchicine obtained from Example 42 was used instead of (−)-thiodeacetyl colchicine.

$^1$H NMR (300 MHz, CDCl$_3$): δ 7.89 (dd, 2H), 7.68 (d, 1H), 6.59 (s, 1H), 6.03 (d, J=7.5 Hz, 1H), 4.87~4.85 (m, 1H), 3.95 (s, 3H), 3.94 (s, 3H), 3.54 (s, 3H), 3.15 (s, 3H), 2.51~2.49 (m, 2H), 1.83 (m, 1H), 1.47~1.41 (m, 1H), 1.36~1.22 (m, 1H), 1.13 (d, 3H), 0.77~0.73 (m, 1H), 0.61 (m, 1H)

Example 44

Preparation of But-2-enoic acid (3-methanesulfonyl-9,10,11-trimethoxy-6,7-dihydro-5H-dibenzo[a,c]cyclohepten-5-yl)-amide

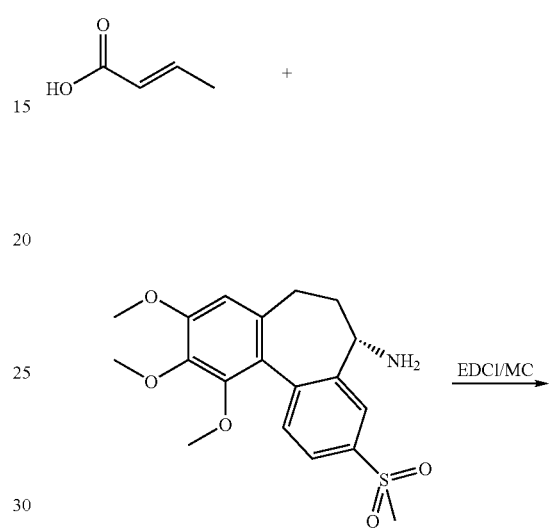

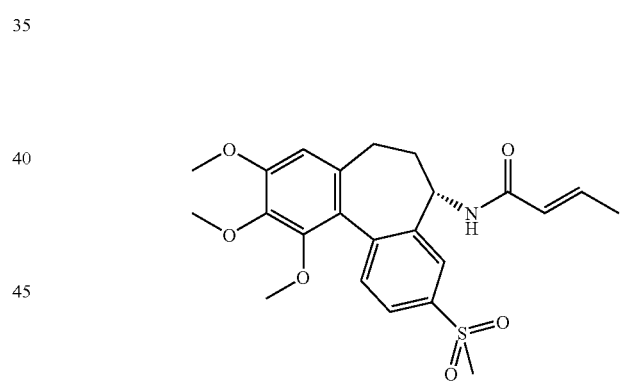

The same method used in Example 35 was carried out to obtain the title compound 44 (109 mg, Yield: 61%) except that (−)-9-methanesulfonylacetyl allocolchicine obtained from Example 42 was used instead of (−)-thiodeacetyl colchicine.

$^1$H NMR (300 MHz, CDCl$_3$): δ 7.87~7.85 (m, 2H), 7.69 (d, J=8.61 Hz, 1H), 6.87~6.80 (m, 1H), 6.60 (s, 1H), 5.60~5.87 (m, 2H), 4.94 (m, 1H), 3.94 (s. 3H), 3.92 (s, 3H), 3.59 (s. 3H), 3.12 (s, 3H), 2.52~2.40 (m, 2H), 2.30~2.12 (m, 1H), 1.88 (dd, 3H), 1.89~1.86 (m, 1H).

Table 1 shows the list of the compounds synthesized in accordance with the method of the present invention in addition to the compounds of the above Examples.

TABLE 1

(Compound 45–Compound 84)

| Compound | $^1$H NMR (300 MHz): δ |
|---|---|
| Compound 45 | $^1$H NMR (300 MHz, CDCl$_3$): δ 8.71(s, 1H), 7.45(m, 1H), 7.35~7.29(m, 2H), 7.17(d, 1H), 7.11(s, 1H), 6.62~6.58(m, 2H), 4.82(m, 1H), 3.95(s, 6H), 3.73(s, 3H), 2.61~2.29(m, 6H), 1.98(d, 2H) |
| Compound 46 | $^1$H NMR (300 MHz, CDCl$_3$): δ 8.00(d, J=7.32Hz, 1H), 7.56~7.51(m, 1H), 7.32(d, J=10.44Hz, 1H), 7.24~7.13(m, 3H), 7.05(d, J=10.62Hz, 1H), 6.57(S, 1H), 5.37(s, 2H), 4.89~4.77(m, 1H), 3.96(s, 3H), 3.91(s, 3H), 3.73(s, 3H), 2.61~2.36(m, 3H), 2.43(s, 3H), 2.02~1.94(m, 1H) |
| Compound 47 | $^1$H NMR (300 MHz, CDCl$_3$): δ 9.06(d, J=7.14Hz, 1H), 7.81–7.76(m, 2H), 7.43(d, J=10.44Hz, 3H), 7.18(d, J=10.44Hz, 1H), 6.85(t, J=8.97Hz, 1H), 6.57(s, 1H), 5.36~5.07(AB quartet, 2H), 4.98–4.87(m, 1H), 3.98(s, 3H), 3.92(s, 3H), 3.76(s, 3H), 2.60~2.30(m, 4H), 2.45(s, 3H) |
| Compound 48 | $^1$H NMR (300 MHz, CDCl$_3$): δ 7.46(s, 1H), 7.33~7.26(m, 3H), 7.17(d, J=6.03, 1H), 7.06(d, J=10.44, 1H), 6.77(d, J=6.78, 1H), 6.57(s, 1H), 4.90~4.80(m, 1H), 3.96(s, 3H), 3.92(s, 3H), 3.72(s, 3H), 2.65~2.20(m, 3H), 2.44(s, 3H), 2.31(s, 3H), 2.00~1.85(m, 1H) |

TABLE 1-continued (Compound 45–Compound 84)

| Compound | $^1$H NMR (300 MHz): δ |
|---|---|
| Compound 49 | $^1$H NMR (300 MHz, CDCl$_3$): δ 7.69(s, 1H), 7.46~7.39(m, 2H), 7.33(s, 1H), 7.31(d, J=10.62Hz, 1H), 7.06(d, J=10.26Hz, 1H), 7.00(d, J=7.14Hz, 1H), 6.57(S, 1H), 5.37(s, 2H), 4.91~4.82(m, 1H), 3.96(s, 3H), 3.92(s, 3H), 3.72(s, 3H). 2.58~2.31(m, 3H), 2.44(s, 3H), 1.98~1.88(m, 1H) |
| Compound 50 | $^1$H NMR (300 MHz, CDCl$_3$): δ 8.72(d, J=7.02Hz, 1H), 7.91(s, 1H), 7.23(d, 1H), 7.64(s, 1H), 7.41(d, J=10.44Hz, 1H), 7.22(d, J=10.44Hz, 1H), 7.15(d, J=10.62Hz, 1H), 6.57(S, 1H), 5.43~5.18(AB quartet, 2H), 4.98–4.86(m, 1H), 3.97(s, 3H), 3.91(s, 3H), 3.75(s, 3H), 2.61~2.23(m, |
| Compound 51 | $^1$H NMR (300 MHz, CDCl$_3$): δ 7.63(d, J=8.22Hz, 1H), 7.57(s, 1H), 7.37(s, 1H), 7.33~7.25(m, 2H), 7.06(d, J=10.44Hz, 1H), 6.73(d, J=6.96Hz, 1H), 6.57(S, 1H), 5.35(s, 2H), 4.90~4.83(m, 1H), 3.96(s, 3H), 3.92(s, 3H), 3.72(s, 3H). 2.64~2.35(m, 3H), 2.44(s, 3H), 2.00–1.88(m, |
| Compound 52 | $^1$H NMR (300 MHz, CDCl$_3$): δ 8.62(d, J=7.14Hz, 1H), 7.91(s, 1H), 7.66~7.61(m, 2H), 7.44~7.38(m, 2H), 7.15(d, J=10.80Hz, 1H), 6.57(S, 1H), 5.43~5.20(AB quartet, 2H), 4.94~4.85(m, 1H), 3.97(s, 3H), 3.91(s, 3H), 3.75(s, 3H), 2.65~2.20(m, 4H), 2.44(s, 3H) |

TABLE 1-continued (Compound 45–Compound 84)

| Compound | $^1$H NMR (300 MHz): δ |
|---|---|
| Compound 53 | $^1$H NMR (300 MHz, CDCl$_3$): δ 7.85(d, J=8.07Hz, 1H), 7.48(s, 1H), 7.42(s, 1H), 7.30(d, J=10.44Hz, 1H), 7.11~7.00(m, 3H), 6.57(S, 1H), 5.33(s, 2H), 4.95~4.83(m, 1H), 3.96(s, 3H), 3.93(s, 3H), 3.73(s, 3H). 2.67~2.41(m, 3H), 2.43(s, 3H), 2.15~1.94(m, 1H) |
| Compound 54 | $^1$H NMR (300 MHz, CDCl$_3$): δ 8.84(d, 1H), 7.86(s, 1H), 7.69(s, 1H), 7.66(s, 1H), 7.46(d, J=10.35Hz, 1H), 7.41(d, J=10.44Hz, 1H), 7.16(d, J=10.44, 1H), 6.57(s, 1H), 5.32~5.13(AB quartet, 2H), 4.98~4.87(m, 1H), 3.97(s, 3H), 3.91(s, 3H), 3.76(s, 3H). 2.66~2.53(m, 1H), 2.45(s, 3H), |
| Compound 55 | $^1$H NMR (300 MHz, CDCl$_3$): δ 8.52(d, J=6.95Hz, 1H), 7.97(d, J=8.43Hz, 1H), 7.71(s, 1H), 7.64(s, 1H), 7.51(d, J=8.25 1H), 7.33(d, J=10.44, 1H), 7.04(d, J=10.44, 1H), 6.56(s, 1H), 5.45(s, 2H), 5.03~4.92(m, 1H), 3.96(s, 3H) 3.93(s, 3H), 3.73(s, 3H), 2.54~2.30(m, 2H), 2.37(s, 3H), 2.05~1.93(m, 2H) |
| Compound 56 | $^1$H NMR (300 MHz, CDCl$_3$): δ 8.12(d, J=7.68Hz, 1H), 7.87~7.84(m, 1H), 7.59~7.54(m, 3H), 7.33(d, J=10.41Hz, 1H), 7.07(d, J=10.41Hz, 1H), 6.56(s, 1H), 5.58~5.46(AB quartet, 2H), 4.95~4.85(m, 1H), 3.96(s, 3H), 3.93(s, 3H), 3.69(s, 3H), 2.57~2.41(m, 2H), 2.41(s, 3H), 2.05~1.94(m, |

TABLE 1-continued (Compound 45–Compound 84)

| Compound | $^1$H NMR (300 MHz): δ |
|---|---|
| Compound 57 | $^1$H NMR (300 MHz, CDCl$_3$): δ 8.52(br s, 1H), 7.91(br s, 1H) 7.71~7.60(m, 2H), 7.27(d, J=10.26Hz, 2H), 7.03(d, J=10.44Hz, 1H), 6.59(s, 1H), 5.54(s, 2H), 5.40~5.20(m, 1H), 3.97(s, 3H), 3.92(s, 3H), 3.71(s, 3H), 2.74~2.53(m, 2H), 2.41(s, 3H), 2.30~2.10(m, 2H) |
| Compound 58 | $^1$H NMR (300 MHz, CDCl$_3$): δ 9.23(d, 1H), 8.03(s, 1H), 7.85(d, J=8.07Hz, 1H), 7.70(s, 1H), 7.51(d, J=8.04Hz, 1H), 7.45(d, J=10.44Hz, 1H), 2.21(d, J=10.80, 1H), 6.57(S, 1H), 5.48~5.25(AB quartet, 2H), 4.97–4.88(m, 1H), 3.98(s, 3H), 3.92(s, 3H), 3.76(s, 3H). 2.63~2.55(m, 1H), 2.47(s, 3H), 2.48~2.24(m, 3H) |
| Compound 59 | $^1$H NMR (300 MHz, CDCl$_3$): δ 7.79(d, J=1.65Hz, 1H), 7.56~7.39(m, 7H), 7.25(d, J=9.15Hz, 1H), 7.01(d, J=10.44Hz, 1H), 6.84(s, 1H), 6.49(s, 1H), 5.52(d, J=6.96Hz, 1H), 5.45(s, 2H), 4.53(m, 1H), 3.96(s, 3H), 3.88(s, 3H), 3.70(s, 3H), 2.43(s, 3H), 2.41~2.15(m, 2H), 1.55~1.30(m, 1H), 1.20~1.05(m, 1H) |
| Compound 60 | $^1$H NMR (300 MHz, CDCl$_3$): δ 8.47(d, J=6.6Hz, 1H), 7.91(d, J=1.86Hz, 1H), 7.73~7.70(m, 2H), 7.44~7.35(m, 5H), 7.25(d, J=8.79Hz, 1H), 7.16(d, J=3.09Hz, 1H), 7.13(s, 1H), 6.59(s, 1H), 5.17~5.01(AB quartet, 2H), 4.97(m, 1H), 3.98(s, 3H), 3.93(s, 3H), 3.75(s, 3H), 2.70~2.52(m, 1H), 2.45(s, 3H), 2.50~2.25(m, 3H) |

TABLE 1-continued (Compound 45–Compound 84)

| Compound | $^1$H NMR (300 MHz): δ |
|---|---|
| Compound 61 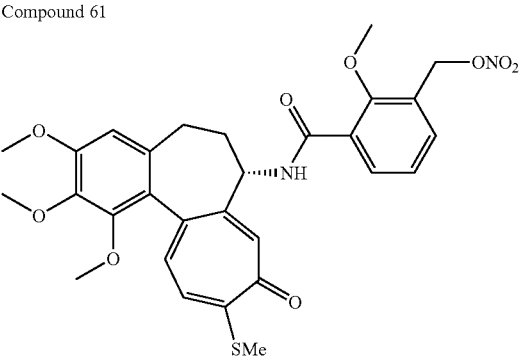 | $^1$H NMR (300 MHz, CDCl$_3$): δ 7.92–7.89(m, 2H), 7.55(d, J=7.50Hz, 1H), 7.33–7.21(m, 3H), 7.06(d, J=10.44Hz, 1H), 6.57(S, 1H), 5.64–5.49(AB quartet, 2H), 4.91~4.87(m, 1H), 3.96(s, 3H), 3.93(s, 3H), 3.92(s, 3H), 3.87(s, 3H), 2.59~2.35(m, 3H), 2.43(s, 3H), 2.04–1.91(m, 1H) |
| Compound 62 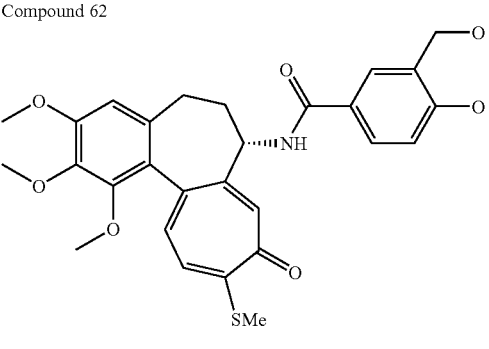 | $^1$H NMR (300 MHz, CDCl$_3$): δ 7.91(d, J=7.14Hz, 1H), 7.85~7.79(m, 2H), 7.55(s, 1H), 7.36(d, J=10.44Hz, 1H), 7.11(d, J=10.44Hz, 1H), 6.73(d, J=8.61Hz, 1H), 6.56(s, 1H), 5.43~5.23(AB quartet, 2H), 4.94~4.88(m, 1H), 3.96(s, 3H), 3.91(s, 3H), 3.82(s, 3H), 3.75(s, 3H), 2.59~2.33(m, 2H), 2.42(s, 3H), 2.17~2.05(m, 2H) |
| Compound 63 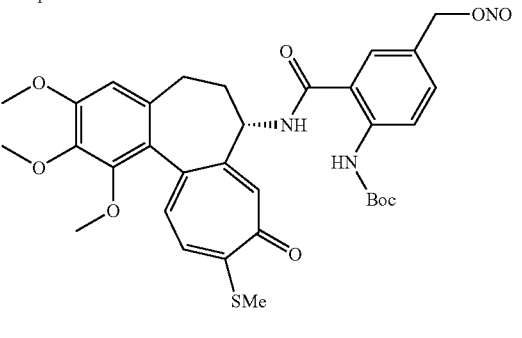 | $^1$H NMR (300 MHz, CDCl$_3$): δ 9.98(s, 1H), 8.26(d, J=8.61Hz, 1H), 7.96(d, J=8.61Hz, 1H), 7.85(s, 1H), 7.57(s, 1H), 7.33(d, J=10.62Hz, 1H), 7.08(d, J=10.62Hz, 1H), 6.56(s, 1H), 4.87(m, 1H), 4.34(AB quartet, 2H), 3.97(s, 3H), 3.91(s, 3H), 3.74(s, 3H), 2.60~2.25(m, 3H), 2.39(s, 1H), 2.17~2.03(m, 1H), 1.45(s, 9H) |
| Compound 64 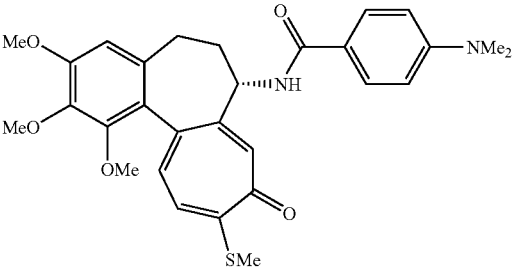 | $^1$H NMR (300 MHz, CDCl$_3$): δ 7.67(d, 2H), 7.31(m, 2H), 7.03(d, 1H), 6.59(m, 4H), 4.87(m, 1H), 3.95(s, 3H), 3.90(s, 3H), 3.73(s, 3H), 2.99 (s, 6H), 2.49(m, 3H), 2.42(s, 3H), 1.94(m, 1H) |

TABLE 1-continued (Compound 45–Compound 84)

| Compound | $^1$H NMR (300 MHz): δ |
|---|---|
| Compound 65 | $^1$H NMR (300 MHz, D$_2$O): δ 8.14(d, 1H), 7.76(d, 2H), 7.61(s, 1H), 7.36(d, 1H), 7.10(m, 3H), 6.55(s, 1H), 5.18(m, 1H), 4.18(m, 2H), 3.96 (s, 3H), 3.90(s, 3H), 3.75(s, 3H), 2.45(m, 3H), 2.42(s, 3H), 2.02(m, 1H) |
| Compound 66 | $^1$H NMR (300 MHz, CDCl$_3$): δ 8.08(d, J=7.50Hz, 1H), 7.59(s, 1H), 7.38(d, J=10.44Hz, 1H), 7.15(d, J=10.26Hz, 1H), 6.87(s, 1H), 6.56(s, 1H), 5.29(s, 2H), 4.79~4.53(m, 1H), 3.96(s, 3H), 3.95(s, 1H), 3.91(s, 3H), 3.72(s, 3H), 2.63~2.08(m, 4H), 2.46(s, 3H) |
| Compound 67 | $^1$H NMR (300 MHz, CDCl$_3$): δ 9.04(b, 1H), 8.90(d, 1H), 7.57(s, 1H), 7.33(d, 1H), 7.09(m, 2H), 6.53(s, H), 4.75(m, 1H), 4.47(dd, 2H), 3.94 (s, 3H), 3.90(s, 3H), 3.67(s, 3H), 2.49(m, 1H), 2.42(s, 3H), 2.26(m, 2H), 2.04(m, 1H), 1.76(s, 3H) |
| Compound 68 | $^1$H NMR (300 MHz, CDCl$_3$): δ 6.49(s, 1H), 5.76(m, 1H), 4.29~4.22(m, 1H), 3.90(s, 3H), 3.85(s, 3H), 3.82(s, 3H), 3.90~3.77(m, 2H), 2.88~2.85(m, 1H), 2.62~2.42(m, 3H), 2.20~2.16(m, 1H), 1.97~1.86(m, 1H), 1.13~1.03(m, 1H), 1.08(d, J=6.03Hz 3H), 0.98~0.80(m, 1H), |
| Compound 69 | $^1$H NMR (300 MHz, CDCl$_3$): δ 7.76(br s, 1H), 7.40(s, 1H), 7.39~7.21(m, 2H), 7.09(d, J=11.16Hz 1H), 6.53(s, 1H), 4.61(m, 1H), 3.94(s, 3H), 3.91 (s, 3H), 3.70(s, 3H), 2.58~1.62(m, 4H), 1.97(s, 3H) |

TABLE 1-continued (Compound 45–Compound 84)

| Compound | $^1$H NMR (300 MHz): δ |
|---|---|
| Compound 70 | $^1$H NMR (300 MHz, CDCl$_3$): δ 6.48(s, 1H), 5.56(d, J=7.32Hz, 1H), 4.21~4.11(m, 1H), 3.87(s, 3H), 3.84(s, 3H), 3.82(s, 3H), 2.68~2.14(m, 10H), 1.86~1.70(m, 4H), 1.61~1.50(m, 1H), 1.28~1.24(m, 1H), 1.07(d, 3H), 0.95~0.87(m, 1H), 0.56~0.44(m, 1H) |
| Compound 71 | $^1$H NMR (300 MHz, CDCl$_3$): δ 7.39(s, 1H), 7.31(d, 1H), 7.06(d, 1H), 6.48(s, 1H), 4.65(m, 1H), 3.94(s, 9H), 3.86(s, 3H), 2.52(s, 3H), 2.43(m, 2H), 1.83(m, 1H), 1.20(m, 3H), 1.04(d, J=5.31Hz 3H), 0.87~0.85(m 1H), 0.55(m, 1H) |
| Compound 72 | $^1$H NMR (300 MHz, CDCl$_3$): δ 7.90(m, 1H), 7.60(d, J=4.41Hz, 1H), 7.31(s, 1H), 6.33~6.22(m, 2H), 4.70(m, 1H), 3.93(s, 3H), 3.90(s, 3H), 2.91(s, 3H), 2.53~2.44(m, 2H), 2.03(m, 1H), 1.10(m, 4H), 1.08(m, 3H), 0.58(m, 1H) |
| Compound 73 | $^1$H NMR (300 MHz, CDCl$_3$): δ 8.29(s, J=9.87Hz 1H), 7.46(d, J=9.87Hz 1H), 7.37(d, J=4.59Hz 1H), 7.36(s, 1H), 6.34(s, 1H), 4.60(m, 1H), 3.89(s, 6H), 3.36(s, 3H), 2.53~2.44(m, 2H), 1.10(m, 4H), 1.08(m, 4H), 0.57(m, 1H) |
| Compound 74 | $^1$H NMR (300 MHz, CDCl$_3$): δ 7.45(d, J=10.44Hz, 1H), 7.15(d, 2H), 6.84~6.72(m, 1H), 6.37(s, 1H), 596(dd, 1H), 4.72~4.66(m, 1H), 3.92 (s, 3H), 3.90(s, 3H), 2.54~2.19(m, 3H), 2.45(s, 3H), 1.94~1.83(m, 1H), 1.84(d, 3H) |

TABLE 1-continued (Compound 45–Compound 84)

| Compound | $^1$H NMR (300 MHz): δ |
|---|---|
| Compound 75 | $^1$H NMR (300 MHz, CDCl$_3$): δ 7.86(m, 1H), 7.61(d, 1H), 7.27(s, 1H), 6.84~6.77(m, 1H), 6.40(s, 1H), 5.88(d, 1H), 4.73(m, 1H), 3.95(s, 3H), 3.90(s, 3H), 2.89(s, 3H), 2.53~2.45(m, 2H), 2.28(m, 1H), 1.83(d, 3H), 1.84~1.82(m, 1H) |
| Compound 76 | $^1$H NMR (300 MHz, CDCl$_3$): δ 8.30(d, J=9.87Hz, 1H), 7.53(d, J=9.87Hz, 1H), 7.30(s, 1H), 6.84~6.77(m, 1H), 6.36(s, 1H), 5.94(dd, 1H), 4.67~4.61(m, 1H), 3.91(s, 6H), 3.45(s, 3H), 2.55~2.53(m, 1H), 2.42~2.40(m, 1H), 2.23~2.19(m, 1H), 1.87~1.84(m, 1H), 1.86(d, 3H) |
| Compound 77 | $^1$H NMR (300 MHz, CDCl$_3$): δ 7.28(m, 2H), 7.04(d, 1H), 6.80~6.72(m, 2H), 6.53(s, 1H), 6.14(d, 1H), 4.77~4.69(m, 1H), 4.04~4.01(m, 2H), 3.95(s, 3H), 3.91(s, 3H), 3.66(s, 3H), 3.34(s, 3H), 2.58~2.43(m, 2H), 2.43(s, 3H), 2.38~2.23(m, 1H), 1.92~1.86(m, 1H) |
| Compound 78 | $^1$H NMR (300 MHz, CDCl$_3$): δ 7.38~7.28(m, 2H), 7.07(d, J=10.44Hz, 1H), 6.82~6.70(m, 1H), 6.52(s, 1H), 5.92(d, 1H), 5.73(s, 1H), 4.72(m, 1H), 3.93(s, 3H), 3.66(s, 3H), 2.30~2.23(m, 3H), 1.91~1.83(m, 1H), 1.77(d, J=8.25Hz, 3H) |

TABLE 1-continued (Compound 45–Compound 84)

| Compound | ¹H NMR (300 MHz): δ |
|---|---|
| Compound 79 | ¹H NMR (300 MHz, CDCl₃): δ 7.89(d, J=9.72Hz, 1H), 7.53(d, J=9.72Hz, 1H), 7.31(s, 1H), 6.84~6.77(m, 1H), 6.66(d, J=6.57Hz, 1H), 6.53(s, 1H), 5.83(s, 1H), 4.70(m, 1H), 3.94(s, 3H), 3.66(s, 3H), 2.89(s, 3H), 2.61~2.195(m, 4H), 1.82(d, 3H) |
| Compound 80 | ¹H NMR (300 MHz, CDCl₃): δ 7.29(d, J=10.26Hz, 1H), 7.21(s, 1H), 7.04(d, J=10.26Hz, 1H), 6.54(s, 1H), 6.44(d, J=7.32Hz, 1H), 5.71(s, 1H), 5.32(s, 1H), 4.69(m, 1H), 3.94(s, 3H), 3.90(s, 3H), 3.68(s, 3H), 2.61–2.23(m, 5H), 2.43(s, 3H), 1.91–1.82(m, 1H), 1.05(t, 3H) |
| Compound 81 | ¹H NMR (300 MHz, CDCl₃): δ 7.87(d, J=9.72Hz, 1H), 7.49(d, J=9.68Hz, 1H), 6.81(m, 1H), 6.54(s, 1H), 6.33(d, J=6.57Hz, 1H), 5.87(m, 1H), 4.67(m, 1H), 3.94(s, 3H), 3.91(s, 3H), 3.72(s, 3H), 2.91(s, 3H), 2.66–2.21(m, 3H), 1.89–1.77(m, H), 1.84(s, J=6.78Hz, 2H), 1.26(s, 2H), 0.95(t, 3H) |
| Compound 82 | ¹H NMR (300 MHz, CDCl₃): δ 7.28(d, J=10.44Hz, 1H), 7.18(s, 1H), 7.05(d, J=10.44Hz, 1H), 6.54(s, 1H), 6.44–6.28(m, 2H), 5.66(s, 1H), 5.48(s, 1H), 5.40(dd, 1H), 4.72(m, 1H), 3.95(s, 3H), 3.91(s, 3H), 3.68(s, 3H), 2.60–2.25(m, 3H). 2.43(s, 3H), 1.86(m, 1H) |

TABLE 1-continued (Compound 45–Compound 84)

| Compound | $^1$H NMR (300 MHz): δ |
|---|---|
| Compound 83 [structure] | $^1$H NMR (300 MHz, CDCl$_3$): δ 7.33(s, 1H), 7.28(d, 1H), 7.12(d, J=10.62Hz, 1H), 7.07(d, J=10.62, 1H), 6.94(d, J=6.96Hz, 1H), 6.53(s, 1H), 6.16~5.94(m, 2H), 5.85(d, J=15.00Hz, 1H), 4.74(m, 1H), 3.94(s, 3H), 3.90(s, 3H), 3.69(s, 3H), 2.60~2.25(m, 3H). 2.43(s, 3H), 1.79(m, 1H), 1.78(d, J=6.21Hz, 3H) |
| Compound 84 [structure] | $^1$H NMR (300 MHz, CDCl$_3$): δ 7.30(d, J=10.26Hz, 1H), 7.21(s, 1H), 7.04(d, J=10.26Hz, 1H), 6.58(s, 1H), 6.54(s, 1H), 6.29(d, J=7.14Hz, 1H), 5.10(s, 1H), 4.97(s, 1H), 4.70(m, 1H), 3.94(s, 3H), 3.90(s, 3H), 3.69(s, 3H), 2.61–2.23(m, 5H), 2.43(s, 3H), 1.91–1.82(m, 1H), 1.88(s, 3H), 1.03(t, 3H) |

Example A

Mixed Lymphocyte Reaction (MLR) Tests

MLR tests were carried out to determine the immunosuppressive effect of an immunosuppressive candidate material. When a responding cell (BALB/c mouse spleen cell) and a stimulating cell (DBA 57b1/6 mouse spleen cell) were cultured separately, the cells hardly grew. On the contrary, when the cells were simultaneously cultured, an antigen-antibody reaction was induced and the cells were proliferated. The proliferated cells were treated with the immunosuppressive candidate material for measurement of degree of inhibition of cell proliferation.

Responding cells (BALB/c mouse spleen cells) and stimulating cells (DBA/2 mouse spleen cells) were respectively seeded into each well of 96-well plates at a concentration of 2×10$^5$ cells/well for simultaneous culturing, and were treated with cyclosporin A (positive control group), colchicines, and colchicine derivatives of the present invention (compounds 6, 9, 10, 11 and 12). After culturing for 72 hours at a CO$_2$ incubator, a 20 μl MTS solution was added to each well, followed by further culturing for 2 to 4 hours and measuring OD at 490 nm by using ELISA. In addition, the cells were labeled with radioisotope. That is, one-way MLR was conducted to observe the degree of proliferation of responding cells. A lymphocyte of a recipient mouse was used as a responding cell and a donor mouse spleen was used as a stimulating cell, and division of the stimulating cell was suppressed through irradiation to check the degree of proliferation of the responding cell. As for nontreated group (control group), CsA and colchicine derivatives were added to suppress the proliferation of the responding cell at concentrations of 0, 0.5, 5, 50, 500 and 5000 ng/ml, respectively, and cultured for 3, 4, 5 and 7 days. As for the responding cell, lymph-node of the recipient mouse (C57BL/6, H-2$^b$) was separated and placed in the RPMI-1640 culture medium containing 10% FBS (fetal bovine serum). The lymphocyte was homogenized and passed through a mesh (pore size; <20M) to obtain a single lymphocyte cell. As for the stimulating cell, on the other hand, a spleen of the donor mouse (BALB/c, H-2$^d$) was avulsed and placed in the DMEM culture medium containing 10% FBS. The spleen tissue was homogenized and made to a single cell using the same method used for the responding cell. The cells in each culture medium were first centrifuged for 5 minutes at 1450 rpm and then centrifuged again, up to three times, for five minutes by using 1×PBS containing 2 mM EDTA and were washed. The culture media of these two cells were prepared by adding 10% FBS, 5×10$^{-5}$M beta-mercaptoethanol 1% HEPES and 1% antibiotics to RPMI-1640. After the last washing, 1×PBS was removed and the cells were floated in the culture media. The number of responding cells and the number of stimulating cells were set to 2×10$^6$/ml and 5×10$^6$/ml, respectively. 100 μl was taken from each suspension of the responding cell and the stimulating cell, and mixed together in each well of 96-well plates by 3 wells per test group. Following the mixed culture activation, the wells were treated with 1 μCi of $^3$H-thymidine after 3, 4, 5 and 7 days, respectively, and cultured for 8 hours. Using the beta-counter, corn of the cells was measured and based on this the degree of proliferation of the responding cell was examined.

It can be found that the colchicine derivatives according to the present invention, that is, the test compounds suppressed growth of the cells even at concentrations as low as 100 to 1000 nM and had a good immunosuppressive effect.

Example B

Immunosuppressive Effect Test Using BALB/c Mouse Spleen Cells

This test was carried out to determine the immunosuppressive effect of an immunosuppressive candidate material by checking anti-proliferation of T cells and B cells. To identify the degree of proliferation inhibition, responding cells (BALB/c mouse spleen cells) were treated with an immunosuppressive candidate material, lipopolysaccharide (LPS) as a B cell activator and concanvalin A (ConA) as a T cell activator. It turned out that the responding cells treated with LPS induced proliferation of B cells and those treated with ConA induced proliferation of T cells.

The spleen cells were treated with colchicine derivative compounds 3, 25, 33, 39 and 84 at a concentration of 10 ng/ml and 30 ng/ml. B cell proliferation was induced to 1 μg/ml LPS and T cell proliferation was induced to 1 μg/ml of ConA. After culturing for 54 hours, 1 μCi/ml of [3H]-thymidine was added to each well, followed by further culturing for 18 hours, and then the cultivated cells were collected. FIG. 1 shows a graph showing the anti-proliferious and immunosuppressive effects of T-cell and B-cell in this test on colchicine derivatives (compounds 3, 25, 33, 39 and 84). The results are expressed in terms of relative cell growth with respect to vehicle control (100%, 0.1% DMSO). As can be seen in FIG. 1, the colchicine derivatives according to the present invention suppressed proliferation of the B and T cells induced by LPS and ConA, respectively, in a concentration-dependent manner. In particular, they exhibited a remarkable anti-proliferative effect on B cells.

Example C

Effect of Macrophage on NO Generation

Figure 2:
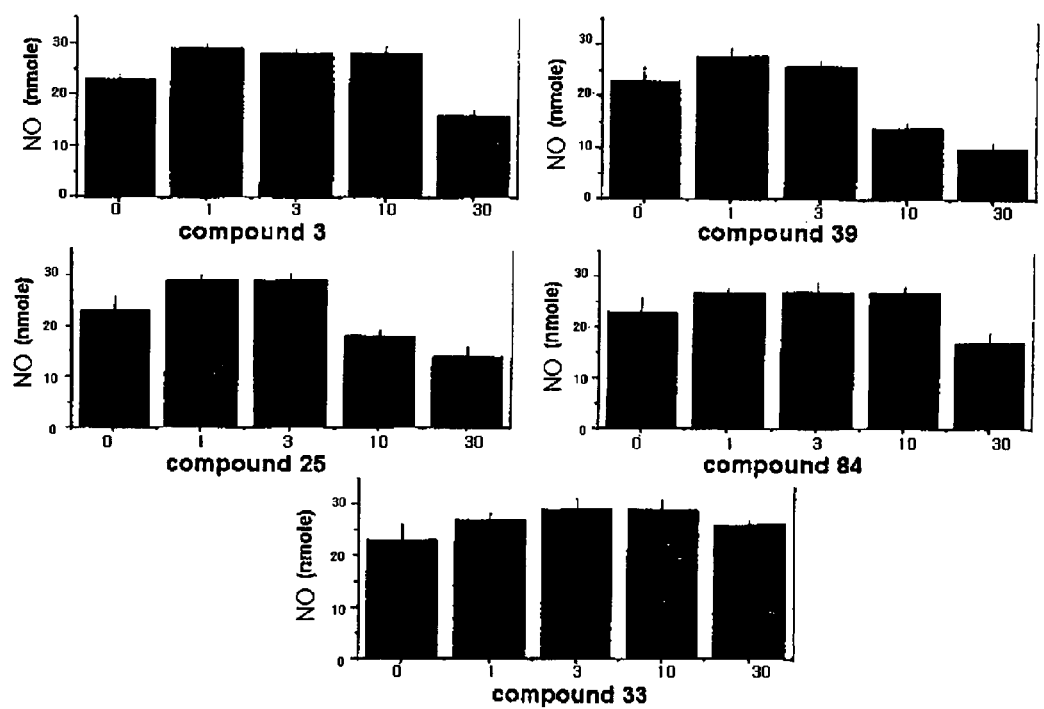
FIG. 2 shows an inhibitory effect on NO generations after treating a macrophage cell line, RAW264.7 with colchicine derivatives according to the present invention (compounds 3, 25, 33, 39 and 84) to confirm the immunosuppressive effect of the colchicine derivatives.

A macrophage cell line RAW264.7 was treated with colchicine derivative compounds 3, 25, 33, 39 and 84 at a contraction of 1-30 ng/ml. NO generation was induced to 1 μg/ml LPS. After culturing for 24 hours, NO generation was measured with Griess reagent. As can be seen in FIG. 2, the compounds 25 and 39 exhibited a superior inhibitory effect on NO generation.

Example D

Cytokine Profile Investigation

Figure 3A:
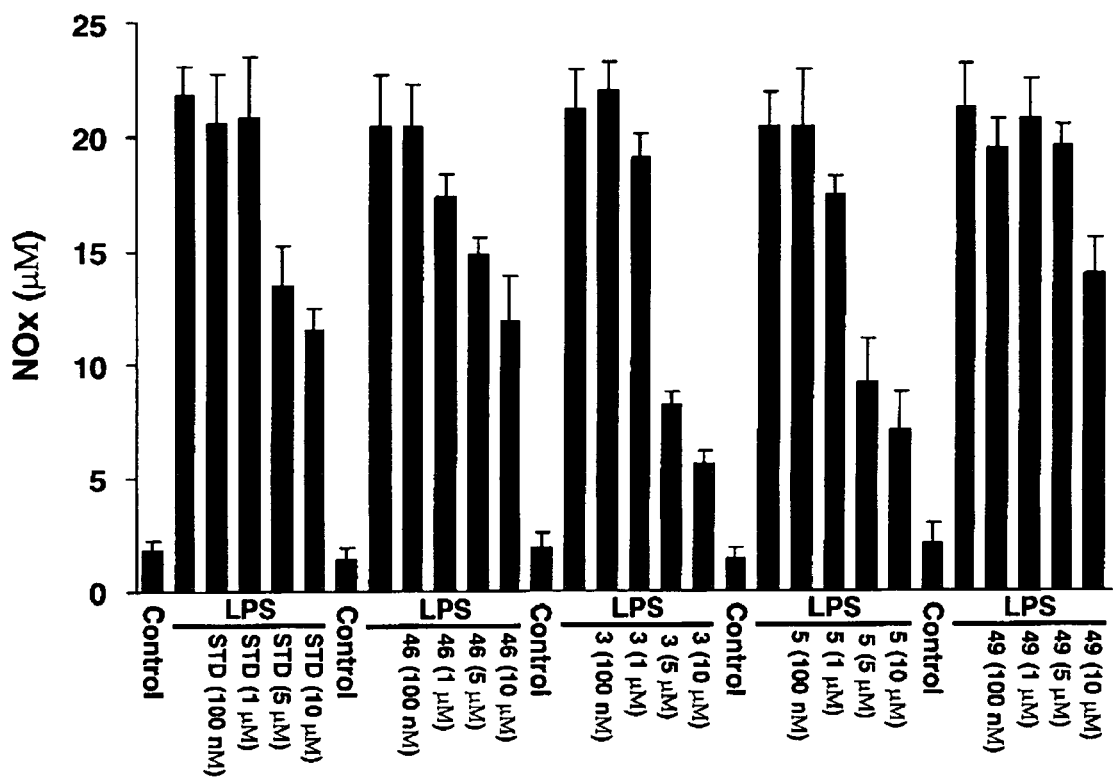
FIG. 3A shows an inhibitory effect of NO generation in LPS-stimulated cells induced by the colchicine derivatives (standard compound, compounds 3, 5, 46, and 49)
Figure 3B:
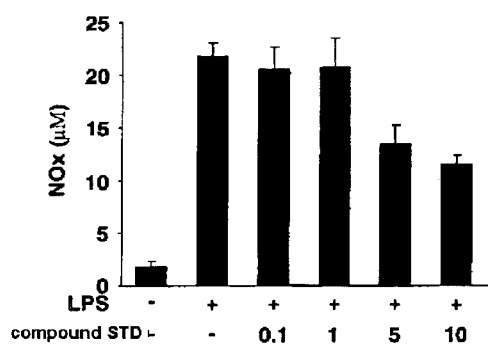
FIG. 3B shows an inhibitory effect of NO generation in LPS-stimulated cells induced by the colchicine derivatives (standard compound, and compound 3)
Figure 3B:
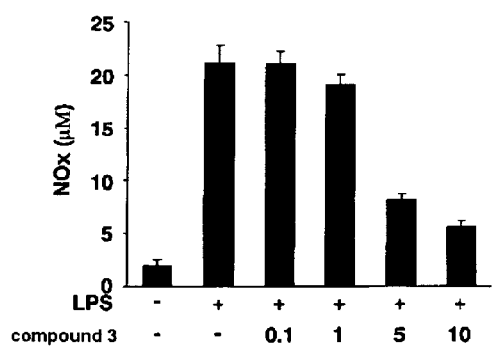
Figure 3C:
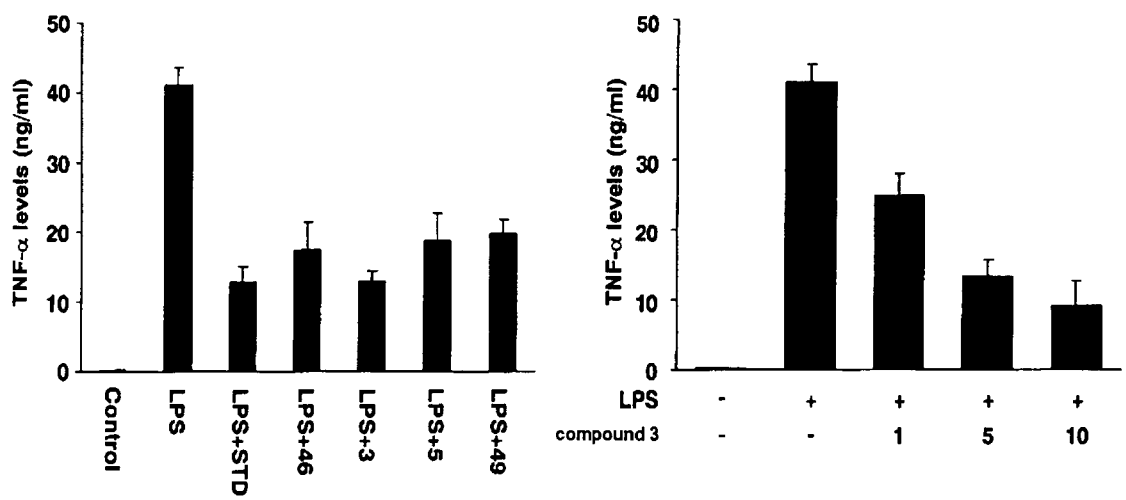
FIGS. 3C and 3D show an inhibitory effect of TNF-α production and IL-β production in LPS-stimulated cells induced by compound 3, respectively.
Figure 3D:
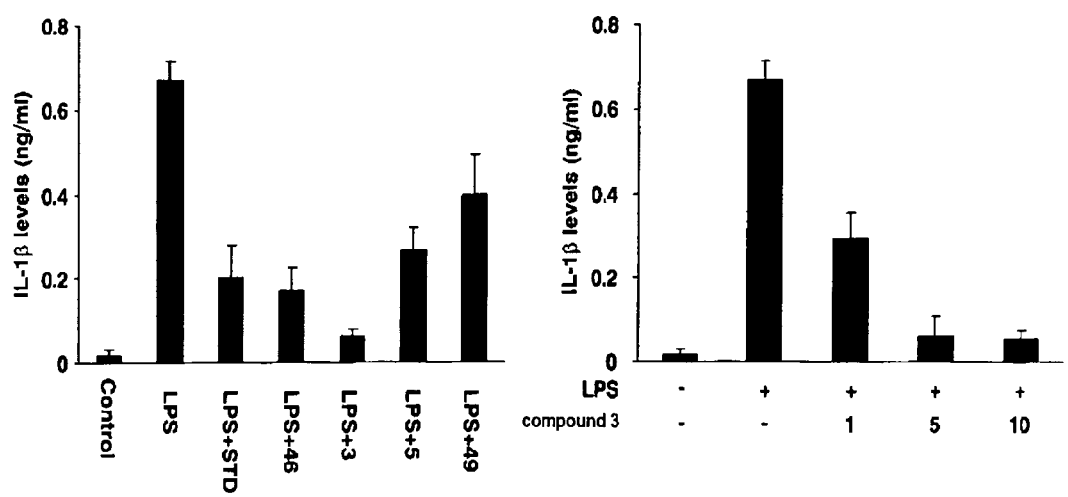

The degree of cytokine expression was investigated for a test group selected after the mixed lymphocyte reaction. A macrophage was cultured for 3 days in a culture medium containing CsA and each of colchicine derivative compounds 1, 3, 5, 46 and 49, respectively, at a concentration of 0.1-10 μM. To this culture medium was added 100 μl of Griess reagent (0.1% naphthylethyenediamine dihydrochloride in $H_2O$: 1% sulfanilamide in 5% $H_3PO_4$=1:1). About 5 minutes later, the change in color was measured based on absorbance change that was observed by a microplate reader at 550 nm. The concentration of nitrite was determined from a standard curve that was obtained using $NaNO_2$ standard solutions at a concentration between 0 and 128 μM. In addition, the concentration of PGE2 was measured with enzyme immunoassay, and measurement of TNF-α and IL-1β were achieved through sandwich ELISA. FIG. 3 shows the test results: FIGS. 3A and 3B show an effect of the test compounds on NO production in LPS-stimulated cells, FIG. 3C shows an effect of the test compounds on TNF-α production in LPS-stimulated cells, and FIG. 3D shows an effect of the test compounds on IL-β production in LPS-stimulated cells. In FIG. 3, the compound defined as 'STD' is a colchicines derivative, 3-nitrooxymethyl-N-(1,2,3-trimethoxy-10-methylsulfonyl-9-oxo-5,6,7,9-tetrahydro-benzo[α]heptarene-7-yl)-benzamide, described in Example 12 of U.S. patent application Ser. No. 10/479,057. As can be seen in FIG. 3, the colchicine derivative compound 3 exhibited a superior inhibitory effect on the generation of NO, TNF-α and IL-1β.

Example E

Skin Graft Test

Figure 4:
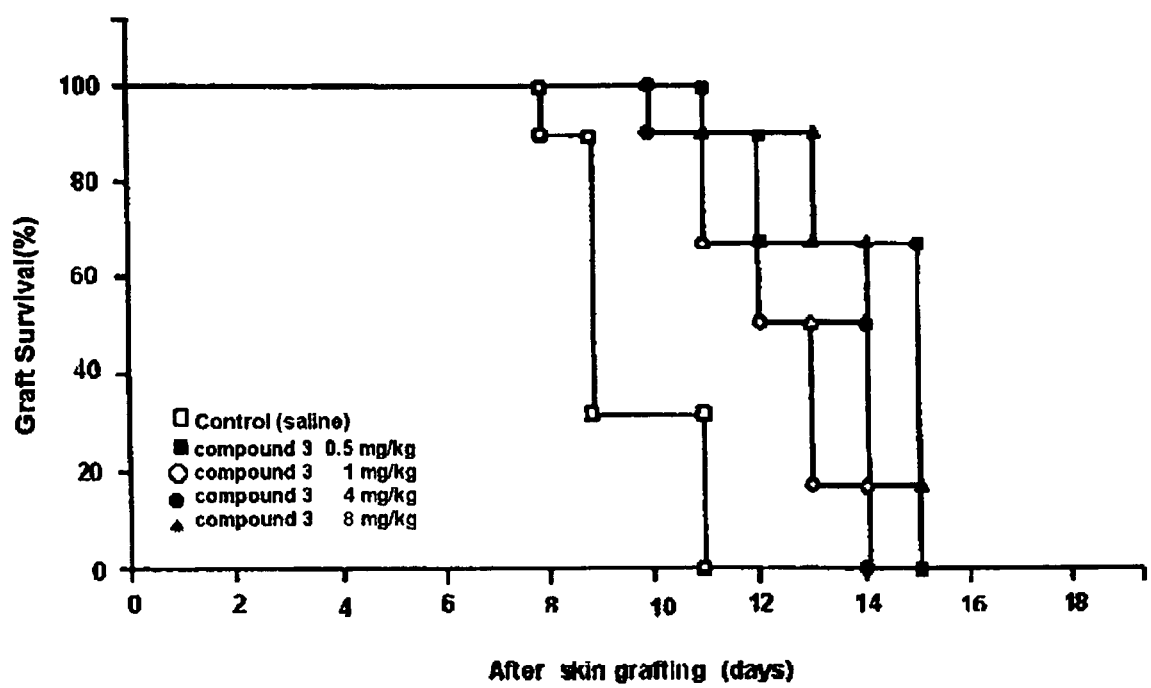
FIG. 4 shows the immunosuppressive effect of a colchicine derivative according to the present invention (compound 3) in a tail-skin grafts test where a tail tissue of a donor mouse (BALB/c, H-2d) is grafted onto the chest of a recipient mouse (C57BL/6, H-2b).

A tail tissue of the donor mouse (BALB/c, $H-2^d$) was grafted onto the chest of the recipient mouse (C57BL/6, $H-2^b$) using tail-skin grafts. The donor mouse was first weighed. A mouse weighing 10-20 g was put under anesthesia by injecting 0.2 ml of 1× avertin into the peritoneal cavity. Five minutes later, it was checked whether the mouse was sufficiently anesthetized. Next, tail grafts of the donor mouse were prepared. The tail was wiped with a piece of gauze soaked in 70% ethanol. Then, the tail was cut out of the body using a scalpel. A cutting (dissection) line was drawn over the back side of the tail and the tail skin was avulsed with forceps. Inner side of the tail lied face down on a Petri-dish on which a sterilized 1×PBS filter paper was placed, and the Petri-dish was shut up to keep moisture in the tail skin. The tail skin was completely spread in every direction using forceps, and fixed. The skin was then cut in dimension of 0.75 cm×0.75 cm using a scalpel. The recipient mouse (C57BL/6, $H-2^b$) was also weighed. When the mouse was put under anesthesia, its chest was shaved using an electric razor. The upper portion of the chest, a stable and firm position where the mouse can move freely, was set as the graft bed for skin graft. The left thorax of the recipient mouse (C57BL/6, $H-2^b$) was wiped with a piece of gauze soaked in 70% ethanol and was dried. The skin was then cut out in a square shape. The skin should be cut as thin as possible not to cut the panniculus camosus layer. Preferably, the skin in the central portion was avulsed using forceps. Next, the skin graft taken from the donor mouse was placed on the graft bed. At this time, it is important to check whether the edge of the graft was rolled up or whether it was overlapped with normal surrounding skin. The graft should be smaller than the graft bed, and there should be a margin between the surrounding host skin and the graft skin. In this manner, although the graft shifts slightly, it may still be in the graft bed. The skin graft should be done in a manner that hair on the graft grows in opposite direction of the host hair. The entire graft and the normal surrounding tissue were covered with a piece of double-thickness Vaseline gauze, and the wrinkles of the gauze were smoothed out to be adhered flat. The graft was wrapped in a surgical band, being careful not to interfere with breathing of the mouse. After the surgery, the mouse was exposed to a lamp to keep the body warm. In the following minutes, the mouse was checked whether the surgical band was not wrapped too tight. 7 days after the skin graft, the mouse was anesthetized again and the surgical band was removed. The skin graft was done in accordance with the above-described procedure. The test group was divided into two: a control group was treated with 0.2 ml of saline, while a test group consisting of 6 individuals was treated with the colchicine derivative compound 3 at concentrations of 0, 0.5, 1, 4, and 8 mg/kg, respectively, each being administered to the peritoneal cavity of 6 individuals, every other day from the surgery. After the surgical band was removed, the survival rate of the grafted skin was checked. If less than 20% of the grafted skin is left, it was determined that the skin graft was rejected. Even though engraftment extension in a concentration-dependent manner was not shown, the grafted tissue survived an average of 4 days longer than the control group that was not treated with the colchicine derivative compound 3 (FIG. 4, Table 2). FIG. 4 is a graph showing the immunosuppressive effect of a colchicine derivative according to the present invention in a tail-skin grafts test where a tail tissue of a donor mouse (BALB/c, H-$2^d$) is grafted onto the chest of a recipient mouse (C57BL/6, H-$2^b$) (Compound 3). Considering that a medicine is reported to be effective if 2 days are extended, the above-described result is indeed remarkable.

TABLE 2

Effect of compound 3 on the survival of allogeneic skin graft

| Group | Number of animals | Dose (mg/kg/body weight) | Mean survival time (day ± SD) | P value vs group 1 |
|---|---|---|---|---|
| Group 1 | 6 | 0 | 8.33 ± 1.03 | |
| Group 1 | 6 | 0.5 | 12.8 ± 1.83 | p < 0.0005 |
| Group 2 | 6 | 1 | 11.3 ± 1.21 | p < 0.005 |
| Group 3 | 6 | 4 | 11.7 ± 1.63 | p < 0.0005 |
| Group 4 | 6 | 8 | 12.5 ± 1.38 | p < 0.0005 |

* 0 to 8 mg/Kg of Compound 3 (0.2 ml) was injected intraperitoneally every other day until rejection Example F Rheumatoid Arthritis Remedy Test 1. Macrophage Cell Separation and Cell Culture Murine macrophage cell line RAW264.7 (kept in the laboratory) and primary macrophage cell were used. Macrophage was taken from the peritoneum of a mouse treated with thioglycolate broth. 1.5 ml of 4% thioglycolate broth was injected into the peritoneal cavity of a mouse (6-8 weeks, BALB/c mice), and 7 days later all of the peritoneal fluid was collected using a syringe under an aseptic condition. The peritoneal fluid was washed three times with DMEM badge. The washed cells were cultured in the DMEM badge containing 10% fetal bovine serum. Also, ROS 17/2.8, rat osteoblast sarcoma cell line, was cultured in a badge containing 10% fetal bovine serum. To find out anti-inflammatory effect of the colchicine derivative compound 3, western blot analysis was carried out using macrophage and osteoblast stimulated by cytokines.

2. Measurement of Nitrite and Diverse Cytokines Generation

100 µl of Griess reagent (0.1% naphthylethyenediamine dihydro chloride in $H_2O$:1% sulfanilamide in 5% $H_3PO_4$=1: 1) was carefully added to the macrophage cell culture medium and the osteoblast culture medium. About 5 minutes later, the change in color was measured based on absorbance change that was observed by a microplate reader at 550 nm. The concentration of nitrite was determined from a standard curve that was obtained using $NaNO_2$ standard solutions at a concentration between 0 and 128 µM. In addition, the concentration of PGE2 was measured with enzyme immunoassay, and measurement of TNF-α and IL-1β were achieved through sandwich ELISA.

3. Nitrite and Nitrate Measurement

Nitrite+Nitrate ($NO_2^-$+$NO_3^-$) were measured by using a mouse serum sample. The tail was cut to get blood. The blood thusly obtained was centrifuged and plasma was obtained therefrom. 100 µl of plasma, 200 µl of 0.5N NaOH and 200 µl of 10% $ZnSO_4$ were mixed and de-proteination was carried out. Measurement was taken from the upper layer fluid only. For measurement of $NO_2^-$ and $NO_3^-$, $NO_3^-$ was converted into $NO_2^-$ by nitrate reductase, and absorbance change was observed at 550 nm.

4. Western Blot Analysis

Cells were suspended in 20 mM Tris-HCl buffer (0.1 mM Phenylmethysulfonyl fluoride (PMSF), 5 µg/ml apotinin, 5 µg/ml Pepstain A, 1 µg/ml Chymostatin), and homogenized by three times of freezing-thawing cycles. 13,000 g of the suspension was centrifuged at 4° C. for 20 minutes, and cytoplasmic solution was obtained from the upper layer fluid. The cytoplasmic solution went through electrophoresis in 8% SDS-PAGE, and protein was transferred to a nitrocellulose membrane. The membrane was washed with PBS-Tween containing 5% milk, and hybridized with horseradish peroxidase-conjugated antimouse IgG for one hour at room temperature. The membrane was then washed with PBS-Tween four times, reacted with chemiluminescence reagent (ECL), and exposed to light to visualize protein band of a specific gene.

5. Real-Time Polymerase Chain Reaction Test mRNA of a group treated with LPS and the colchicine derivative compound 3 was obtained from macrophage, and measurement was carried out thereon using gene-specific fluorescent-labeled probes, TaqMan Universal PCR Mix and a 7700 Sequence Detector (Applied Biosystems, Foster, Calif.). Fluorescent reporters were used for N-end by attaching FAM thereto, and assay on demand was used for C-end with no attachment. To find out the efficiency of RNA compensation and reverse transcription, it was quantized and averaged to one of housekeeping genes, glyceraldehyde-3-phosphate dehydrogenase mRNA. As for PCR amplication, the primer and probe were designed by using computer programs, Primer Express Primers and TaqMan probes, provided by Applied Biosystems, Co. PCR was first conducted for 10 minutes at 95° C., 30 seconds at 94° C. and 1 minutes at 60° C., 45 cycles in total. Using the TaqMan probe, Pearson correlation coefficient, r, used was greater than 0.99 (r>0.99) and all samples existed within the standard curve.

6. Reverse Transcription Polymerase Chain Reaction Test

The same method as above was used to obtain mRNA, and cDNA was prepared with 31 g of mRNA. For PCR, 50 mM KCl, 10 mM Tris-HCl (pH 8.3), 1.5 mM $MgCl_2$, 0.2 mM dNTPs, 2.5 unit Taq polymerase, 0.1 µM of iNOS, COX-2, TNF-α, and IL-β were used. According to amplication conditions for all genes, the first cycle was done for 5 minutes at 94° C., the second cycle for 30 seconds at 94° C., 35 seconds at 52° C., and 45 seconds at 72° C., 32 cycles in total, and this was checked in 1.5% agarose gel. Base sequence of each primer is as follows. PCR base sequence of iNOS 5'-TTTG-GAGCAGAAGTGCAAAGTCTC-3' (forward) (SEQ ID No.1) and 5'-GATCAGGAGGGATTTCAAAGACCT-3' (reverse) (SEQ ID No.2), PCR base sequence of COX-25'-CCGTGGTGAATGTATGAGCA-3' (forward) (SEQ ID No.3) and 5'-CCTCGCTTCTGATCTGTCTT-3' (reverse) (SEQ ID No.4), PCR base sequence of TNF-α 5'-ATGAG-CACAGAAAGCATG-3' (forward) (SEQ ID No.5) and 5'-TCACAGAGCAATGACTCC-3' (reverse) (SEQ ID No.6), PCR base sequence of IL-1β 5'-ATGGCAACTGTTC-CTGAAC-3' (forward) (SEQ ID No.7) and 5'-TTAGGAA-GACACGGATTC-3' (reverse) (SEQ ID No.8), and PCR base sequence of β-actin 5'-TCCTTCGTTGCCGGTCCACA-3' (forward) (SEQ ID No.9) and 5'-CGTCTCCGGAGTCCAT-CACA-3' (reverse) (SEQ ID No. 10).

7. Immunoprecipitation and Kinase Assay

Cells of a group treated with LPS or compound 3 were washed with buffer and homogenized by immunoprecipitation buffer (50 mM Tris-HCl, pH 7.6, 150 mM NaCl, 10% glycerol, 1% Nonidet P-40, 5 mM EDTA, 1 mM DTT, 100 mM NaF, 2 mM sodium pyrophosphate, 2 mM sodium orthovanadate, 1 mM PMSF, 10 μg aprotinin per milliliter) to obtain an upper layer fluid. Later, immunoprecipitation was carried out using an IKK antibody, and the fluid was washed twice with kinase buffer. Then, the fluid was reacted with kinase buffer (20 mM HEPES (pH 7.4), 20 mM β-glycerophosphate, 20 mM $MgCl_2$, 2 mM DTT, 0.1 mM sodium orthovanadate) and a substrate 2 μM GST-IκBα, 0.5 μCi [γ-$^{32}$P]ATP at 30° C. for 30 minutes. 2× sample buffer was added and the mixture was boiled. When the reaction was completed, the mixture went through electrophoresis with 10% SDS-PAGE, and was measured with an X-ray film.

8. Arthritis Induction

Collagen-induced arthritis (CIA) model using DBA/1J mice was used for an animal experiment. At 4° C., bovine type II collagen (CII) was dissolved in 10 mM acetic acid overnight, and complete Freund's adjuvant (CFA) containing CII and *Mycobacterium tuberculosis* H37Ra were dissolved to 2 mg/ml by using a high speed homogenizer. 100 μl (CII 100 μg+CFA 100 μg) of the CII/CFA mixed solution was hypodermically injected into the tails of DBA/1 mice (Orient Co., 6-8 week-old male) using 26 G needle on 0 day. 20 days after the first injection, the mixed solution of CII and incomplete Freund's adjuvant was hypodermically injected to the tails of the mice. If arthritis was not progressed after 28 days from the first injection, 20 μg of LPS (Sigma, USA) was injected into the peritoneal cavities of those mice to accelerate the induction of arthritis. Two observers were assigned to evaluate the effect of the first injection on arthritis, i.e., 20$^{th}$ day to 45$^{th}$ day, and the prevention effect three times a week between 15$^{th}$ day to 45$^{th}$ day.

8.1 Incidence of Arthritis

In the CIA model, the number of mice having the arthritis occurred in their paws in a group treated with medication and a group not treated with medication were counted and expressed as a percentage.

8.2 Arthritis Index

In the CIA model, the degrees of edema and tumor (swelling) shown in the paws were observed to measure the occurrence frequency of arthritis and severity.

0 point: No edema or tumor.

1 point: Light edema and redness localized in mid foot or ankle joint 2 points: Light edema and redness localized in ankle arthritis to tarsal bones 3 points: Moderate edema and redness over metatarsal bones 4 points: Edema and redness in the entire portion from the ankle to the digit.

Arthritic index shown in each paw were summed to obtain an average value.

8.3 Incidence of Ankylosis

Ankylosis is a phenomenon in the process of arthritis. Thus, the occurrence of ankylosis was observed in treatment with the compound 3, and the incidence of ankylosis in a group treated with the compound 3 and in a group not treated were compared and expressed as a percentage.

9. Injection of Compound 3 into CIA Model

After the first injection with collagen, 1 mg/kg of the compound 3 were intraperitoneally injected from the 15$^{th}$ day to the 40$^{th}$ day.

10. Animal experiment to test anti-inflammatory effect of compound 3 Physiological salt solution and the compound 3 (1 mg/kg) were injected into peritoneum of 6-8 weeks old BALB/c mice (18-20 g) and divided into groups. One hour later, 10 mg/kg of LPS (*E. coli*, serotype 055, sigma) was injected into the peritoneal cavities per group. Blood was collected 12 hours later, and centrifuged at 12,000 rpm. Blood serums were collected and $NO_2^-$ and $NO_3^-$ therein were measured with nitrate reductase-based nitric oxide assay kit.

11. Electromobility Shift Assay

According to Staal et al. method, nuclear extracts were prepared from RAW264.7 stimulated by LPS for one hour. To describe briefly, cells were washed with cold PBS, collected with a scrapper, and separated using a centrifugal machine. The cells thusly separated were suspended in 5× Buffer A (10 mM HEPES, pH 7.9, 10 mM KCl, 1.5 mM $MgCl_2$, 0.5 mM dithiothreitol, 0.2 mM phenylmethylsulfonyl fluoride, and 0.5% Nonidet P-40). The cells were homogenized by Dounce homogenizer, and nuclei thereof were centrifuged for 15 minutes. A precipitate thereof was suspended in the same amount of Buffer B (Buffer A without Nonidet P-40). Again, the suspension was centrifuged for 15 minutes at 5,000 rpm, and nuclear extracts (protein) was gently mixed with 150 μl of Buffer C (20 mM HEPES, pH 7.9, 10 mM KCl, 1.5 mM $MgCl_2$, 10% glycerol, 0.2 mM phenylmethylsulfonyl fluoride, 0.2 mM EDTA, and 0.5 mM dithiothreitol) and 50 μl of Buffer D. One hour later, the mixture was centrifuged for 30 minutes at 13,000 rpm and an upper layer fluid was taken. Through electromobility shift assay, the upper layer fluid was end-labeled with [γ-$^{32}$P]ATP using T4 polynucleotide kinase. NF-κB-specific oligonucleotide was purified by using G-50 Sephadex column. At room temperature, nuclear extracts (10 μg of protein) incubated $^{32}$P-labeled oligonucleotide containing a buffer (containing 2 μg of poly(dl-dc), 4.2 mM HEPES, pH 7.4, 2.5% glycerol, 4.2 mM KCl, 1 mM $MgCl_2$, 0.02 mM EDTA, 2% Ficoll, and 21 mM dithiothreitol (final volume of 30 μl)) for 20 minutes at about 40,000 cpm (~0.5 ng). DNA-protein complex went through electrophoresis with 5% non-denaturing polyacrylamide gel, dried and checked by autoradiography.

12. Suppression of iNOS, TNF-α, and IL-1β mRNA Expression in Macrophage by Compound 3

Figure 5:
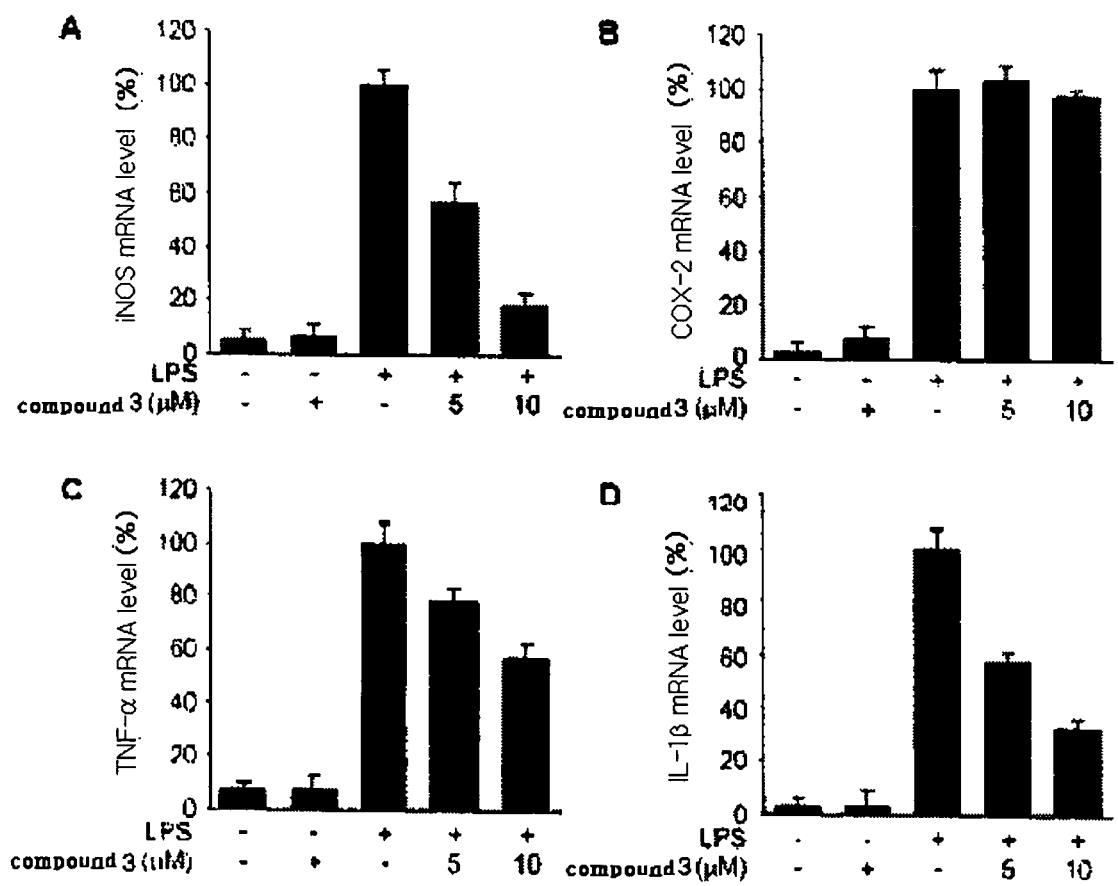
FIG. 5 shows the suppressive effect on cytokines generation of a colchicine derivative according to the present invention (compound 3) on manifestation of anti-inflammatory cytokines, iNOS (FIG. 5A), COX-2 (FIG. 5B), TNF-α (FIG. 5C), and IL-1β mRNA (FIG. 5D).

When macrophage is treated with LPS, the expressions of iNOS, COX-2, TNF-α, and IL-1β are known to be induced in the transcription process and generates NO. FIG. 5 is a graph showing the suppressive effect of a colchicine derivative according to the present invention on manifestation of anti-inflammatory cytokineiNOS, COX-2, TNF-α, and IL-1β mRNA (compound 3). In this study, when RAW264.7 cell, the macrophage cell line, was treated with 1 μg/ml of LPS, the degree of iNOS mRNA expression was 100% compared with the GAPDH, the housekeeping gene, which was measured by the real-time PCR. On the other hand, when RAW264.7 cell line was treated with the compound 3, the immunosuppressive agent, at concentrations of 5 μM and 10 μM, the degree of iNOS mRNA expression was substantially reduced by concentrations (FIG. 5A). However, when RAW264.7 cell line was treated with LPS and the compound 3, the suppression effect on COX-2 mRNA expression was not noticeable (FIG. 5B). In effect, the same result as Western blot performed previously was obtained. Additionally, the suppression effect on TNF-α and IL-1β mRNA expressions were searched by the real-time PCR under the same experiment conditions. It turned out that the degree of TNF-α and IL-1β mRNA expression was gradually reduced by concentrations of the compound 3 (FIG. 5C and FIG. 5D). This result indicates that the compound 3 suppresses the expressions of iNOS, TNF-α, and IL-1β genes in the transcription process, thereby suppressing signal transcription inducing the activation of macrophage.

13. Therapeutic Effect and Prevention Function of CIA (Collagen-Induced Arthritis) by Compound 3

Figure 6:
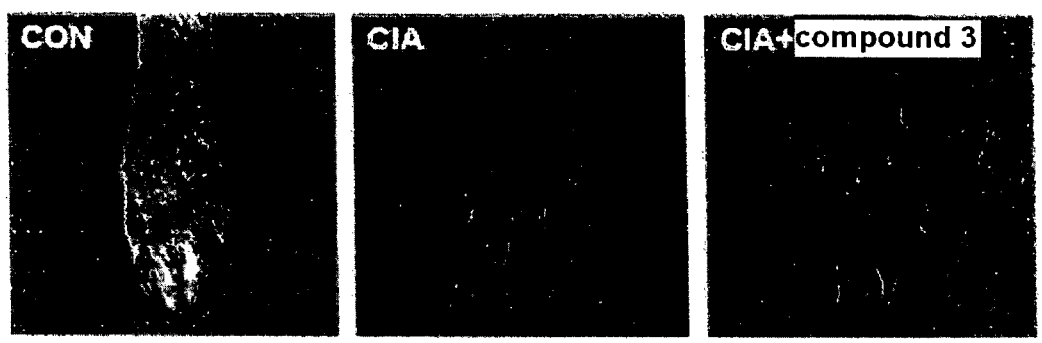
FIG. 6 shows the therapeutic and preventing effects on CIA (collagen-induced arthritis) of a colchicine derivative according to the present invention (compound 3).
Figure 6:
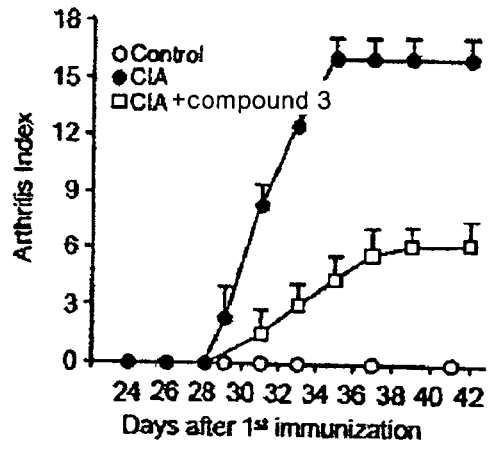
Figure 6:
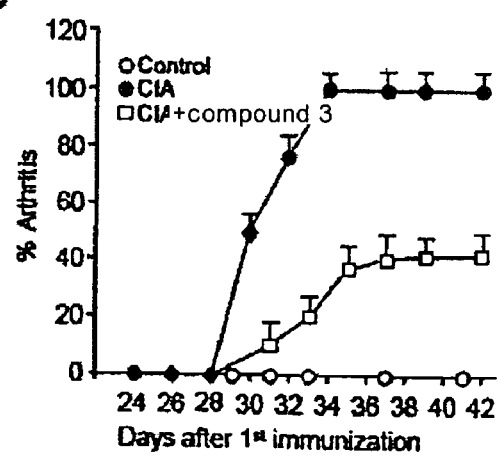
Figure 7:
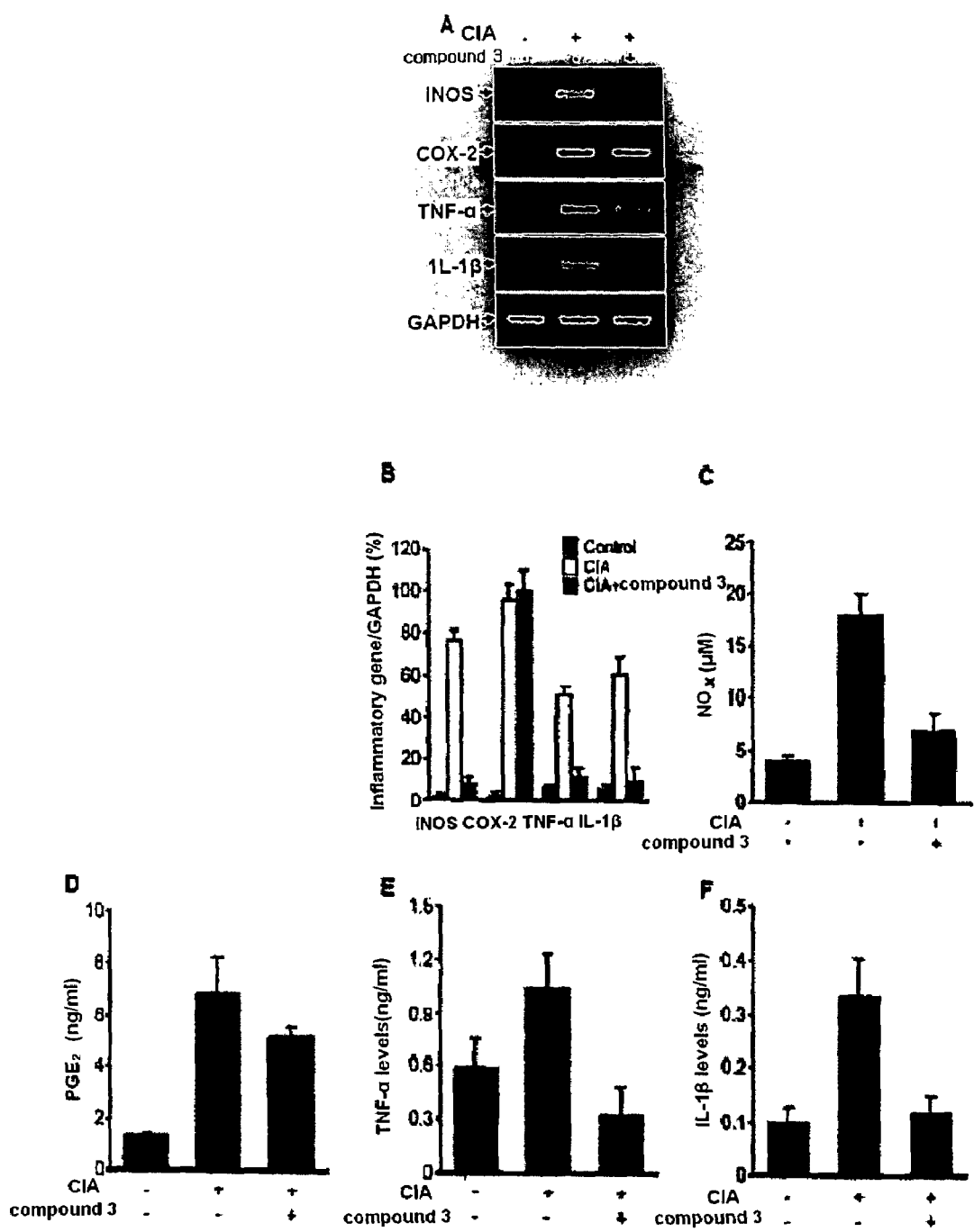
FIG. 7 shows an inhibitory effect of the mRNA expression of iNOS, COX-2, TNF-α, and IL-1β by a colchicine derivative according to the present invention (compound 3) in CIA test.

Since CIA model using DBA/1J mice is similar to Human Rheumatoid Arthritis (RA) histologically and immunologically, it is widely used as an RA test model. Therefore, the present test was carried out to determined effect of the compound 3 on CIA. A mixed solution of CII/CFA was hypodermically injected into the tails of DBA/1J mice on the $0^{th}$ day and the $21^{st}$ day. To promote arthritis induction, LPS (40 µg/mouse) was administered on the $28^{th}$ day. In result, an outbreak of arthritis was identified from the $30^{th}$ day and 100% of test models had arthritis by the $34^{th}$ day (FIG. 6A). Also, in order to study the arthritis prevention function by the compound 3 in the CIA model, after collagen injection, from the $15^{th}$ day through the $42^{nd}$ day the compound 3 (1 mg/kg) was injected into DBA/1J mice once a day, and incidence of arthritis was measured three times a week from the $16^{th}$ day through the $45^{th}$ day from the first injection. The symptom of arthritis appeared from the $30^{th}$ day after collagen injection, and 100% of the mice have arthritis by the $34^{th}$ day. The group treated with the compound 3 also had mild arthritis pain (FIG. 6B). However, the arthritis score of the edema and the tumor in the paw of the mice in the group treated with the compound 3 was about 60% lower than that of the control group injected with collagen only (FIG. 6C). When the compound 3 was administered, the incidence of ankylosis was reduced by about 70% compared to the control group. These results prove that the compound 3 can be advantageously used for preventing the collagen-induced arthritis.

14. Biochemical Inhibition Effect of Compound 3 on CIA

To find out why the arthritis score of the edema and the tumor in the mice paws with CIA were reduced, the paws were cut and mRNAs were isolated from a joint (or articulation) with TRIzol Kit and cDNAs were prepared. Later, RT-PCR of iNOS, COX-2, TNF-α, and IL-1β, the pro-inflammatory protein genes, were carried out (FIG. 7A), and their mRNA expressions were compared with GAPDH (FIG. 7B-F). It turned out that mRNA expressions of iNOS, TNF-α, and IL-1β except for COX-2 were markedly reduced. This result also indicates that the compound 3 effectively suppresses the transcription of iNOS, TNF-α, and IL-1β for treatment of the RA disease model. In addition, the amount of cytokines inside the bloods from the mice through the CIA mode, and $PGE_2$, TNF-α, and IL-1β in the bloods were measured using the sandwich ELISA method. Also, $NO_2^-$ existing inside the bloods was measured using nitrate reductase. These results also prove that the compound 3 is capable of effectively inhibiting pro-inflammatory cytokines and proteins inside the bloods.

As described so far, the pharmaceutical composition according to the present invention including the colchicine derivative of the formulas (I) and (II) and its pharmaceutically acceptable salt as effective components can be advantageously used as immunosuppressive agents, immunomodulating agents, anti-proliferative agents, anti-inflammatory agents and anticancer agents, and feature a lower toxicity than colchicine and a lower risk of being a mutagen.

Although the preferred embodiment of the present invention has been described, it will be understood by those skilled in the art that the present invention should not be limited to the described preferred embodiment, but various changes and modifications can be made within the spirit and scope of the present invention as defined by the appended claims.

What is claimed is:

1. Colchicine derivatives represented by the formula (I) or pharmaceutically acceptable salts thereof:

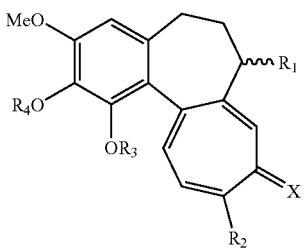

(I)

wherein:
when $R_1$ is $N(R_5)C(X_1)$—A, $R_2$ is hydrogen, $X_2R_6$, or $X_2(O)n_1R_6$; $R_3$ and $R_4$ are independently hydrogen, a methyl group, or a lower straight chain or branched alkyl, wherein $R_5$ and $R_6$ are independently hydrogen, or a lower straight chain or branched alkyl; X, $X_1$, and $X_2$ are independently O or S; $n_1$ is an integer of 1 or 2; and A is selected from the group represented by the following formula:

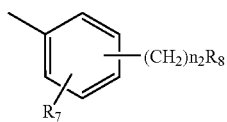

(a)

wherein $R_7$ is a phenyl, a $C_1$ to $C_3$ straight chain or branched alkyl, a $C_1$ to $C_3$ straight chain or branched alkoxy, halogen selected from F, Cl, Br or I, a nitro, or a cyano group; $R_8$ is hydrogen, —ONO$_2$, halogen selected from F, Cl, Br, or I; $n_2$ is an integer from 1 to 3.

2. Colchicine derivative represented by the formula (II) and pharmaceutically acceptable salts thereof:

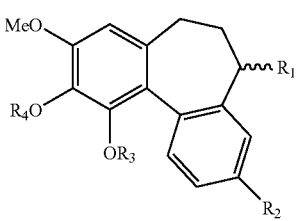

(II)

wherein:
when $R_1$ is $N(R_5)C(X_1)$—A, $R_2$ is hydrogen, $X_2R_6$, or $X_2(O)n_1R_6$; $R_3$ and $R_4$ are independently hydrogen, a methyl group, or a lower straight chain or branched alkyl, wherein $R_5$ and $R_6$ are independently hydrogen, or a lower straight chain or branched alkyl; $X_1$ and $X_2$ are independently O or S; $n_1$ is an integer of 1 or 2; and A is selected from the group represented by the following formula:

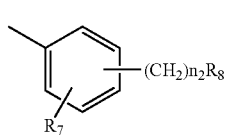

(a)

wherein $R_7$ is a phenyl, a $C_1$ to $C_3$ straight chain or branched alkyl, a $C_1$ to $C_3$ straight chain or branched alkoxy, halogen selected from F, Cl, Br or I, a nitro, or a cyano group; $R_8$ is hydrogen, —ONO$_2$, halogen selected from F, Cl, Br, or I; $n_2$ is an integer from 1 to 3.

3. A compound selected from the group consisting of:
2-Fluoro-3-nitrooxymethyl-N-(1,2,3-trimethoxy-10-methylsulfanyl-9-oxo-5,6,7,9-tetrahydro-benzo[α]heptalen-7-yl)-benzamide;
2-Fluoro-5-bromomethyl-N-(1,2,3-trimethoxy-10-methylsulfanyl-9-oxo-5,6,7,9-tetrahydro-benzo[α]heptalen-7-yl)-benzamide;
2-Chloro-3-nitrooxymethyl-N-(1,2,3-trimethoxy-10-methylsulfanyl-9-oxo-5,6,7,9-tetrahydro-benzo[α]heptalen-7-yl)-benzamide;
2-Chloro-5-chloromethyl-N-(1,2,3-trimethoxy-10-methylsulfanyl-9-oxo-5,6,7,9-tetrahydro-benzo[α]heptalen-7-yl)-benzamide;
2-Iodo-3-nitrooxymethyl-N-(1,2,3-trimethoxy-10-methylsulfanyl-9-oxo-5,6,7,9-tetrahydro-benzo[α]heptalen-7-yl)-benzamide;
2-Cyano-3-nitrooxymethyl-N-(1,2,3-trimethoxy-10-methylsulfanyl-9-oxo-5,6,7,9-tetrahydro-benzo[α]heptalen-7-yl)-benzamide;
2-Bromo-3-nitrooxymethyl-N-(1,2,3-trimethoxy-10-methylsulfanyl-9-oxo-5,6,7,9-tetrahydro-benzo[α]heptalen-7-yl)-benzamide;
2-Phenyl-3-nitrooxymethyl-N-(1,2,3,-trimethoxy-10-methylsulfanyl-9-oxo-5,6,7,9-tetrahydro-benzo[α]heptalen-7-yl)-benzamide;
2-Iodo-3-methyl-N-(1,2,3-trimethoxy-10-methylsulfanyl-9-oxo-5,6,7,9-tetrahydro-benzo[α]heptalen-7-yl)-benzamide;
2-Iodo-3-methyl-N-(1,2,3-trimethoxy-10-methylsulfanyl-9-oxo-5,6,7,9-tetrahydro-benzo[α]heptalen-7-yl)-benzamide;

2-Cyano-3-methyl-N-(1,2,3-trimethoxy-10-methylsulfanyl-9-oxo-5,6,7,9-tetrahydro-benzo[α]heptalen-7-yl)-benzamide;

2-Fluoro-5-methyl-N-(1,2,3-trimethoxy-10-methylsulfanyl-9-oxo-5,6,7,9-tetrahydro-benzo[α]heptalen-7-yl)-benzamide;

2-Nitro-3-nitrooxymethyl-N-(1,2,3-trimethoxy-10-methylsulfanyl-9-oxo-5,6,7,9-tetrahydro-benzo[α]heptalen-7-yl)-benzamide;

3-Methyl-5-nitrooxymethyl-N-(1,2,3-trimethoxy-10-methylsulfanyl-9-oxo-5,6,7,9-tetrahydro-benzo[α]heptalen-7-yl)-benzamide;

2-Methoxy-5-nitrooxymethyl-N-(1,2,3-trimethoxy-10-methylsulfanyl-9-oxo-5,6,7,9-tetrahydro-benzo[α]heptalen-7-yl)-benzamide;

2-Chloro-3-methyl-N-(3,9,10,11-tetramethoxy-6,7-dihydro-5H-dibenzo[a,c]cyclohepten-5-yl)-benzamide 2-Chloro-N-(3-methanesulfonyl-9,10,11-trimethoxy-6,7-dihydro-5H-dibenzo[a,c]cyclohepten-5-yl)-3-methyl-benzamide;

2-Chloro-3-methyl-N-(1,2,3-trimethoxy-10-methylsulfanyl-9-thioxo-5,6,7,9-tetrahydro-benzo[α]heptalen-7-yl)-benzamide;

2-Fluoro-5-nitrooxymethyl-N-(1,2,3-trimethoxy-10-methylsulfanyl-9-oxo-5,6,7,9-tetrahydro-benzo[α]heptalen-7-yl)-benzamide;

4-Fluoro-3-nitrooxymethyl-N-(1,2,3-trimethoxy-10-methylsulfanyl-9-oxo-5,6,7,9-tetrahydro-benzo[α]heptalen-7-yl)-benzamide;

2-Chloro-5-methyl-N-(1,2,3-trimethoxy-10-methylsulfanyl-9-oxo-5,6,7,9-tetrahydro-benzo[α]heptalen-7-yl)-benzamide;

2-Chloro-5-nitrooxymethyl-N-(1,2,3-trimethoxy-10-methylsulfanyl-9-oxo-5,6,7,9-tetrahydro-benzo[α]heptalen-7-yl)-benzamide;

4-Chloro-3-nitrooxymethyl-N-(1,2,3-trimethoxy-10-methylsulfanyl-9-oxo-5,6,7,9-tetrahydro-benzo[α]heptalen-7-yl)-benzamide;

2-Bromo-5-nitrooxymethyl-N-(1,2,3-trimethoxy-10-methylsulfanyl-9-oxo-5,6,7,9-tetrahydro-benzo[α]heptalen-7-yl)-benzamide;

4-Bromo-3-nitrooxymethyl-N-(1,2,3-trimethoxy-10-methylsulfanyl-9-oxo-5,6,7,9-tetrahydro-benzo[α]heptalen-7-yl)-benzamide;

2-Iodo-5-nitrooxymethyl-N-(1,2,3-trimethoxy-10-methylsulfanyl-9-oxo-5,6,7,9-tetrahydro-benzo[α]heptalen-7-yl)-benzamide;

4-Iodo-3-nitrooxymethyl-N-(1,2,3-trimethoxy-10-methylsulfanyl-9-oxo-5,6,7,9-tetrahydro-benzo[α]heptalen-7-yl)-benzamide;

2-Nitro-5-nitrooxymethyl-N-(1,2,3-trimethoxy-10-methylsulfanyl-9-oxo-5,6,7,9-tetrahydro-benzo[α]heptalen-7-yl)-benzamide;

4-Nitro-3-nitrooxymethyl-N-(1,2,3-trimethoxy-10-methylsulfanyl-9-oxo-5,6,7,9-tetrahydro-benzo[α]heptalen-7-yl)-benzamide;

2-Cyano-5-nitrooxymethyl-N-(1,2,3-trimethoxy-10-methylsulfanyl-9-oxo-5,6,7,9-tetrahydro-benzo[α]heptalen-7-yl)-benzamide;

4-Cyano-3-nitrooxymethyl-N-(1,2,3-trimethoxy-10-methylsulfanyl-9-oxo-5,6,7,9-tetrahydro-benzo[α]heptalen-7-yl)-benzamide;

4-Nitrooxymethyl-biphenyl-2-carboxylic acid (1,2,3-trimethoxy-10-methylsulfanyl-9-oxo-5,6,7,9-tetrahydro-benzo[α]heptalen-7-yl)-amide;

2-Nitrooxymethyl-biphenyl-4-carboxylic acid (1,2,3-trimethoxy-10-methylsulfanyl-9-oxo-5,6,7,9-tetrahydro-benzo[α]heptalen-7-yl)-amide;

2-Methoxy-3-nitrooxymethyl-N-(1,2,3-trimethoxy-10-methylsulfanyl-9-oxo-5,6,7,9-tetrahydro-benzo[α]heptalen-7-yl)-benzamide;

4-Methoxy-3-nitrooxymethyl-N-(1,2,3-trimethoxy-10-methylsulfanyl-9-oxo-5,6,7,9-tetrahydro-benzo[α]heptalen-7-yl)-benzamide;

or pharmaceutically acceptable salts thereof.

4. A pharmaceutical composition comprising a colchicine derivative or its pharmaceutically acceptable salt according to claim 1 or 2 as an active ingredient.

5. A method for providing an immuno-suppressive effect comprising administering to a patient in need of such an effect an effective amount of one or more colchicine derivatives according to claim 1.

6. A method for providing an anti-inflammatory effect comprising administering to a patient in need of such an effect an effective amount of one or more colchicine derivatives according to claim 1.

7. A method for providing an immuno-suppressive effect comprising administering to a patient in need of such an effect an effective amount of one or more colchicine derivatives according to claim 2.

8. A method for providing an anti-inflammatory effect comprising administering to a patient in need of such an effect an effective amount of one or more colchicine derivatives according to claim 2.

* * * * *